(12) United States Patent
Chen et al.

(10) Patent No.: US 6,251,944 B1
(45) Date of Patent: Jun. 26, 2001

(54) PARA-SUBSTITUTED PHENYLENE DERIVATIVES

(75) Inventors: Barbara B. Chen, Glenview, IL (US); Helen Y. Chen, Livingston, NJ (US); Glen J. Gesicki, Morton Grove, IL (US); Richard A. Haack, Chicago, IL (US); James W. Malecha, Libertyville, IL (US); Thomas D. Penning, Elmhurst, IL (US); Joseph G. Rico; Thomas E. Rogers, both of Ballwin, MO (US); Peter G. Ruminski, Dardenne Prairie, MO (US); Mark A. Russell, Gurnee; Stella S. Yu, Morton Grove, both of IL (US)

(73) Assignee: G. D. Searle & Company, Chicago, IL (US)

( * ) Notice: Subject to any disclaimer, the term of this patent is extended or adjusted under 35 U.S.C. 154(b) by 0 days.

(21) Appl. No.: 09/288,742

(22) Filed: Apr. 8, 1999

Related U.S. Application Data

(62) Division of application No. 08/826,244, filed on Mar. 27, 1997.
(60) Provisional application No. 60/014,288, filed on Mar. 29, 1996.

(51) Int. Cl.$^7$ .................... A61K 31/19; C07C 229/00; C07C 205/00
(52) U.S. Cl. .................... 514/565; 514/564; 514/563; 514/557; 514/561; 560/19; 560/20; 560/35; 560/21
(58) Field of Search .................... 514/565; 560/21, 560/20, 35

(56) References Cited

FOREIGN PATENT DOCUMENTS

| 333071 | * | 4/1992 | (EP) . |
| 478328 | * | 4/1992 | (EP) . |
| 9532710 | * | 12/1995 | (WO) . |

OTHER PUBLICATIONS

Choay et al. (CA 95: 132533, abstract of FR 2456731), Dec. 1998.*

* cited by examiner

*Primary Examiner*—Sabiha Qazi
(74) *Attorney, Agent, or Firm*—Rachel A. Polster

(57) ABSTRACT

The present invention relates to a class of compounds represented by Formula I

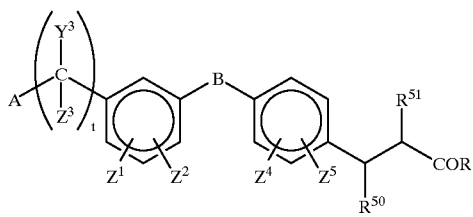

or a pharmaceutically acceptable salt thereof, pharmaceutical composition comprising compounds of the Formula I, and methods of selectively inhibiting or antagonizing the $\alpha_v\beta_3$ integrin.

30 Claims, No Drawings

PARA-SUBSTITUTED PHENYLENE DERIVATIVES

This application is a divisional of co-pending U.S. Ser. No. 08/826,244, filed Mar. 27, 1997, now allowed, which claims priority under 35 USC §119(e) of U.S. provisional application Serial No. 60/014,288, filed Mar. 29, 1996.

FIELD OF THE INVENTION

The present invention relates to pharmaceutical agents (compounds) which are useful as $\alpha_v\beta_3$ integrin antagonists and as such are useful in pharmaceutical compositions and in methods for treating conditions mediated by $\alpha_v\beta_3$ by inhibiting or antagonizing $\alpha_v\beta_3$ integrins.

BACKGROUND OF THE INVENTION

Integrins are a group of cell surface glycoproteins which mediate cell adhesion and therefore are useful mediators of cell adhesion interactions which occur during various biological processes. Integrins are heterodimers composed of noncovalently linked α and β polypeptide subunits. Currently eleven different α subunits have been identified and six different β subunits have been identified. The various α subunits can combine with various β subunits to form distinct integrins.

The integrin identified as $\alpha_v\beta_3$ (also known as the vitronectin receptor) has been identified as an integrin which plays a role in various conditions or disease states including tumor metastasis, solid tumor growth (neoplasia), osteoporosis, Paget's disease, humoral hypercalcemia of malignancy, angiogenesis, including tumor angiogenesis, retinopathy, arthritis, including rheumatoid arthritis, periodontal disease, psoriasis and smooth muscle cell migration (e.g. restenosis). Additionally, it has been found that such agents would be useful as antivirals, antifungals and antimicrobials. Thus, compounds which selectively inhibit or antagonize $\alpha_v\beta_3$ would be beneficial for treating such conditions.

It has been shown that the $\alpha_v\beta_3$ integrin and other $\alpha_v$ containing integrins bind to a number of Arg-Gly-Asp (RGD) containing matrix macromolecules. Compounds containing the RGD sequence mimic extracellular matrix ligands so as to bind to cell surface receptors. However, it is also known that RGD peptides in general are non-selective for RGD dependent integrins. For example, most RGD peptides which bind to $\alpha_v\beta_3$ also bind to $\alpha_v\beta_5$, $\alpha_v\beta_1$ and $\alpha_{IIb}\beta_3$. Antagonism of platelet $\alpha_{IIb}\beta_3$ (also known as the fibrinogen receptor) is known to block platelet aggregation in humans. In order to avoid bleeding side-effects when treating the conditions or disease states associated with the integrin $\alpha_v\beta_3$, it would be beneficial to develop compounds which are selective antagonists of $\alpha_v\beta_3$ as opposed to $\alpha_v\beta_3$.

Tumor cell invasion occurs by a three step process: 1) tumor cell attachment to extracellular matrix; 2) proteolytic dissolution of the matrix; and 3) movement of the cells through the dissolved barrier. This process can occur repeatedly and can result in metastases at sites distant from the original tumor.

Seftor et al. (Proc. Natl. Acad. Sci. USA, Vol. 89 (1992) 1557–1561) have shown that the $\alpha_v\beta_3$ integrin has a biological function in melanoma cell invasion. Montgomery et al., (Proc. Natl. Acad. Sci. USA, Vol. 91 (1994) 8856–60) have demonstrated that the integrin $\alpha_v\beta_3$ expressed on human melanoma cells promotes a survival signal, protecting the cells from apoptosis. Mediation of the tumor cell metastatic pathway by interference with the $\alpha_v\beta_3$ integrin cell adhesion receptor to impede tumor metastasis would be beneficial.

Brooks et al. (Cell, Vol. 79 (1994) 1157–1164) have demonstrated that antagonists of $\alpha_v\beta_3$ provide a therapeutic approach for the treatment of neoplasia (inhibition of solid tumor growth) since systemic administration of $\alpha_v\beta_3$ antagonists causes dramatic regression of various histologically distinct human tumors.

The adhesion receptor integrin $\alpha_v\beta_3$ was identified as a marker of angiogenic blood vessels in chick and man and therefore such receptor plays a critical role in angiogenesis or neovascularization. Angiogenesis is characterized by the invasion, migration and proliferation of smooth muscle and endothelial cells. Antagonists of $\alpha_v\beta_3$ inhibit this process by selectively promoting apoptosis of cells in neovasculature. The growth of new blood vessels, or angiogenesis, also contributes to pathological conditions such as diabetic retinopathy (Adonis et al., Amer. J. Ophthal., Vol. 118, (1994) 445–450) and rheumatoid arthritis (Peacock et al., J. Exp. Med., Vol. 175, (1992), 1135–1138). Therefore, $\alpha_v\beta_3$ antagonists would be useful therapeutic targets for treating such conditions associated with neovascularization (Brooks et al., Science, Vol. 264, (1994), 569–571).

It has been reported that the cell surface receptor $\alpha_v\beta_3$ is the major integrin on osteoclasts responsible for attachment to bone. Osteoclasts cause bone resorption and when such bone resorbing activity exceeds bone forming activity it results in osteoporosis (a loss of bone), which leads to an increased number of bone fractures, incapacitation and increased mortality. Antagonists of $\alpha_v\beta_3$ have been shown to be potent inhibitors of osteoclastic activity both in vitro [Sato et al., J. Cell. Biol., Vol. 111 (1990) 1713–1723] and in vivo [Fisher et al., Endocrinology, Vol. 132 (1993) 1411–1413]. Antagonism of $\alpha_v\beta_3$ leads to decreased bone resorption and therefore restores a normal balance of bone forming and resorbing activity. Thus it would be beneficial to provide antagonists of osteoclast $\alpha_v\beta_3$ which are effective inhibitors of bone resorption and therefore are useful in the treatment or prevention of osteoporosis.

The role of the $\alpha_v\beta_3$ integrin in smooth muscle cell migration also makes it a therapeutic target for prevention or inhibition of neointimal hyperplasia which is a leading cause of restenosis after vascular procedures (Choi et al., J. Vasc. Surg. Vol. 19(1) (1994) 125–34). Prevention or inhibition of neointimal hyperplasia by pharmaceutical agents to prevent or inhibit restenosis would be beneficial.

White (Current Biology, Vol. 3(9)(1993) 596–599) has reported that adenovirus uses $\alpha_v\beta_3$ for entering host cells. The integrin appears to be required for endocytosis of the virus particle and may be required for penetration of the viral genome into the host cell cytoplasm. Thus compounds which inhibit $\alpha_v\beta_3$ would find usefulness as antiviral agents.

SUMMARY OF THE INVENTION

The present invention relates to a class of compounds represented by the Formula I

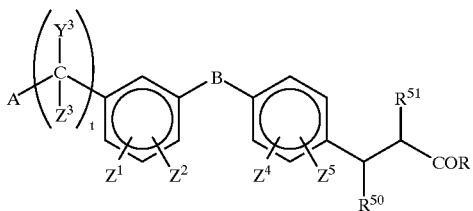

or a pharmaceutically acceptable salt thereof, wherein

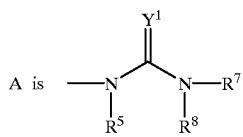

wherein $Y^1$ is selected from the group consisting of $N-R^2$, O, and S;

$R^2$ is selected from the group consisting of H; alkyl; aryl; hydroxy; alkoxy; cyano; nitro; amino; aminocarbonyl; alkenyl; alkynyl; alkyl optionally substituted with one or more substituent selected from lower alkyl, halogen, hydroxyl, haloalkyl, cyano, nitro, carboxyl, amino, alkoxy, aryl or aryl optionally substituted with one or more halogen, haloalkyl, lower alkyl, alkoxy, cyano, alkylsulfonyl, alkylthio, nitro, carboxyl, amino, hydroxyl, sulfonic acid, sulfonamide, aryl, fused aryl, monocyclic heterocycles, or fused monocyclic heterocycles; aryl optionally substituted with one or more substituent selected from halogen, haloalkyl, hydroxy, lower alkyl, alkoxy, methylenedioxy, ethylenedioxy, cyano, nitro, alkylthio, alkylsulfonyl, sulfonic acid, sulfonamide, carboxyl derivatives, amino, aryl, fused aryl, monocyclic heterocycles and fused monocyclic heterocycle; monocyclic heterocycles; and monocyclic heterocycles optionally substituted with one or more substituent selected from halogen, haloalkyl, lower alkyl, alkoxy, amino, nitro, hydroxy, carboxyl derivatives, cyano, alkylthio, alkylsulfonyl, sulfonic acid, sulfonamide, aryl or fused aryl; or $R^2$ taken together with $R^7$ forms a 4–12 membered dinitrogen containing heterocycle optionally substituted with one or more substituent selected from the group consisting of lower alkyl, hydroxy and phenyl and wherein said ring optionally contains a heteroatom selected from the group consisting of O and S;

or $R^2$ taken together with $R^7$ forms a 5 membered heteroaromatic ring optionally substituted with amino;

or $R^2$ taken together with $R^7$ forms a 5 membered heteroaromatic ring fused with a phenyl group;

$R^7$ (when not taken together with $R^2$) and $R^8$ are independently selected from the group consisting of H; alkyl; alkenyl; alkynyl; aralkyl; cycloalkyl; bicycloalkyl; aryl; acyl; benzoyl; alkyl optionally substituted with one or more substituent selected from lower alkyl, halogen, hydroxy, haloalkyl, cyano, nitro, carboxyl derivatives, amino, alkoxy, thio, alkylthio, sulfonyl, aryl, aralkyl, aryl optionally substituted with one or more substituent selected from halogen, haloalkyl, lower alkyl, alkoxy, methylenedioxy, ethylenedioxy, alkylthio, haloalkylthio, thio, hydroxy, cyano, nitro, carboxyl derivatives, aryloxy, amido, acylamino, amino, alkylamino, dialkylamino, trifluoroalkoxy, trifluoromethyl, sulfonyl, alkylsulfonyl, haloalkylsulfonyl, sulfonic acid, sulfonamide, aryl, fused aryl, monocyclic heterocycles, fused monocyclic heterocycles; aryl optionally substituted with one or more substituent selected from halogen, haloalkyl, lower alkyl, alkoxy, methylenedioxy, ethylenedioxy, alkylthio, haloalkylthio, thio, hydroxy, cyano, nitro, carboxyl derivatives, aryloxy, amido, acylamino, amino, alkylamino, dialkylamino, trifluoroalkoxy, trifluoromethylsulfonyl, alkylsulfonyl, sulfonic acid, sulfonamide, aryl, fused aryl, monocyclic heterocycles, or fused monocyclic heterocycles; monocyclic heterocycles; monocyclic heterocycles optionally substituted with one or more substituent selected from halogen, haloalkyl, lower alkyl, alkoxy, aryloxy, amino, nitro, hydroxy, carboxyl derivatives, cyano, alkylthio, alkylsulfonyl, aryl, fused aryl; monocyclic and bicyclic heterocyclicalkyls; $-SO_2R^{10}$ wherein $R^{10}$ is selected from the group consisting of alkyl, aryl and monocyclic heterocycles, all optionally substituted with one or more substituent selected from the group consisting of halogen, haloalkyl, alkyl, alkoxy, cyano, nitro, amino, acylamino, trifluoroalkyl, amido, alkylaminosulfonyl, alkylsulfonyl, alkylsulfonylamino, alkylamino, dialkylamino, trifluoromethylthio, trifluoroalkoxy, trifluoromethylsulfonyl, aryl, aryloxy, thio, alkylthio, and monocyclic heterocycles; and

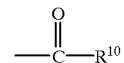

wherein $R^{10}$ is defined above; or $NR^7$ and $R^8$ taken together form a 4–12 membered mononitrogen containing monocyclic or bicyclic ring optionally substituted with one or more substituent selected from lower alkyl, carboxyl derivatives, aryl or hydroxy and wherein said ring optionally contains a heteroatom selected from the group consisting of O, N and S;

$R^5$ is selected from the group consisting of H, alkyl, alkenyl, alkynyl, benzyl, and phenethyl;

or

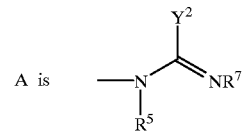

wherein $Y^2$ is selected from the group consisting of H, alkyl; cycloalkyl; bicycloalkyl; aryl; monocyclic heterocycles; alkyl optionally substituted with aryl which can also be optionally substituted with one or more substituent selected from halo, haloalkyl, alkyl, nitro, hydroxy, alkoxy, aryloxy, aryl, or fused aryl; aryl optionally substituted with one or more substituent selected from halo, haloalkyl, hydroxy, alkoxy, aryloxy, aryl, fused aryl, nitro, methylenedioxy, ethylenedioxy, or alkyl; alkynyl; alkenyl; $-S-R^9$ and $-O-R^9$ wherein $R^9$ is selected from the group consisting of H; alkyl; aralkyl; aryl; alkenyl; and alkynyl; or $R^9$ taken together with $R^7$ forms a 4–12 membered mononitrogen containing sulfur or oxygen containing heterocyclic ring; and $R^5$ and $R^7$ are as defined above;

or $Y^2$ (when $Y^2$ is carbon) taken together with $R^7$ forms a 4–12 membered mononitrogen containing ring optionally substituted with alkyl, aryl or hydroxy;

or A is 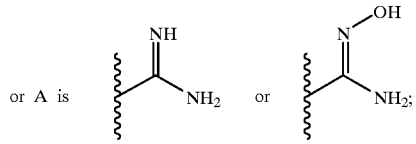

$Z^1$, $Z^2$, $Z^4$ and $Z^5$ are independently selected from the group consisting of H; alkyl; hydroxy; alkoxy; aryloxy; aralkoxy; halogen; haloalkyl; haloalkoxy; nitro; amino; aminoalkyl; alkylamino; dialkylamino; cyano; alkylthio; alkylsulfonyl; carboxyl derivatives; carboxyalkyl; alkoxycarbonylalkyl; acetamide; aryl; fused aryl; cycloalkyl; thio; monocyclic heterocycles; fused monocyclic heterocycles; and A, wherein A is defined above;

B is selected from the group consisting of

—CH$_2$CONH—, —CONR$^{52}$—(CH$_2$)$_p$—, —C(O)O—O, —SO$_2$NH—, —CH$_2$O—, and —OCH$_2$—;

wherein p is an integer selected from the group consisting of 0, 1 and 2;

wherein $R^{50}$ is selected from the group consisting of H, alkyl, aryl, carboxyl derivatives and —CONHCH$_2$CO$_2$R$^{53}$ wherein $R^{53}$ is H or lower alkyl;

$R^{52}$ is selected from the group consisting of H or alkyl;

$R^{51}$ is selected from the group consisting of H, alkyl, carboxyl derivatives,

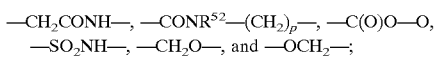

—NHCOR$^{54}$, —NHCOR$^{55}$ and amino;

wherein $R^{54}$ is selected from the group consisting of H, alkyl, cycloalkyl, aryl, aralkyl, aralkenyl, and aryl substituted by one or more alkyl or halo; wherein $R^{55}$ is selected from the group consisting of N-substituted pyrrolidinyl, piperidinyl and morpholinyl;

t is an integer 0, 1 or 2;

R is X—R$^3$ wherein X is selected from the group consisting of O, S and NR$^4$, wherein R$^3$ and R$^4$ are independently selected from the group consisting of hydrogen; alkyl; alkenyl; alkynyl; haloalkyl; aryl; arylalkyl; sugars; steroids and in the case of the free acid, all pharmaceutically acceptable salts thereof; and $Y^3$ and $Z^3$ are independently selected from the group consisting of H, alkyl, aryl, cycloalkyl and aralkyl or $Y^3$ and $Z^3$ taken together with the C form a carbonyl.

This invention also relates to a class of compounds represented by the Formula II

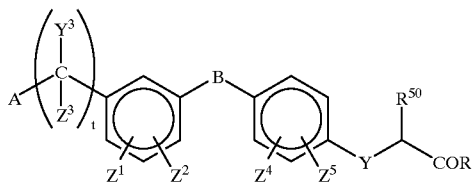

or a pharmaceutically acceptable salt thereof, wherein
Y is selected from the group consisting of —O—, —S— and —SO$_2$—; wherein A is 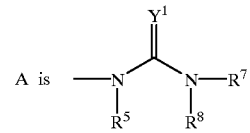

wherein $Y^1$ is selected from the group consisting of N—R$^2$, O, and S;

$R^2$ is selected from the group consisting of H; alkyl; aryl; hydroxy; alkoxy; cyano; nitro; amino; aminocarbonyl; alkenyl; alkynyl; alkyl optionally substituted with one or more substituent selected from lower alkyl, halogen, hydroxyl, haloalkyl, cyano, nitro, carboxyl, amino, alkoxy, aryl or aryl optionally substituted with one or more halogen, haloalkyl, lower alkyl, alkoxy, cyano, alkylsulfonyl, alkylthio, nitro, carboxyl, amino, hydroxyl, sulfonic acid, sulfonamide, aryl, fused aryl, monocyclic heterocycles, or fused monocyclic heterocycles; aryl optionally substituted with one or more substituent selected from halogen, haloalkyl, hydroxy, lower alkyl, alkoxy, methylenedioxy, ethylenedioxy, cyano, nitro, alkylthio, alkylsulfonyl, sulfonic acid, sulfonamide, carboxyl derivatives, amino, aryl, fused aryl, monocyclic heterocycles and fused monocyclic heterocycle; monocyclic heterocycles; and monocyclic heterocycles optionally substituted with one or more substituent selected from halogen, haloalkyl, lower alkyl, alkoxy, amino, nitro, hydroxy, carboxyl derivatives, cyano, alkylthio, alkylsulfonyl, sulfonic acid, sulfonamide, aryl or fused aryl; or $R^2$ taken together with $R^7$ forms a 4–12 membered dinitrogen containing heterocycle optionally substituted with one or more substituent selected from the group consisting of lower alkyl, hydroxy and phenyl;

or $R^2$ taken together with $R^7$ forms a 5 membered heteroaromatic ring optionally substituted with amino;

or $R^2$ taken together with $R^7$ forms a 5 membered heteroaromatic ring optionally substituted with amino fused with a phenyl group;

$R^7$ (when not taken together with $R^2$) and $R^8$ are independently selected from the group consisting of H; alkyl; alkenyl; alkynyl; aralkyl; cycloalkyl; bicycloalkyl; aryl; acyl; benzoyl; alkyl optionally substituted with one or more substituent selected from lower alkyl, halogen, hydroxy, haloalkyl, cyano, nitro, carboxyl derivatives, amino, alkoxy, thio, alkylthio, sulfonyl, aryl, aralkyl, aryl optionally substituted with one or more substituent selected from halogen, haloalkyl, lower alkyl, alkoxy, methylenedioxy, ethylenedioxy, alkylthio, haloalkylthio, thio, hydroxy, cyano, nitro, carboxyl derivatives, aryloxy, amido, acylamino, amino, alkylamino, dialkylamino, trifluoroalkoxy, trifluoromethyl, sulfonyl, alkylsulfonyl, haloalkylsulfonyl, sulfonic acid, sulfonamide, aryl, fused aryl, monocyclic heterocycles, fused monocyclic heterocycles; aryl optionally substituted with one or more substituent selected from halogen, haloalkyl, lower alkyl, alkoxy, methylenedioxy, ethylenedioxy, alkylthio, haloalkylthio, thio, hydroxy, cyano, nitro, carboxyl derivatives, aryloxy, amido, acylamino, amino, alkylamino, dialkylamino, trifluoroalkoxy, trifluoromethylsulfonyl, alkylsulfonyl, sulfonic acid, sulfonamide, aryl, fused aryl, monocyclic heterocycles, or fused monocyclic heterocycles; monocyclic heterocycles; monocyclic heterocycles optionally substituted with one or more substituent selected from halogen, haloalkyl, lower alkyl, alkoxy, aryloxy, amino, nitro, hydroxy, carboxyl derivatives, cyano, alkylthio, alkylsulfonyl, aryl, fused aryl; monocyclic and bicyclic heterocyclicalkyls; —SO$_2$R$^{10}$ wherein R$^{10}$ is selected from the group consisting of alkyl, aryl and monocyclic heterocycles, all optionally substituted with one or more substituent selected from the group consisting of halogen, haloalkyl, alkyl, alkoxy, cyano, nitro, amino, acylamino, trifluoroalkyl, amido, alkylaminosulfonyl, alkylsulfonyl, alkylsulfonylamino, alkylamino, dialkylamino, trifluoromethylthio, trifluoroalkoxy, trifluoromethylsulfonyl, aryl, aryloxy, thio, alkylthio, and monocyclic heterocycles; and

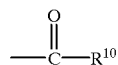

wherein R$^{10}$ is defined above; or NR$^7$ and R$^8$ taken together form a 4–12 membered mononitrogen containing monocyclic or bicyclic ring optionally substituted with one or more substituent selected from lower alkyl, carboxyl derivatives, aryl or hydroxy and wherein said ring optionally contains a heteroatom selected from the group consisting of O, N and S;

R$^5$ is selected from the group consisting of H, alkyl, alkenyl, alkynyl, benzyl, and phenethyl;

or

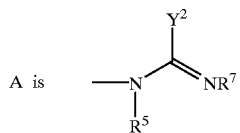

wherein Y$^2$ is selected from the group consisting of alkyl; cycloalkyl; bicycloalkyl; aryl; monocyclic heterocycles; alkyl optionally substituted with aryl which can also be optionally substituted with one or more substituent selected from halo, haloalkyl, alkyl, nitro, hydroxy, alkoxy, aryloxy, aryl, or fused aryl; aryl optionally substituted with one or more substituent selected from halo, haloalkyl, hydroxy, alkoxy, aryloxy, aryl, fused aryl, nitro, methylenedioxy, ethylenedioxy, or alkyl; alkynyl; alkenyl; —S—R$^9$ and —O—R$^9$ wherein R$^9$ is selected from the group consisting of H; alkyl; aralkyl; aryl; alkenyl; and alkynyl; or R$^9$ taken together with R$^7$ forms a 4–12 membered mononitrogen containing sulfur or oxygen containing heterocyclic ring; and R$^5$ and R$^7$ are as defined above;

or Y$^2$ (when Y$^2$ is carbon) taken together with R$^7$ forms a 4–12 membered mononitrogen containing ring optionally substituted with alkyl, aryl or hydroxy;

or A is 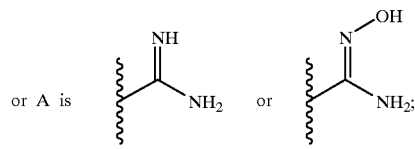

Z$^1$, Z$^2$, Z$^4$ and Z$^5$ are independently selected from the group consisting of H; alkyl; hydroxy; alkoxy; aryloxy; aralkoxy; halogen; haloalkyl; haloalkoxy; nitro; amino; aminoalkyl; alkylamino; dialkylamino; cyano; alkylthio; alkylsulfonyl; carboxyl derivatives; carboxyalkyl; alkoxycarbonylalkyl; acetamide; aryl; fused aryl; cycloalkyl; thio; monocyclic heterocycles; fused monocyclic heterocycles; and A, wherein A is defined above;

B is selected from the group consisting of

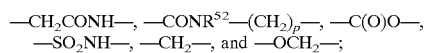

wherein p is an integer selected from the group consisting of 0, 1 and 2;

wherein R$^{50}$ is selected from the group consisting of H, alkyl, aryl and carboxyl derivatives;

R$^{52}$ is selected from the group consisting of H or alkyl;

t is an integer 0, 1 or 2;

R is X—R$^3$ wherein X is selected from the group consisting of O, S and NR , wherein R$^3$ and R$^4$ are independently selected from the group consisting of hydrogen; alkyl; alkenyl; alkynyl; haloalkyl; aryl; aralalkyl; sugars; steroids and in the case of the free acid, all pharmaceutically acceptable salts thereof; and Y$^3$ and Z$^3$ are independently selected from the group consisting of H, alkyl, aryl, cycloalkyl and aralkyl or Y$^3$ and Z$^3$ taken together with C form a carbonyl.

It is another object of the invention to provide pharmaceutical compositions comprising compounds of the Formulas I and II. Such compounds and compositions are useful in selectively inhibiting or antagonizing the α$_v$β$_3$ and therefore in another embodiment the present invention relates to a method of selectively inhibiting or antagonizing the α$_v$β$_3$ integrin. The invention further involves treating or inhibiting pathological conditions associated therewith such as osteoporosis, humoral hypercalcemia of malignancy, Paget's disease, tumor metastasis, solid tumor growth (neoplasia), angiogenesis, including tumor angiogenesis, retinopathy including diabetic retinopathy, arthritis, including rheumatoid arthritis, periodontal disease, psoriasis, smooth muscle cell migration and restenosis in a mammal in need of such treatment. Additionally, such pharmaceutical agents are useful as antiviral agents, and antimicrobials.

DETAILED DESCRIPTION

The present invention relates to a class of compounds represented by the Formulas I and II, described above.

A preferred embodiment of the present invention is a compound of the Formula III

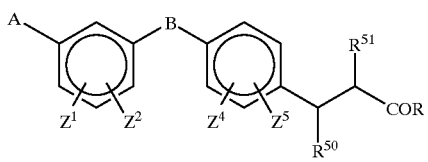

Another preferred embodiment of the present invention is a compound of the Formula IV

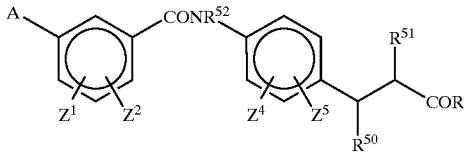

Another preferred embodiment of the present invention is a compound of the Formula V

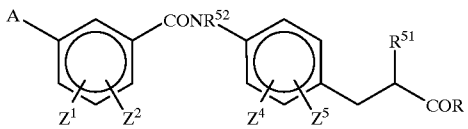

Another preferred embodiment of the present invention is a compound of the Formula VI

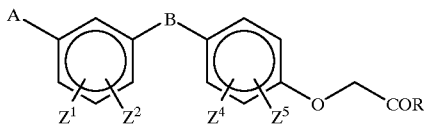

Another preferred embodiment of the present invention is a compound of the Formula VII

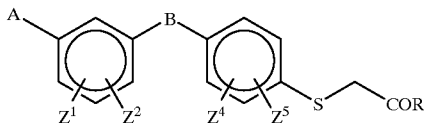

Another preferred embodiment of the present invention is a compound of the Formula VIII

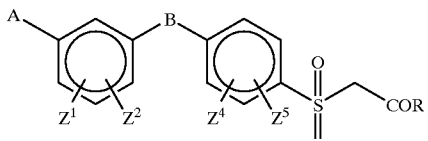

When the compound of the invention is of the formula

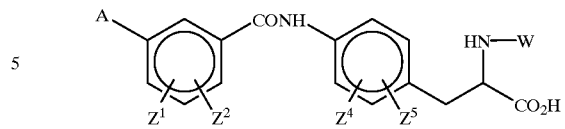

the compounds can be racemic or R or S stereochemistry. However, the S stereochemisty (derived from the natural amino acid, i.e. L-form) is the most preferred, followed by the racemic and followed by the R-stereoisomer.

The invention further relates to pharmaceutical compositions containing therapeutically effective amounts of the compounds of Formulas I–VIII.

The invention also relates to a method of selectively inhibiting or antagonizing the $\alpha_v\beta_3$ integrin and more specifically relates to a method of inhibiting bone resorption, periodontal disease, osteoporosis, humoral hypercalcemia of malignancy, Paget's disease, tumor metastasis, solid tumor growth (neoplasia), angiogenesis, including tumor angiogenesis, retinopathy including diabetic retinopathy, arthritis, including rheumatoid arthritis, smooth muscle cell migration and restenosis by administering a therapeutically effective amount of a compound of the Formula I–VIII to achieve such inhibition together with a pharmaceutically acceptable carrier.

The following is a list of definitions of various terms used herein:

As used herein, the terms "alkyl" or "lower alkyl" refer to a straight chain or branched chain hydrocarbon radicals having from about 1 to about 10 carbon atoms, and more preferably 1 to about 6 carbon atoms. Examples of such alkyl radicals are methyl, ethyl, n-propyl, isopropyl, n-butyl, isobutyl, sec-butyl, t-butyl, pentyl, neopentyl, hexyl, isohexyl, and the like.

As used herein the terms "alkenyl" or "lower alkenyl" refer to unsaturated acyclic hydrocarbon radicals containing at least one double bond and 2 to about 6 carbon atoms, which carbon—carbon double bond may have either cis or trans geometry within the alkenyl moiety, relative to groups substituted on the double bond carbons. Examples of such groups are ethenyl, propenyl, butenyl, isobutenyl, pentenyl, hexenyl and the like.

As used herein the terms "alkynyl" or "lower alkynyl" refer to acyclic hydrocarbon radicals containing one or more triple bonds and 2 to about 6 carbon atoms. Examples of such groups are ethynyl, propynyl, butynyl, pentynyl, hexynyl and the like.

The term "cycloalkyl" as used herein means saturated or partially unsaturated cyclic carbon radicals containing 3 to about 8 carbon atoms and more preferably 4 to about 6 carbon atoms. Examples of such cycloalkyl radicals include cyclopropyl, cyclopropenyl, cyclobutyl, cyclopentyl, cyclohexyl, 2-cyclohexen-1-yl, and the like.

The term "aryl" as used herein denotes aromatic ring systems composed of one or more aromatic rings. Preferred aryl groups are those consisting of one, two or three aromatic rings. The term embraces aromatic radicals such as phenyl, pyridyl, naphthyl, thiophene, furan, biphenyl and the like.

As used herein, the term "cyano" is represented by a radical of the formula

The terms "hydroxy" and "hydroxyl" as used herein are synonymous and are represented by a radical of the formula

The term "lower alkylene" or "alkylene" as used herein refers to divalent linear or branched saturated hydrocarbon radicals of 1 to about 6 carbon atoms.

As used herein the term "alkoxy" refers to straight or branched chain oxy containing radicals of the formula —$OR^{20}$, wherein $R^{20}$ is an alkyl group as defined above. Examples of alkoxy groups encompassed include methoxy, ethoxy, n-propoxy, n-butoxy, isopropoxy, isobutoxy, sec-butoxy, t-butoxy and the like.

As used herein the terms "arylalkyl" or "aralkyl" refer to a radical of the formula

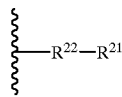

wherein $R^{21}$ is aryl as defined above and $R^{22}$ is an alkylene as defined above. Examples of aralkyl groups include benzyl, pyridylmethyl, naphthylpropyl, phenethyl and the like.

As used herein the term "aralkenyl" is represented by a radical of the formula

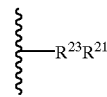

where $R^{21}$ is aryl as defined above and $R^{23}$ is alkylene of 2–6 carbon atoms with one or more C—C double bonds.

As used herein the term "aralkoxy" or "arylalkoxy" refers to a radical of the formula

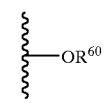

wherein $R^{60}$ is aralkyl as defined above.

As used herein the term "nitro" is represented by a radical of the formula

As used herein the term "halo" or "halogen" refers to bromo, chloro, fluoro or iodo.

As used herein the term "haloalkyl" refers to alkyl groups as defined above substituted with one or more of the same or different halo groups at one or more carbon atom. Examples of haloalkyl groups include trifluoromethyl, dichloroethyl, fluoropropyl and the like.

As used herein the term "N-substituted pyrrolidinyl, piperidinyl, and morpholinyl" refer respectively to radicals of the formula

As used herein the term "carboxyl" or "carboxy" refers to a radical of the formula —COOH.

As used herein the term "carboxyl derivative" refers to a radical of the formula

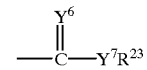

wherein $Y^6$ and $Y^7$ are independently selected from the group consisting of O, N or S and $R^{23}$ is selected from the group consisting of H, alkyl, aralkyl or aryl as defined above.

As used herein the term "amino" is represented by a radical of the formula —$NH_2$.

As used herein the term aminoalkyl" refers to a radical of the formula

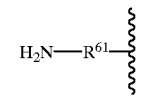

wherein $R^{61}$ is alkylene as defined above.

As used herein the term "alkylsulfonyl" or "alkylsulfone" refers to a radical of the formula

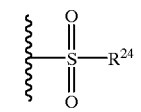

wherein $R^{24}$ is alkyl as defined above.

As used herein the term "alkylthio" refers to a radical of the formula —$SR^{24}$ wherein $R^{24}$ is alkyl as defined above.

As used herein the term "sulfonic acid" refers to a radical of the formula

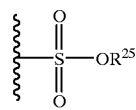

wherein $R^{25}$ is H, alkyl or aryl as defined above.

As used herein the term "sulfonamide" refers to a radical of the formula

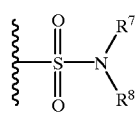

wherein $R^7$ and $R^8$ are as defined above.

As used herein the term "fused aryl" refers to an aromatic ring such as the aryl groups defined above fused to one or more phenyl rings. Embraced by the term "fused aryl" is the radical naphthyl.

As used herein the terms "monocyclic heterocycle" or "monocyclic heterocyclic" refer to a monocyclic ring containing from 4 to about 12 atoms, and more preferably from 5 to about 10 atoms, wherein 1 to 3 of the atoms are heteroatoms selected from the group consisting of oxygen, nitrogen and sulfur with the understanding that if two or more different heteroatoms are present at least one of the heteroatoms must be nitrogen. Representative of such monocyclic heterocycles are imidazole, furan, pyridine, oxazole, pyran, triazole, thiophene, pyrazole, thiazole, thiadiazole, and the like.

As used herein the term "fused monocyclic heterocycle" refers to a monocyclic heterocycle as defined above with a benzene fused thereto. Examples of such fused monocyclic heterocycles include benzofuran, benzopyran, benzodioxole, benzothiazole, benzothiophene, benzimidazole and the like.

As used herein the term "methylenedioxy" refers to the radical

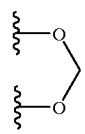

and the term "ethylenedioxy" refers to the radical

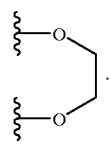

As used herein the term "4–12 membered dinitrogen containing heterocycle refers to a radical of the formula

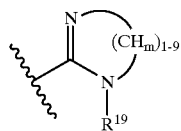

wherein m is 1 or 2 and $R^{19}$ is H, alkyl, aryl, or aralkyl and more preferably refers to 4–9 membered ring and includes rings such as imidazoline.

As used herein the term "5-membered heteroaromatic ring" includes for example a radical of the formula

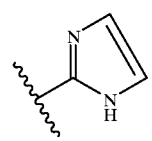

and "5-membered heteroaromatic ring fused with a phenyl" refers to such a "5-membered heteroaromatic ring" with a phenyl fused thereto. Representative of such 5-membered heteroaromatic rings fused with a phenyl is benzimidazole.

As used herein the term "bicycloalkyl" refers to a bicyclic hydrocarbon radical containing 6 to about 12 carbon atoms which is saturated or partially unsaturated.

As used herein the term "acyl" refers to a radical of the formula

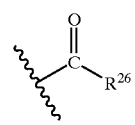

wherein $R^{26}$ is alkyl, alkenyl, alkynyl, aryl or aralkyl as defined above. Encompassed by such radical are the groups acetyl, benzoyl and the like.

As used herein the term "thio" refers to a radical of the formula

As used herein the term "sulfonyl" refers to a radical of the formula

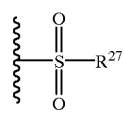

wherein $R^{27}$ is alkyl, aryl or aralkyl as defined above.

As used herein the term "haloalkylthio" refers to a radical of the formula —S—$R^{28}$ wherein $R^{28}$ is haloalkyl as defined above.

As used herein the term "aryloxy" refers to a radical of the formula

wherein $R^{29}$ is aryl as defined above.

As used herein the term "acylamino" refers to a radical of the formula

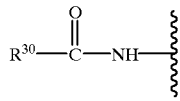

wherein $R^{30}$ is alkyl, aralkyl or aryl as defined above.

As used herein the term "amido" refers to a radical of the formula

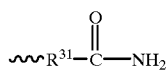

wherein $R^{31}$ is a bond or alkylene as defined above.

As used herein the term "alkylamino" refers to a radical of the formula —$NHR^{32}$ wherein $R^{32}$ is alkyl as defined above.

As used herein the term "dialkylamino" refers to a radical of the formula —$NR^{33}R^{34}$ wherein $R^{33}$ and $R^{34}$ are the same or different alkyl groups as defined above.

As used herein the term "trifluoromethyl" refers to a radical of the formula

As used herein the term "trifluoroalkoxy" refers to a radical of the formula

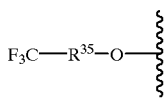

wherein $R^{35}$ is a bond or an alkylene as defined above.

As used herein the term "alkylaminosulfonyl" refers to a radical of the formula

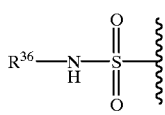

wherein $R^{36}$ is alkyl as defined above.

As used herein the term "alkylsulfonylamino" refers to a radical of the formula

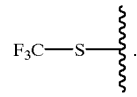

wherein $R^{36}$ is alkyl as defined above.

As used herein the term "trifluoromethylthio" refers to a radical of the formula

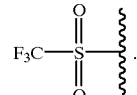

As used herein the term "trifluoromethylsulfonyl" refers to a radical of the formula

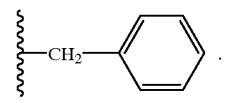

As used herein the term "4–12 membered mono-nitrogen containing monocyclic or bicyclic ring" refers to a saturated or partially unsaturated monocyclic or bicyclic ring of 4–12 atoms and more preferably a ring of 4–9 atoms wherein one atom is nitrogen. Such rings may optionally contain additional heteroatoms selected from nitrogen, oxygen or sulfur. Included within this group are morpholine, piperidine, piperazine, thiomorpholine, pyrrolidine, proline, azacycloheptene and the like.

As used herein the term "benzyl" refers to the radical

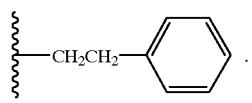

As used herein the term "phenethyl" refers to the radical

As used herein the term "4–12 membered mononitrogen containing sulfur or oxygen containing heterocyclic ring" refers to a ring consisting of 4 to 12 atoms and more preferably 4 to 9 atoms wherein at least one atom is a nitrogen and at least one atom is oxygen or sulfur. Encompassed within this definition are rings such as thiazoline and the like.

As used herein the term "arylsulfonyl" or "arylsulfone" refers to a radical of the formula

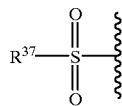

wherein $R^{37}$ is aryl as defined above.

As used herein the terms "alkylsulfoxide" or "arylsulfoxide" refer to radicals of the formula

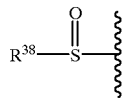

wherein $R^{38}$ is, respectively, alkyl or aryl as defined above.

As used herein the term "phosphonic acid derivative" refers to a radical of the formula

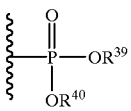

wherein $R^{39}$ and $R^{40}$ are the same or different H, alkyl, aryl or aralkyl.

As used herein the term "phosphinic acid derivatives" refers to a radical of the formula

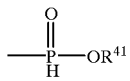

wherein $R^{41}$ is H, alkyl, aryl or aralkyl as defined above.

As used herein the term "arylthio" refers to a radical of the formula

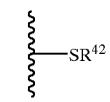

wherein $R^{42}$ is aryl as defined above.

As used herein the term "monocyclic heterocycle thio" refers to a radical of the formula

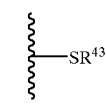

wherein $R^{43}$ is a monocyclic heterocycle radical as defined above.

As used herein the terms "monocyclic heterocycle sulfoxide" and "monocyclic heterocycle sulfone" refer, respectively, to radicals of the formula

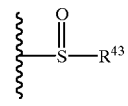

and

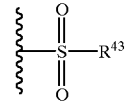

wherein $R^{43}$ is a monocyclic heterocycle radical as defined above.

The term "composition" as used herein means a product which results from the mixing or combining of more than one element or ingredient.

The term "pharmaceutically acceptable carrier", as used herein means a pharmaceutically-acceptable material, composition or vehicle, such as a liquid or solid filler, diluent, excipient, solvent or encapsulating material, involved in carrying or transporting a chemical agent.

The term "therapeutically effective amount" shall mean that amount of drug or pharmaceutical agent that will elicit the biological or medical response of a tissue, system or animal that is being sought by a researcher or clinician.

The following is a list of abbreviations and the corresponding meanings as used interchangeably herein:

$^1$H-NMR=proton nuclear magnetic resonance
AcOH=acetic acid
$BH_3$-THF=borane-tetrahydrofuran complex
BOC=tert-butoxycarbonyl
Cat.=catalytic amount
$CH_2Cl_2$=dichloromethane
$CH_3CN$=acetonitrile
$CH_3I$=iodomethane
CHN analysis=carbon/hydrogen/nitrogen elemental analysis
CHNCl analysis=carbon/hydrogen/nitrogen/chlorine elemental analysis
CHNS analysis=carbon/hydrogen/nitrogen/sulfur elemental analysis
DCC=1,3-dicyclohexylcarbodiimide
DIEA=diisopropylethylamine
DMA=N,N-dimethylacetamide
DMAP=4-(N,N-dimethylamino)pyridine
DMF=N,N-dimethylformamide
DSC=disuccinyl carbonate
EDCI=1-(3-dimethylaminopropyl)-3-ethylcarbodiimide hydrochloride
$Et_2O$=diethyl ether
$Et_3N$=triethylamine
EtOAc=ethyl acetate
EtOH=ethanol
FAB MS=fast atom bombardment mass spectroscopy
g=gram(s)
GIHA HCl=meta-guanidino-hippuric acid hydrochloride
GIHA=meta-guanidino-hippuric acid HPLC=high performance liquid chromatography
IBCF=isobutylchloroformate
$K_2CO_3$=potassium carbonate
KOH=potassium hydroxide
LiOH=lithium hydroxide
MCPBA=m-chloroperoxybenzoic acid or m-chloroperbenzoic acid
MeOH=methanol
MesCl=methanesulfonylchloride
mg=milligram
$MgSO_4$=magnesium sulfate
ml=milliliter
mL=milliliter
MS=mass spectroscopy
$N_2$=nitrogen
$NaCNBH_3$=sodium cyanoborohydride
$Na_2PO_4$=sodium phosphate
$Na_2SO_4$=sodium sulfate
$NaHCO_3$=sodium bicarbonate
NaOH=sodium hydroxide
$NH_4HCO_3$=ammonium bicarbonate
$NH_4{}^+HCO_2$=ammonium formate
NMM=N-methyl morpholine
NMR=nuclear magnetic resonance
RPHPLC=reverse phase high performance liquid chromatography
RT=room temperature
KSCN=potassium thiocyanate
Pd/C=palladium on carbon
Bn=benzyl
Et=ethyl
Me=methyl
Ph=phenyl
$NEt_3$=triethylamine
t-BOC=tert-butoxycarbonyl
TFA=trifluoroacetic acid
THF=tetrahydrofuran
Δ=heating the reaction mixture As used herein HPLC-Method 1 refers to reverse phase C-18 functionalized silica gel column (50×300 mm) using a linear gradient of 95% 0.6% TFA/water:5% $CH_3CN$ to 60% 0.6% TFA/water: 40% $CH_3CN$ with a flow rate of 80 ml/minute.

The compounds as shown in Formulas I–VIII can exist in various isomeric forms and all such isomeric forms are meant to be included. Tautomeric forms are also included as well as pharmaceutically acceptable salts of such isomers and tautomers.

In the structures and formulas herein, a bond drawn across a bond of a ring can be to any available atom on the ring.

The term "pharmaceutically acceptable salt" refers to a salt prepared by contacting a compound of Formula I or II with an acid whose anion is generally considered suitable for human consumption. Examples of pharmacologically acceptable salts include the hydrochloride, hydrobromide, hydroiodide, sulfate, phosphate, acetate, propionate, lactate, maleate, malate, succinate, tartrate salts and the like. All of the pharmacologically acceptable salts may be prepared by conventional means. (See Berge et al., *J Pharm. Sci.*, 66(1), 1–19 (1977) for additional examples of pharmaceutically acceptable salts.)

For the selective inhibition or antagonism of $\alpha_v\beta_3$ integrins, compounds of the present invention may be administered orally, parenterally, or by inhalation spray, or topically in unit dosage formulations containing conventional pharmaceutically acceptable carriers, adjuvants and vehicles. The term parenteral as used herein includes, for example, subcutaneous, intravenous, intramuscular, intrasternal, infusion techniques or intraperitonally.

The compounds of the present invention are administered by any suitable route in the form of a pharmaceutical composition adapted to such a route, and in a dose effective for the treatment intended. Therapeutically effective doses of the compounds required to prevent or arrest the progress of or to treat the medical condition are readily ascertained by one of ordinary skill in the art using preclinical and clinical approaches familiar to the medicinal arts.

Accordingly, the present invention provides a method of treating conditions mediated by selectively inhibiting or antagonizing the $\alpha_v\beta_3$ cell surface receptor which method comprises administering a therapeutically effective amount of a compound selected from the class of compounds depicted in Formulas I–VIII, wherein one or more compounds of the Formulas I–VIII is administered in association with one or more non-toxic, pharmaceutically acceptable carriers and/or diluents and/or adjuvants (collectively referred to herein as "carrier" materials) and if desired other active ingredients. More specifically, the present invention provides a method for inhibition of the $\alpha_v\beta_3$ cell surface receptor. Most preferably the present invention provides a method for inhibiting bone resorption, treating osteoporosis, inhibiting humoral hypercalcemia of malignancy, treating Paget's disease, inhibiting tumor metastasis, inhibiting neoplasia (solid tumor growth), inhibiting angiogenesis including tumor angiogenesis, treating diabetic retinopathy, inhibiting arthritis, psoriasis and periodontal disease, and inhibiting smooth muscle cell migration including restenosis.

Based upon standard laboratory experimental techniques and procedures well known and appreciated by those skilled in the art, as well as comparisons with compounds of known usefulness, the compounds of Formula I can be used in the treatment of patients suffering from the above pathological conditions. One skilled in the art will recognize that selection of the most appropriate compound of the invention is within the ability of one with ordinary skill in the art and will depend on a variety of factors including assessment of results obtained in standard assay and animal models.

Treatment of a patient afflicted with one of the pathological conditions comprises administering to such a patient an amount of compound of the Formula I or II which is therapeutically effective in controlling the condition or in prolonging the survivability of the patient beyond that expected in the absence of such treatment. As used herein, the term "inhibition" of the condition refers to slowing, interrupting, arresting or stopping the condition and does not necessarily indicate a total elimination of the condition. It is believed that prolonging the survivability of a patient, beyond being a significant advantageous effect in and of itself, also indicates that the condition is beneficially controlled to some extent.

As stated previously, the compounds of the invention can be used in a variety of biological, prophylactic or therapeutic areas. It is contemplated that these compounds are useful in prevention or treatment of any disease state or condition wherein the $\alpha_v\beta_3$ integrin plays a role.

The dosage regimen for the compounds and/or compositions containing the compounds is based on a variety of factors, including the type, age, weight, sex and medical condition of the patient; the severity of the condition; the route of administration; and the activity of the particular compound employed. Thus the dosage regimen may vary widely. Dosage levels of the order from about 0.01 mg to about 1000 mg per kilogram of body weight per day are useful in the treatment of the above-indicated conditions and more preferably of the order from about 0.01 mg to about 100 mg per kilogram.

The active ingredient administered by injection is formulated as a composition wherein, for example, saline, dextrose or water may be used as a suitable carrier. A suitable daily dose would typically be about 0.01 to 100 mg/kg body weight injected per day in multiple doses depending on the factors listed above and more preferably of the order from about 0.01 to 10 mg/kg.

For administration to a mammal in need of such treatment, the compounds in a therapeutically effective amount are ordinarily combined with one or more adjuvants appropriate to the indicated route of administration. The compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulphuric acids, gelatin, acacia, sodium alginate, polyvinylpyrrolidone, and/or polyvinyl alcohol, and tableted or encapsulated for convenient administration. Alternatively, the compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

The pharmaceutical compositions useful in the present invention may be subjected to conventional pharmaceutical operations such as sterilization and/or may contain conventional pharmaceutical adjuvants such as preservatives, stabilizers, wetting agents, emulsifiers, buffers, etc.

The general synthetic sequences for preparing the compounds useful in the present invention are outlined in Schemes I–IV. Both an explanation of, and the actual procedures for, the various aspects of the present invention are described where appropriate. The following Schemes and Examples are intended to be merely illustrative of the present invention, and not limiting thereof in either scope or spirit. Those of skill in the art will readily understand that known variations of the conditions and processes described in the Schemes and Examples can be used to perform the process of the present invention.

Unless otherwise indicated all starting materials and equipment employed were commercially available.

SCHEME I

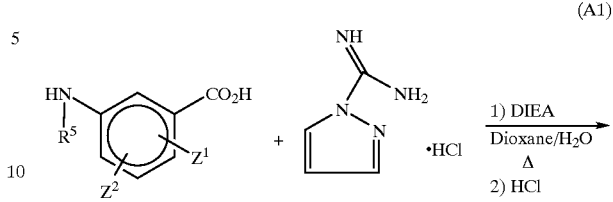

(A1)

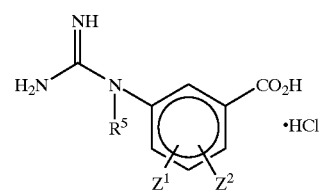

(A2)

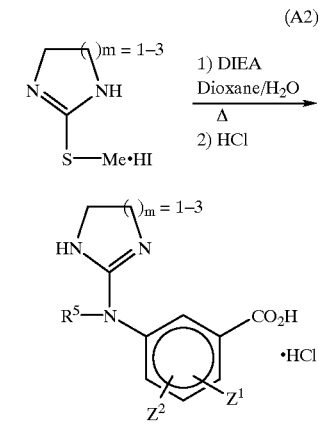

(A3)

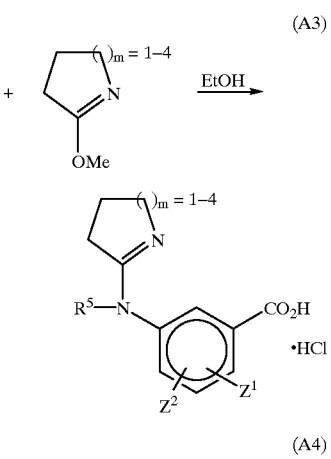

(A4)

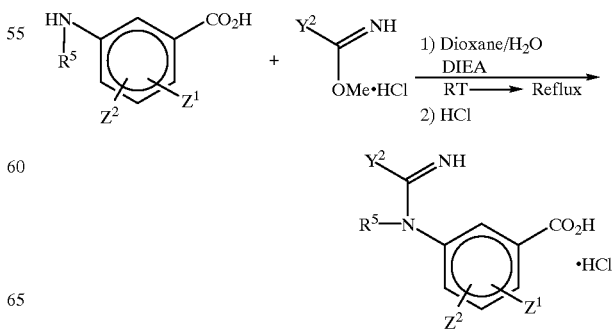

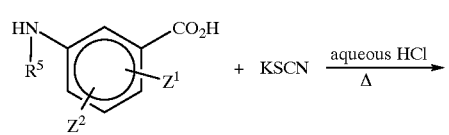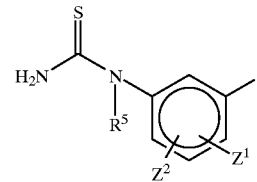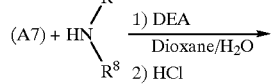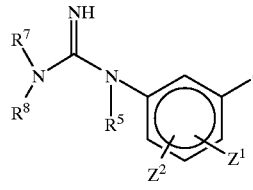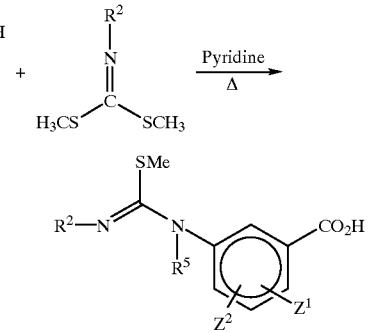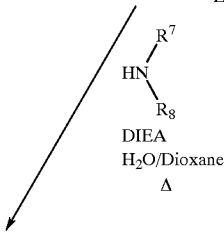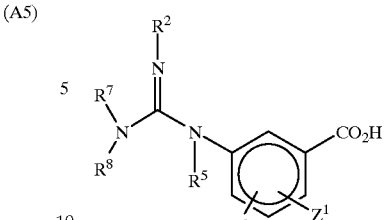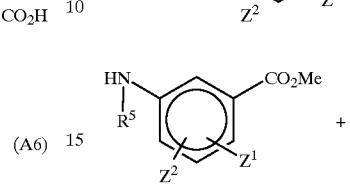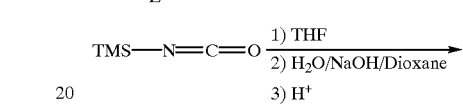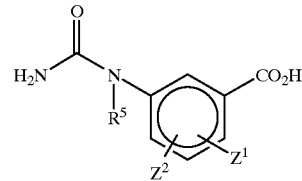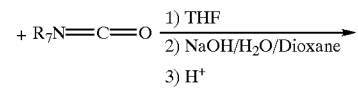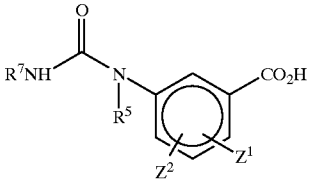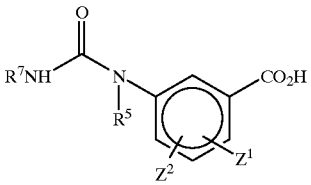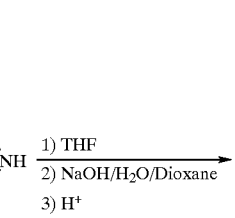

-continued

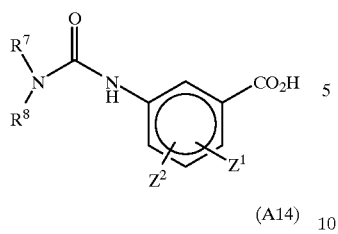
(A14)

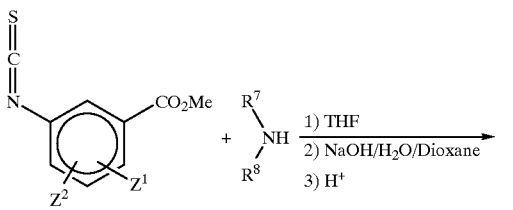

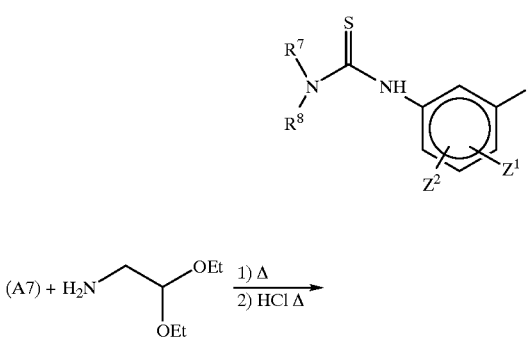
(A15)

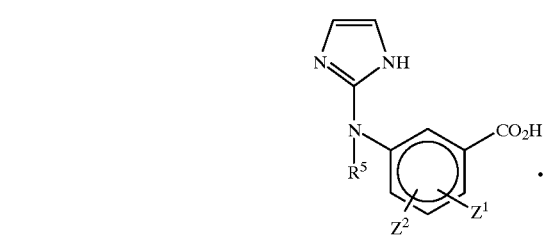
·HCl
(A16)

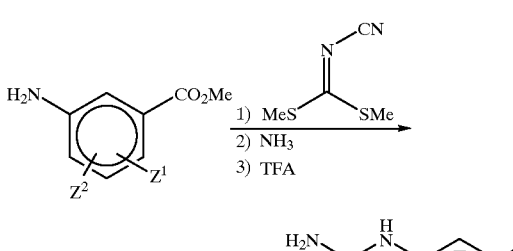

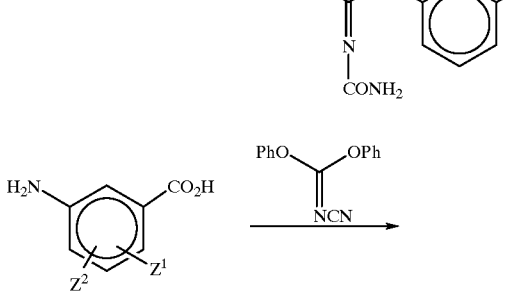
(A17)

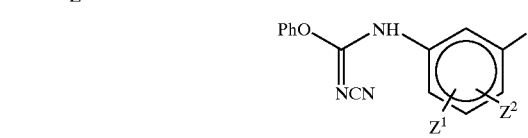

-continued

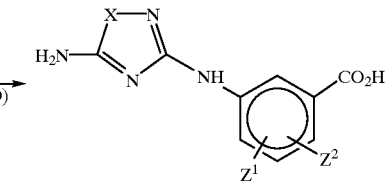
(A18)

Schemes I, II and III are illustrative of methodology useful for preparing various compounds of the present invention. Such methodology is more specifically defined in the examples which follow. Such methodology can be modified by one skilled in the art, substituting known reagents and conditions from conventional methodology to produce the desired compounds.

Specifically, in Scheme I:

In the synthesis of intermediate benzoic acids (A1) through (A16), the starting amino benzoic acids

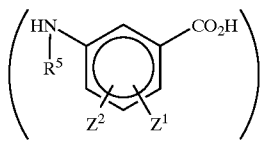

are either commercially available or can be converted to such amino benzoic acids via reduction of the corresponding nitro benzoic acid, which can be obtained commercially or synthesized by nitration of the appropriate benzoic acid, followed by reduction to the desired amino benzoic acid. These are all when $R^5$ is H. If $R^5$ is other than H, alkylation of the amino functionality can be achieved by conventional methodology.

Furthermore, synthesis of intermediate (A2) can also be accomplished as disclosed generally in U.S. Pat. No. 3,202, 660, starting with the appropriate amino benzoic acid. Furthermore, intermediate (A2) and (A15) as well as further analogues of (A2) and (A15) such as substitutions on the heterocyclic ring, oxazolidines, thiazolidines, benzimidazoles and the like can also be accomplished as disclosed in 1) Chem. Pharm. Bull. 41(1) 117–125 (1993)
2) Chem. Pharm. Bull. 33(10) 4409–4421 (1985)
3) J. Med. Chem. 18 (1), 90–99 (1975).

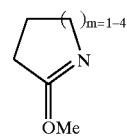

used in the synthesis of intermediates (A3), can be synthesized from

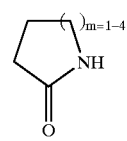

and $(Me)_3OBF_4$ in dichloromethane.

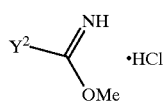
used in the synthesis of intermediate (A4), can be synthesized from $Y^2$—CN and MeOH (1 equivalent) and HCl gas (1 equivalent) in heptane.
All other reagents in Scheme I are either commercially available or readily synthesized by methodologies known by those skilled in the art.
SCHEME II
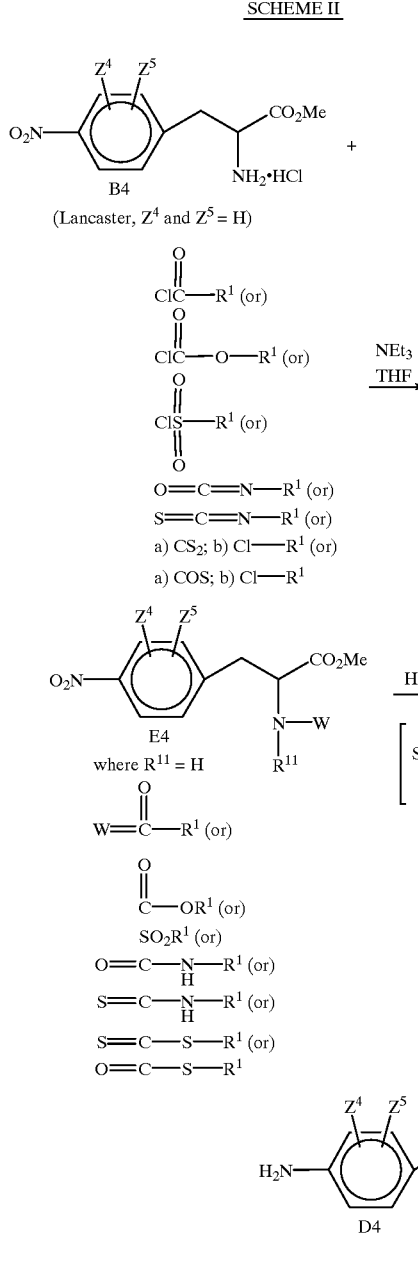
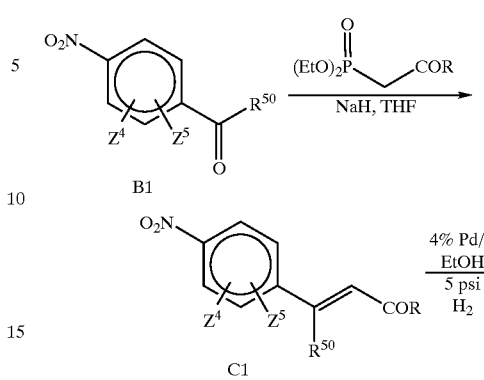
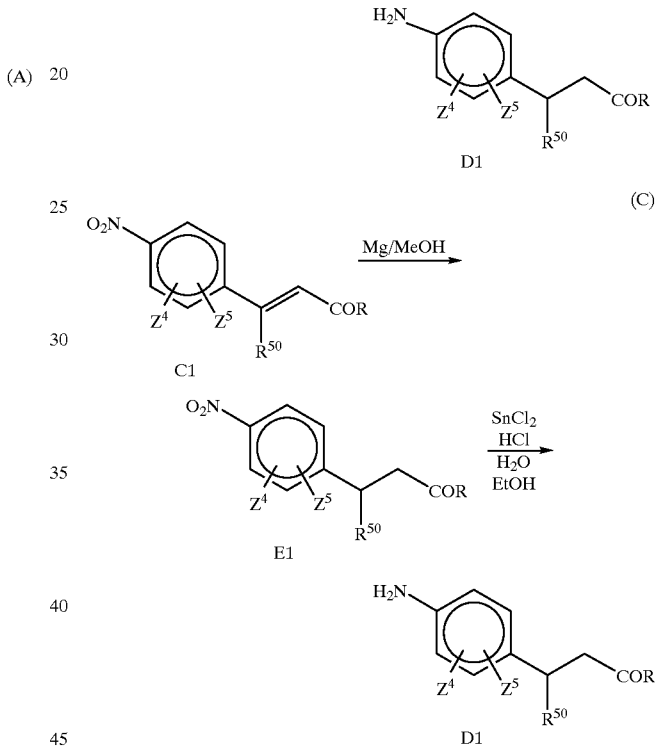
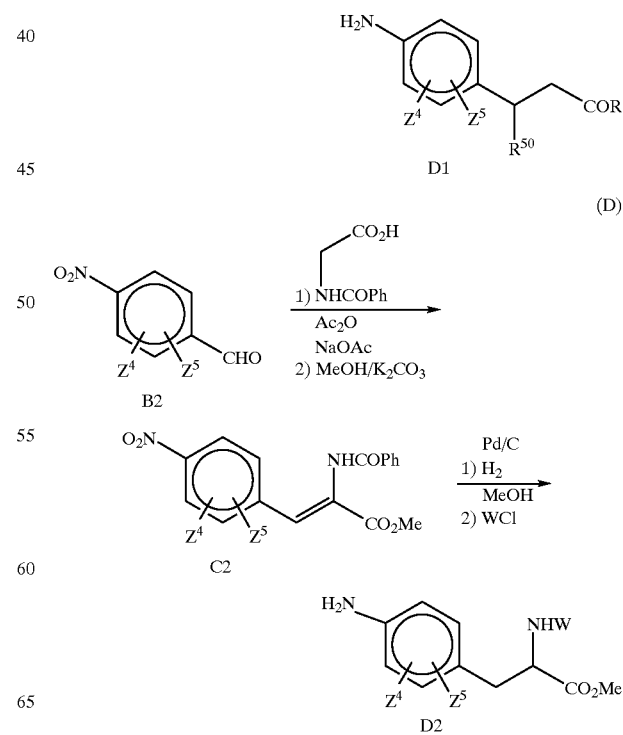

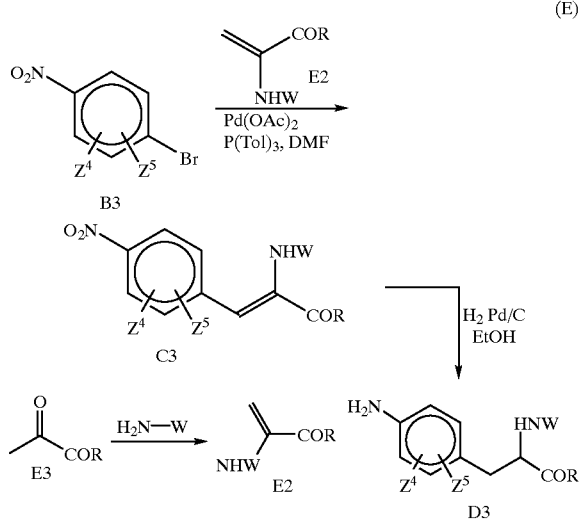

In Scheme II(A), phenylpropionic acid analogs D4 are readily prepared from 4-nitrophenyl alanine methyl esters B4 using the following procedure.

Nitrophenyl alanine B4 condenses with a variety of electrophiles such as $R^1COCl$, $R^1OCOCl$, $R^1SO_2Cl$, $R^1N=C=O$, $R^1N=C=S$, $R^1SCOCl$ under standard conditions ($NEt_3$, THF) known in the art. The resulting intermediate E4 is reduced by either catalytic hydrogenation ($H_2$, Pd/C, MeOH), or tin II chloride ($SnCl_2$, $H_2O$, HCl, EtOH 100°) to afford the desired phenylpropionic acid analog D4.

In Scheme II(B) phenylpropionic acid analog D1 is readily prepared from aldehyde/or ketone B1 in the following manner.

Aldehyde or ketone B1 is condensed with $(EtO)_2P(O)CH_2COR$ under standard conditions (NaH/THF 0° to room temperature). The resulting cinnamic acid derivative C1 is reduced (4% Pd/C, EtOH, 5 psi) to afford the desired phenylpropionic acid analogs D1.

When substituents $Z^4$ and $Z^5$ are sensitive to the catalytic hydrogenation conditions described above, the following synthetic procedure depicted in Scheme II(C) may be utilized.

Nitrophenylcinnamic acid derivative C1 is partially reduced with magnesium in MeOH to afford nitrophenylpropionic acid analog E1, further reduction of the nitro moiety ($SnCl_2/H_2O/HCl/EtOH$) affords the desired phenylpropionic acid derivative D1.

In Scheme II(D) phenylpropionic acid derivative D2 can be readily prepared from aldehyde B2 as described below.

Aldehyde B2 is condensed with N-benzoyl glycine ($Ac_2O/100°$) and the resulting azalactone is hydrolysed ($MeOH/K_2CO_3$) to afford the corresponding dehydroamino acid analog C2. Hydrogenation of C2 (Pd/C, $H_2$, MeOH, 60 psi) followed by derivatisation with the electrophilic reagents W—Cl (as described in Scheme II(A) affords phenylpropionic acid derivative D2.

In Scheme II(E), phenylpropionic acid analog D3 may be prepared from bromide B3.

Bromide B3 is readily coupled to acrylate E2 using standard Heck coupling procedures such as ($Pd(OAc)_2$, $P(Tol)_3$, DMF, 130°) to afford the corresponding dehydroamino acid derivative C3. Hydrogenation of C3 (Pd/C, $H_2$, EtOH, 60 psi) affords the desired phenylpropionic acid analog B3.

Furthermore acrylates E2 are readily prepared from condensation of pyruvic acid derivatives with $H_2N$—W using standard dehydrating conditions such as (Tol, $POCl_3$).

Coupling of the intermediates from Scheme I [(A1) through (A16)] with the intermediates (D1–D4) (from Scheme II) can be accomplished using other coupling reagents known to those in the art in addition to the mixed anhydride method described in Scheme III, to give the final desired products.

SCHEME III

Method A

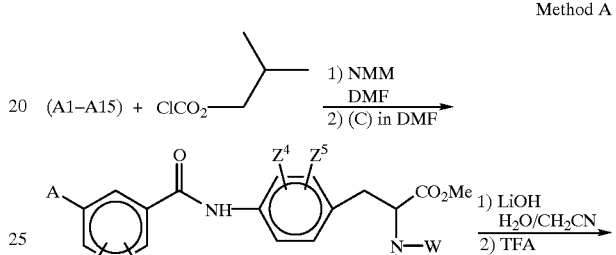

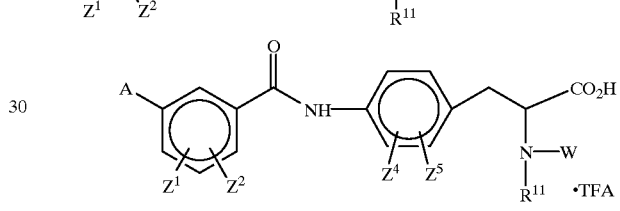

Method B

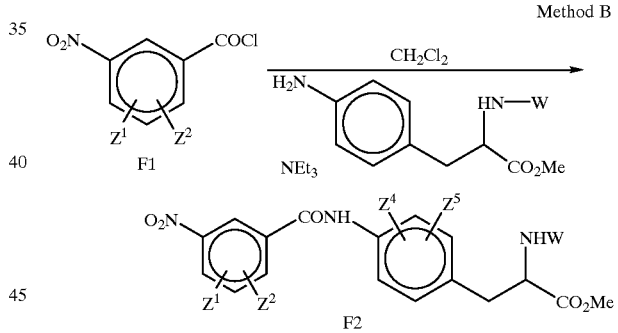

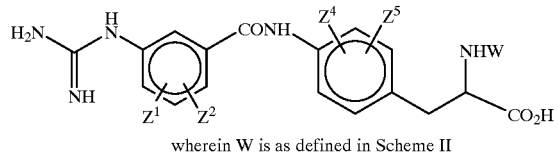

wherein W is as defined in Scheme II

In Scheme III—Method B

An alternative method to prepare compounds of the present invention is described below.

In this procedure, intermediates D1–D4 [from Scheme II (A–F)] are coupled to 3-nitrobenzoylchloride F1 ($CH_2Cl_2$, $NEt_3$ 0°). The resulting coupled product F2 is reduced ($SnCl_2/EtOH$, $H_2O$, 100°) to the corresponding aniline. The resulting aniline can be converted into compounds of the present invention using the reactions described in Scheme I (A1–A6) or reacted with protected cyclic or acyclic thioureos, followed by deprotection (TFA/CH$_2$Cl$_2$/0°).

This procedure is exemplified by converting the above aniline to its correspondence guanidine analog (BOCNHCSNHBOC, HgCl$_2$ DMF) followed by deprotection (TFA, CH$_2$cl$_2$)

When R$^{11}$ is not H, the appropriate nitrogen can be alkylated in an appropriate step by methodology known to those skilled in the art. Alternate acid derivatives R are synthesized by methodologies known to those skilled in the art.

To synthesize compounds wherein

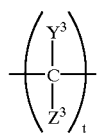

where t = 1 and Y$^3$ and Z$^3$ are both hydrogen:

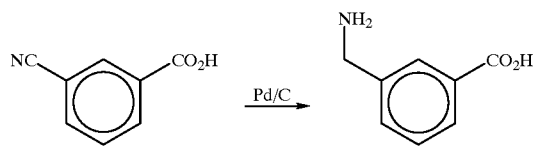

which is then treated in the same manner of further derivatization as exemplified in the previous schemes for:

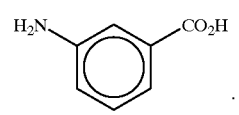

SCHEME IV

STEP 1

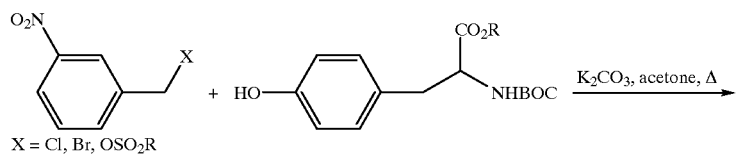

X = Cl, Br, OSO$_2$R

STEP 2

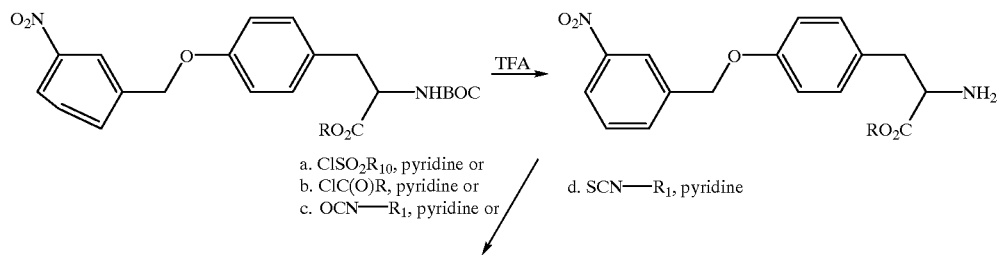

a. ClSO$_2$R$_{10}$, pyridine or
b. ClC(O)R, pyridine or
c. OCN——R$_1$, pyridine or
d. SCN——R$_1$, pyridine

STEP 3

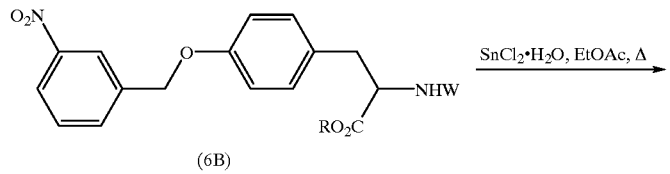

(6B)

STEP 4

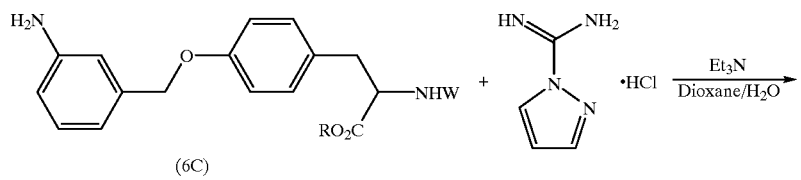

(6C)

STEP 5

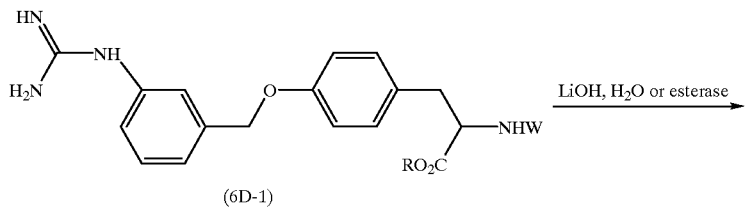

STEP 4 (Cont'd)

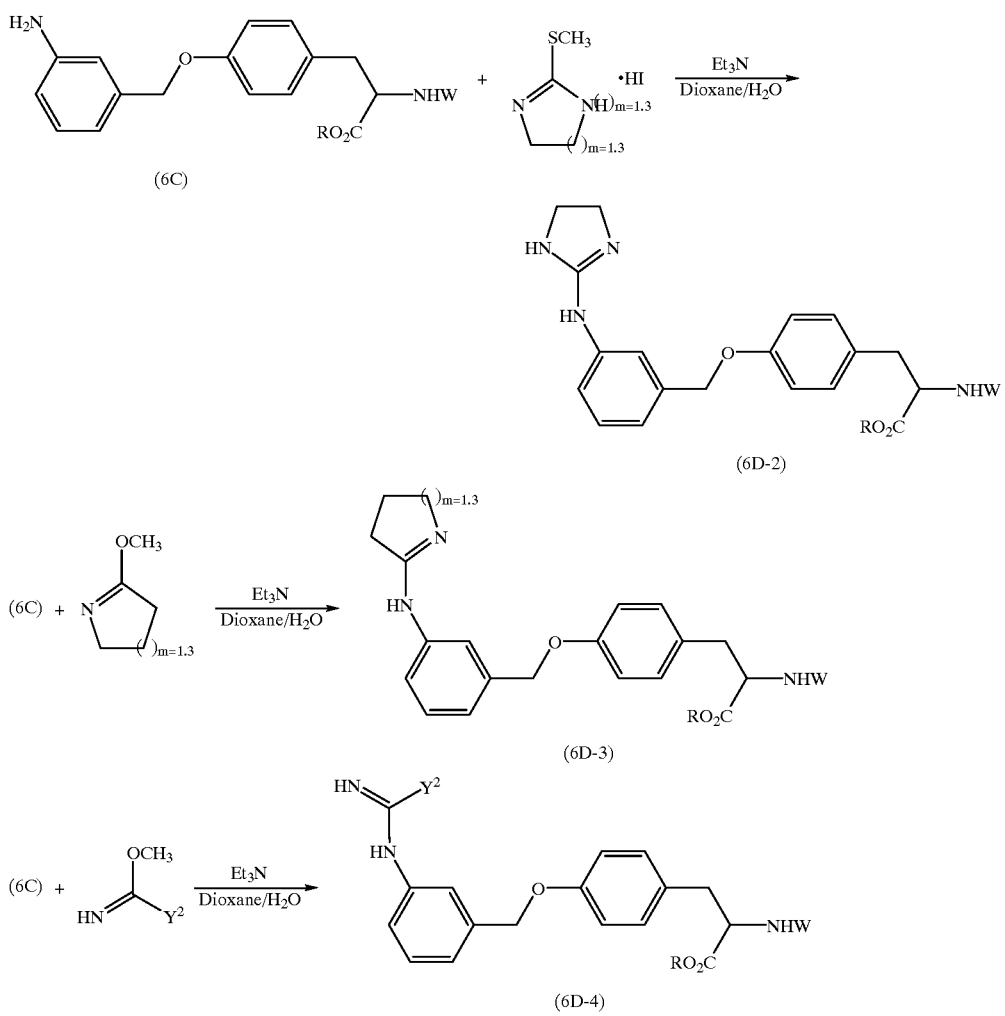

Scheme IV outlines methodologies for preparing tyrosine derivatives of the present invention. Thus, Scheme IV, Step 1 outlines the formation of the nitrobenzyl ether tyrosine derivative by reaction of nitrobenzyl halide or sulfonate ester with a properly protected tyrosine derivative (e.g. BOC protected) using a base such as potassium carbonate and solvent such as acetone. The BOC protecting group can be removed using standard procedures (TFA, or HCl/EtOAc, or HCl/dioxane) to give the primary amine, 6A. The amine can be functionalized with various electrophiles (e.g. Scheme II(A)) giving the secondary amine, 6B. The nitro group may be reduced by, among other reagents, tin (II) chloride dihydrate in EtOAc (60° C.) giving after work-up the aniline, 6C. The aniline may be functionalized to the guanidino group by reaction with amidino pyrazine, to give 6D-1, or otherwise functionalized in similar fashion to Scheme I, to give 6D-2 to 6D-4. Hydrolysis either under standard basic conditions (e.g. LiOH or NaOH/H₂O/dioxane or THF) or by using an appropriate enzyme (e.g. porcine liver esterase in pH 8 buffer) gives the carboxylic acid derivative.
SCHEME V
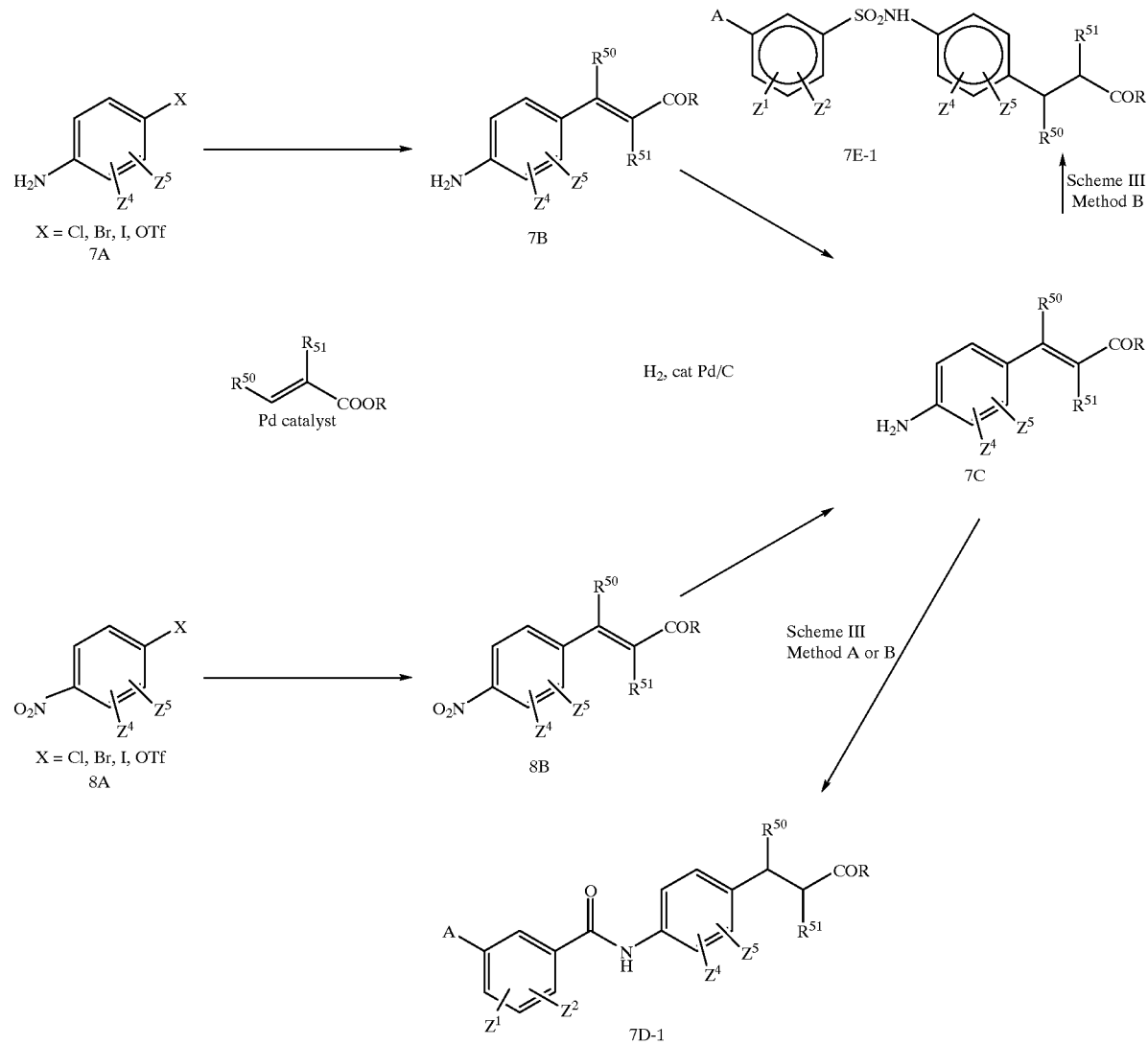
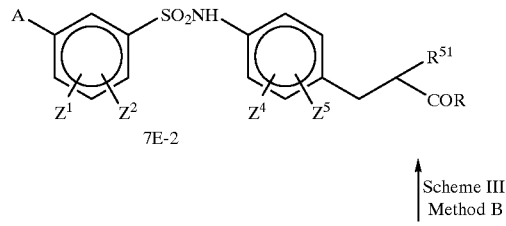

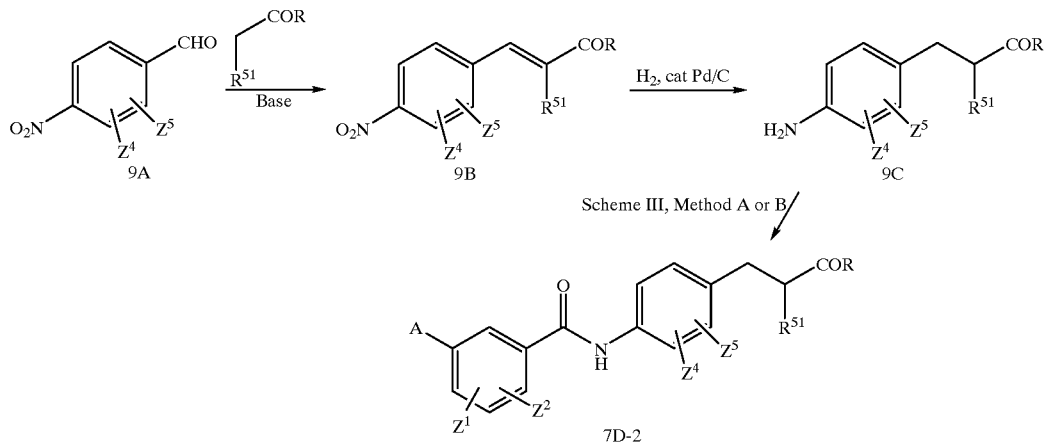

SCHEME VI

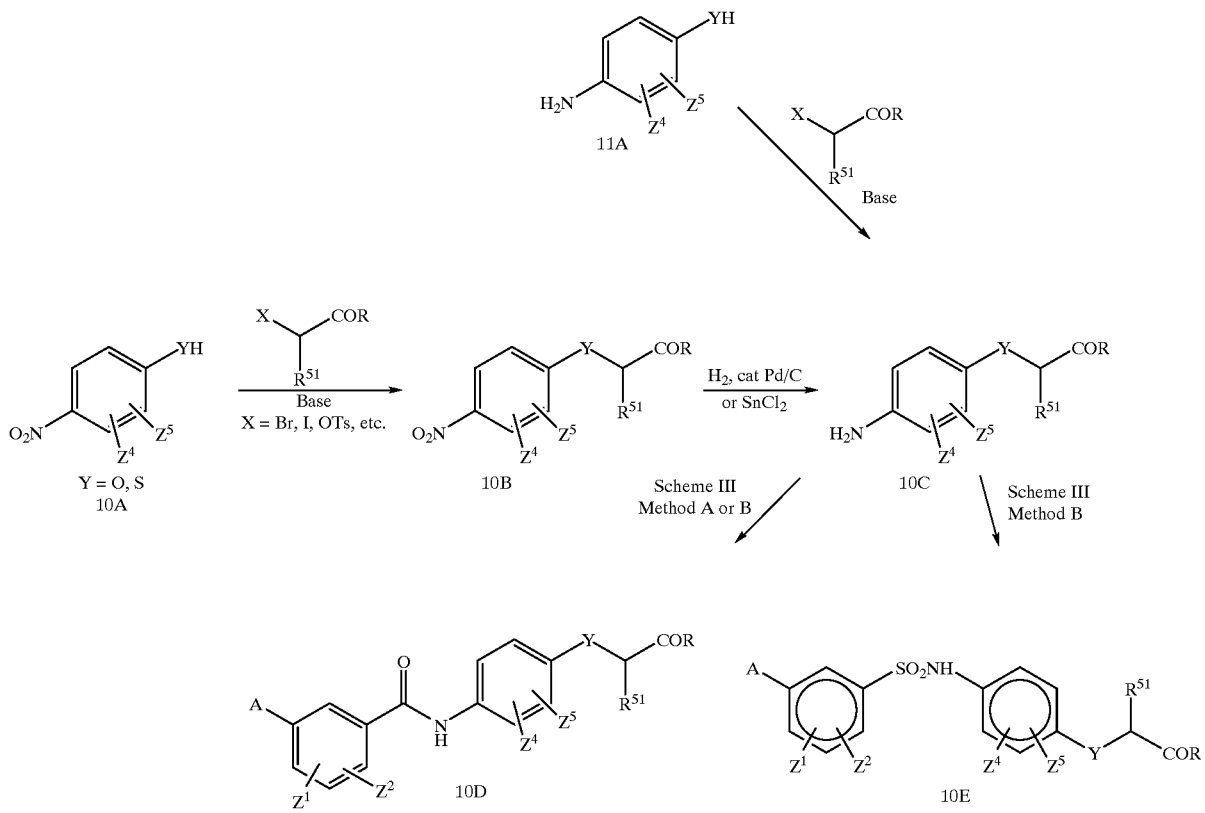

Scheme V outlines methodologies for preparing further phenylpropionic acid derivatives. Palladium catalyzed Heck-type coupling of aryl halides 7A or 8A provided cinnamic acid derivatives 7B and 8B. Reduction ($H_2$, cat. Pd/C) provided phenylpropionic acid derivatives 7C, which were elaborated as shown in Scheme III to furnish 7D-1. Using the analogous sulfonyl chloride in place of the acid chloride provided 7E-1. Alternately, benzaldehydes 9A could be condensed in an aldol-type reaction to give cinnamic acid derivatives 9B, which could be reduced and further elaborated as in Scheme III to give phenylpropionic acid derivatives 7D-2 and 7E-2.

Scheme VI outlines methodologies for preparing phenyoxyacetic acid and thiophenoxyacetic acid derivatives. 4-Nitrophenols or thiophenols 10A were deprotonated (NaH) and alkylated with a-haloacetic acid derivatives to give phenoxyacetic acid derivatives 10B. Reduction of the nitro group ($SnCl_2$ or $H_2$, Pd/C) provided aniline 10C. Alternately, 4-aminophenol or thiophenol 11A could be deprotonated (NaH) and alkylated with α-haloacetic acid derivatives to give phenoxyacetic acid derivatives 10C.

Elaboration as shown in Scheme III gave phenoxyacetic acid derivatives 10D and 10E.

EXAMPLE A

3-Guanidinobenzoic Acid Hydrochloride

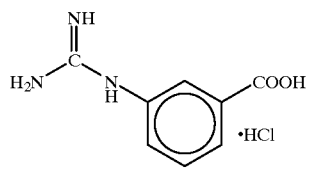

To 3,5-dimethylpyrazole-1-carboxamidine nitrate (6 g, 0.03 mole) (Aldrich) and diisopropylamine (3.8 g, 0.03 mole) in dioxane (20 ml) and H$_2$O (10 ml) was added 3-aminobenzoic acid (2.7 g, 0.02 mole). The reaction was stirred at reflux for 2.5 hours then overnight at room temperature. The resulting precipitate was filtered, washed with dioxane/H$_2$O and dried. The precipitate was then slurried in H$_2$O and acidified with concentrated HCl until a solution formed. The solvent was removed under vacuum and the residue was slurried twice in ether (ether decanted off). The product was dried under vacuum to yield 3-guanidinobenzoic acid hydrochloride (1.77 g) as a white solid. MS and NMR were consistent with the desired structure.

EXAMPLE B 3-(1-Aza-2-amino-1-cycloheptenyl)benzoic Acid Hydrochloride

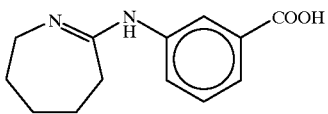

To 1-aza-2-methoxy-1-cycloheptene (3.67 g, 0.0288 mole) (Aldrich) in absolute ethanol (20 ml) was added 3-aminobenzoic acid hydrochloride (5 g, 0.0288 mole). A solution quickly formed. The reaction mixture was stirred overnight at room temperature. The resulting precipitate was filtered, washed with ether and dried under vacuum to yield 3-(1-aza-2-amino-1-cycloheptene)-benzoic acid (4.9 g).

EXAMPLE C 3-(1-aza-2-amino-1-cycloheptenyl)-5-trifluoromethylbenzoic Acid Hydrochloride

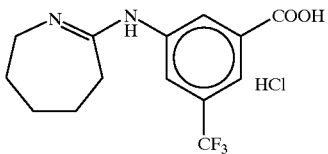

The title compound was synthesized according to the methodology of Example B. substituting an equivalent amount of 3-amino-5-trifluoromethyl benzoic acid [which was synthesized by reduction of 3-nitro-5-trifluoromethyl benzoic acid (Lancaster) in ethanol with 10% Pd/C under 50 psi H$_2$ for 4 hours] for 3-aminobenzoic acid.

EXAMPLE D 3-guanidino-5-trifluoromethylbenzoic Acid, Hydrochloride

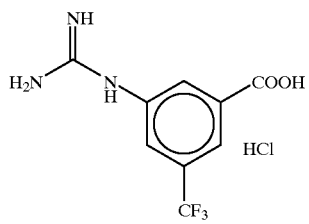

The title compound was synthesized according to the methodology of Example A, substituting an equivalent amount of 3-amino-5-trifluoromethylbenzoic acid (see Example C) for 3-aminobenzoic acid.

EXAMPLE 1

Synthesis of 4-[[[3-[(aminoiminomethyl)amino]-5-(trifluoromethyl)phenyl]carbonyl]amino]-N-[(2-methylpropoxy)carbonyl]phenylalanine, methylester, trifluoroacetate Salt

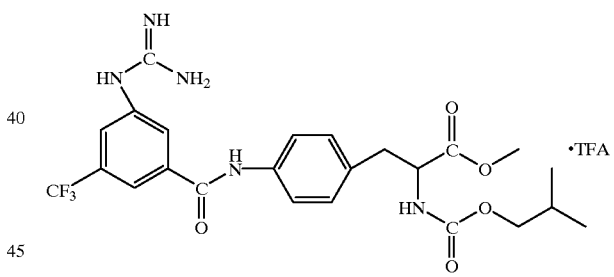

Step A

To p-nitrophenylalanine methyl ester hydrochloride (5 g, 0.019 mole) (Lancaster) in THF (80 mL) and triethylamine (3.88 g, 0.038 mole) was added isobutylchloroformate (2.62 g, 0.019 mole) (Sigma) dropwise at ice bath temperature. The reaction was stirred at room temperature for 3.5 hours. The resulting precipitate was filtered and washed with THF. The solvent from the filtrate was removed under vacuum. The residue was taken up in ethyl acetate. The ethyl acetate portion was worked up with saturated NaHCO$_3$ (1×), H$_2$O (1×), 1N HCl (2×), H$_2$O (2×), dried over MgSO$_4$ and removed under vacuum to yield 5.08 g of p-nitrophenylalanine methyl ester, N-isobutylcarbamate as a yellow solid.

Step B

To the product from Step A (5.08 g) in MeOH (75 mL) was added 10% Pd/C (900 mg) in a Parr bottle. This was then shaken on a Parr shaker under 50 psi H₂ at room temperature for 4.5 hours. The catalyst was filtered through celite, the solvent removed under vacuum and the crude product purified by reverse phase preparatory HPLC to yield 4.5 g of p-amino-phenylalanine methyl ester, N-isobutyl carbamate, trifluoroacetate as a hygroscopic yellow solid.

Step C

To the compound of Example D (0.43 g, 0.0015 mole) in anhydrous DMF (8 mL) and NMM (0.15 g, 0.0015 mole) was added isobutylchloroformate (0.2 g, 0.0015 mole) at ice bath temperature. After stirring 5 minutes, the product from Step B (0.61 g, 0.0015 mole) in anhydrous DMF (8 mL) and NMM (0.15 g, 0.0015 mole) was added to the reaction mixture at ice bath temperature. The reaction was then stirred overnight at room temperature. The solvent was removed under vacuum on a 78° C. water bath and the product was isolated by reverse phase preparatory HPLC to yield (after lyophilization) 230 mg of the title compound as a white solid.

MS and NMR were consistent with the desired structure.

EXAMPLE 2

Synthesis of 4-[[[3-[(aminoiminomethyl)amino]-5-(trifluoromethyl)phenyl]carbonyl]amino]-N-[(2-methylpropoxy)carbonyl]phenylalanine, trifluoroacetate Salt

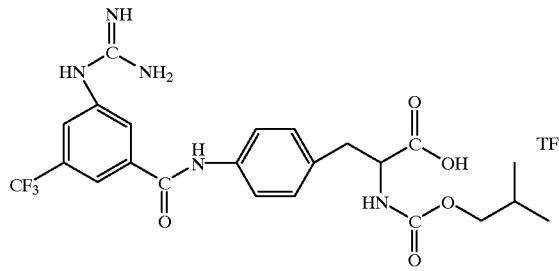

To the compound of Example 1 (200 mg, 0.0003 mole) in H₂O (10 ml) and CH₃CN (10 ml) was added LiOH (53 mg, 0.0013 mole). The reaction was stirred at room temperature for 1.5 hours. The pH was lowered to 2.5 with TFA and the product was isolated by reverse phase preparatory HPLC to yield (after lyophilization) 180 mg of the title compound as a white solid.

MS and NMR were consistent with the desired structure.

EXAMPLE 3

Synthesis of N-[(2-methylpropoxy)carbonyl]-4-[[[3-[(3,4,5,6-tetrahydro-2H-azepin-7-yl)amino]-5-(trifluoromethyl)phenyl]carbonyl]amino]-phenylalanine, methyl Ester, trifluoroacetate Salt

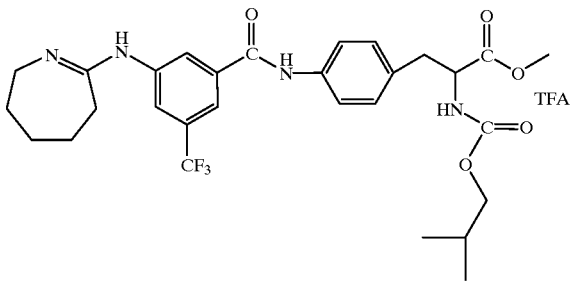

The above compound was prepared according to the methodology of Example 1, substituting an equivalent amount of the compound of Example C for the compound of Example D in Step C.

NMR and MS were consistent with the desired structure.

EXAMPLE 4

Synthesis of N-[(2-methylpropoxy)carbonyl]-4-[[[3-[(3,4,5,6-tetrahydro-2H-azepin-7-yl) amino]-5-(trifluoromethyl)phenyl]carbonyl]amino] phenylalanine, trifluoroacetate Salt

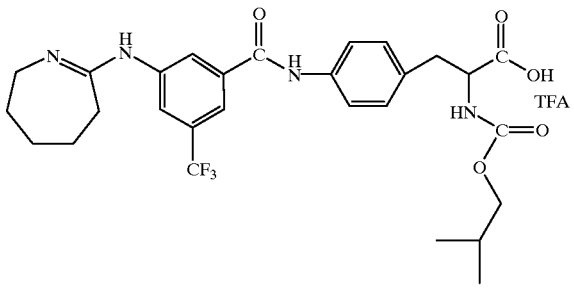

To the product from Example 3 (400 mg, 0.00058 mole) in H₂O (10 ml) and CH₃CN (10 ml) was added LiOH (97 mg, 0.0023 mole). The reaction was stirred at room temperature for 1 hour. The pH was lowered to 2.5 with TFA and the product was isolated by reverse phase preparatory HPLC to yield (after lyophilization) 350 mg of the title compound as a white solid.

MS and NMR were consistent with the desired structure.

EXAMPLE 5

Synthesis of N-(butylsulfonyl)-4-[[[3-[(3,4,5,6-tetrahydro-2H-azepin-7-yl)amino]-5-(trifluoromethyl)phenyl]carbonyl]amino]-phenylalanine, methyl Ester, trifluoroacetate Salt

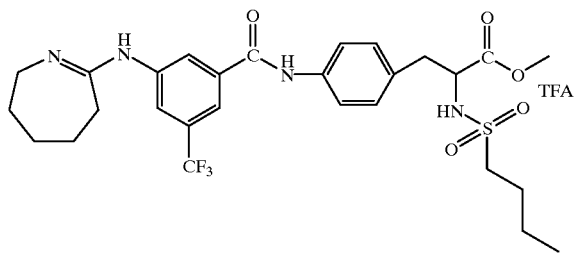

The above compound was prepared according to the methodology of Example 1, substituting an equivalent amount of butanesulfonylchloride for isobutyl chloroformate in Step A and an equivalent amount of the product of Example C for the product of Example D in Step C.

NMR and MS were consistent with the desired structure.

EXAMPLE 6

Synthesis of N-(butylsulfonyl)-4-[[[3-[(3,4,5,6-tetrahydro-2H-azepin-7-yl)-amino]-5-(trifluoromethyl)phenyl]carbonyl]-amino]phenylalanine, trifluoroacetate Salt

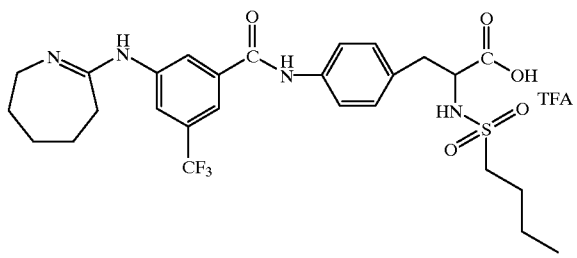

To the product of Example 5 (630 mg, 0.00089 mole) in H₂O (10 ml) CH₃CN (10 ml) was added LiOH (149 mg, 0.0035 mole). The reaction was stirred at room temperature for 3.5 hours. The pH was lowered to 3.5 with TFA and the product was isolated by reverse phase preparatory HPLC to yield (after lyophilization) 560 mg of the title compound as a white solid.

MS and NMR were consistent with the desired structure.

EXAMPLE 7

Synthesis of 4-[[[3-[(aminoiminomethyl)amino]-5-(trifluoromethyl)phenyl]carbonyl]-amino]-N-(butylsulfonyl)phenylalanine, methyl Ester, trifluoroacetate Salt

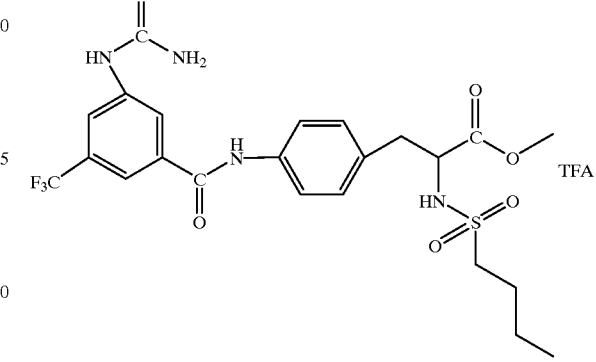

The above compound was prepared according to the methodology of Example 1, substituting an equivalent amount of butanesulfonyl chloride for isobutylchloroformate in Step A.

NMR and MS were consistent with the desired structure.

EXAMPLE 8

Synthesis of 4-[[[3-[(aminoiminomethyl)amino]-5-(trifluoromethyl)phenyl]carbonyl]-amino]-N-(butylsulfonyl)phenylalanine, trifluoroacetate Salt

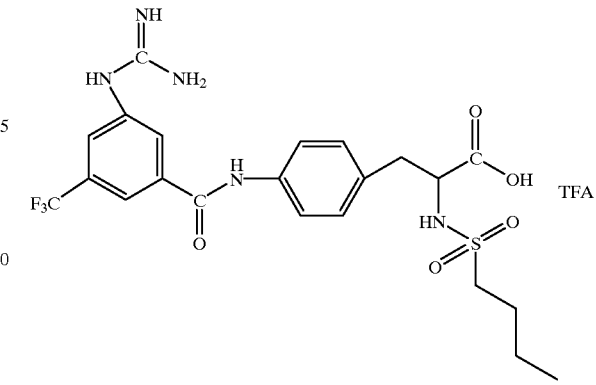

To the product of Example 7 (680 mg, 0.001 mole) in H₂O (10 ml) and CH₃CN (10 ml) was added LiOH (174 mg, 0.004 mole). The reaction was stirred at room temperature for 3 hours. The pH was lowered to 2.5 with TFA and the product was isolated by reverse phase preparatory HPLC to yield (after lyophilization) 590 mg of the title compound as a white solid.

MS and NMR were consistent with the desired structure.

EXAMPLE 9

Synthesis of N-(butylsulfonyl)-4-[[[3-[(3,4,5,6-tetrahydro-2H-azepin-7-yl)amino]-phenyl]carbonyl]amino]phenylalanine, methyl Ester, trifluoroacetate Salt

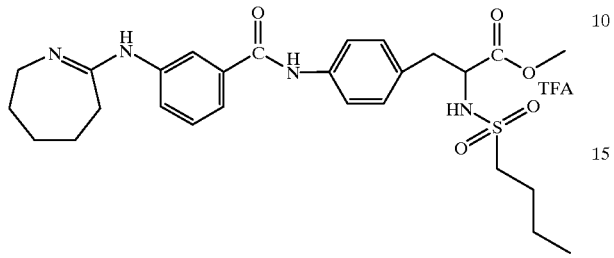

The above compound was prepared according to the methodology of Example 1, substsituting an equivalent amount of butanesulfonyl chloride for isobutylchloroformate in Step A and an equivalent amount of the product of Example B for the product of Example D in Step C.

NMR and MS were consistent with the desired structure.

EXAMPLE 10

Synthesis of N-(butylsulfonyl)-4-[[[3-[(3,4,5,6-tetrahydro-2H-azepin-7-yl)-amino]phenyl]carbonyl]amino]phenylalanine, trifluoroacetate Salt

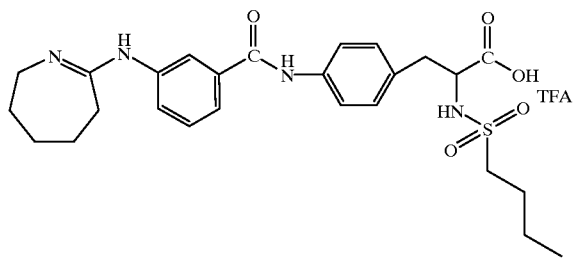

To the product of Example 9 (730 mg, 0.0011 mole) in $H_2O$ (10 ml) and $CH_3CN$ (10 ml) was added LiOH (191 mg, 0.0045 mole). The reaction was stirred at room temperature for 2.5 hours. The pH was lowered to 2.5 with TFA and the product was isolated by reverse phase preparatory HPLC to yield (after lyophilization) 430 mg of the title compound as a white solid.

MS and NMR were consistent with the proposed structure.

EXAMPLE 11

Synthesis of O-[[3-[(aminoiminomethyl)amino]-phenyl]methyl]-N-(butylsulfonyl)tyrosine, trifluoroacetate Salt monohydrate

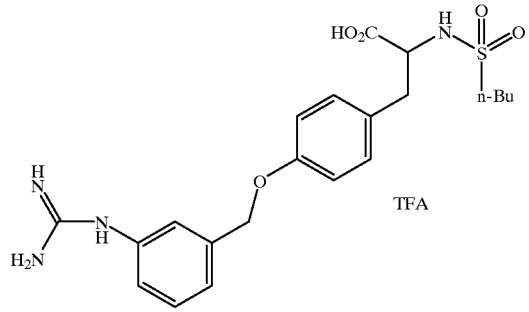

Step A

N-t-Boc-tyrosine ethyl ester (6.0 g, 0.0194 mole) was dissolved in DMF (about 70 mL). To this solution was added, portionwise, potassium hydride (0.86 g, 0.021 mole, hexane washed mineral oil suspension). The reaction mixture was stirred until a solution formed. m-Nitrobenzyl bromide (4.54 g, 0.021 mole) was added and the reaction allowed to proceed over the weekend. Volatiles were removed to give a viscous oil that was taken up in EtOAc/dilute aqueous HCl. The aqueous layer was extracted a second time with EtOAc and the combined organic layers washed with saturated aqueous $NaHCO_3$, dried ($Na_2SO_4$), and volatiles removed to give a golden oil whose NMR and MS were consistent with the desired product.

Step B

The unpurified product from Step A was dissolved in methylene chloride (about 50 mL) and trifluoroacetic acid (20 mL) was added. Stirring was commenced and continued until no further gas evolution was noted (about 0.5 hour). Volatiles were removed until a dark oil was obtained. The oil was treated with EtOAc and dilute aqueous HCl and separated. The organic layer was washed several times with dilute aqueous HCl and the acid layers were combined. The aqueous layer was made basic by addition of solid $NaHCO_3$ and extracted (3x) with EtOAc. The pH was adjusted to about 10 by addition of 2.5 N NaOH and the aqueous layer washed with EtOAc (2x). The combined organic layers from all base washes were combined, dried ($Na_2SO_4$), HCl gas bubbled through (until the solution was saturated) and stripped to give a tan solid (2.16 g) whose NMR and MS were consistent with the desired amino ester hydrochloride salt.

Step C

To the product obtained in Step B (2.16 g, 0.0062 mole), dissolved in THF (100 mL) was added triethylamine (1.38 g, 1.92 mL, 0.00136 mole) and the reaction mixture cooled to 0–5° C. (ice-water/salt bath). N-butanesulfonyl chloride (1.07 g, 0.0068 mole) was added in dropwise fashion. After three hours the volatiles were removed to obtain a dark oil that was worked up in similar fashion to Step A to obtain a product (2.14 g) whose NMR and MS were consistent with the desired sulfonamide ester.

Step D

The product from Step C (2.14 g, 0.0046 mole) was dissolved in absolute EtOH (70 mL) and reduced to the aniline using the procedure of F.D. Bellamy and K. Ou—[Tett. Let., 25, 839–842 (1984)]. Tin (II) chloride dihydrate (5.2 g, 0.023 mole) was added and the mixture heated for one hour at 60° C. The volatiles were removed to obtain a brown foam and EtOAc (100 mL) was added along with saturated aqueous NaHCO$_3$ (200 mL) to produce a fine precipitate. The solution was clarified by passing through a celite pad. The organic layer was separated and the aqueous layer extracted with EtOAc (2×).

The organic layers were combined, dried (Na$_2$SO$_4$) and stripped to give a dark oil (1.75 g) that consisted mostly of desired aniline as confirmed by NMR and mass spectra.

Step E

The crude aniline obtained in Step D was converted to the guanidino—acid in the following manner. Aniline (1.7 g, 0.0042 mole) from Step D was dissolved in dioxane (40 mL). To this was added triethylamine (0.47 mL, 0.0047 mole), pyrazole carboxamidine at (Aldrich, 0.68 g, 0.0047 mole) and water (5 mL) and the reaction mixture heated to reflux. Partial conversion to product was noted after refluxing overnight. More carboxamidine was added (0.4 g) and refluxing continued. After several hours the reaction mixture was cooled and the pH adjusted to 11 by addition of dilute aqueous LiOH. The reaction was maintained at pH 11 for several hours until most of the ester had hydrolyzed. The reaction mixture was made acidic by addition of TFA and the desired guanidino acid isolated by preparatory rphplc. The appropriate fractions were combined and lyophilized to obtain a hydroscopic powder (0.25 g) that was determined to be the desired compound by NMR and MS.

EXAMPLE E

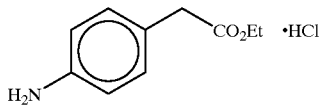

4-Aminophenylacetic acid (3 g, 19.8 mmol) was dissolved in dry ethanol (60 mL) at 0° C. and a stream of hydrogen chloride gas was bubbled into the solution for 15 minutes. The solvent was removed under reduced pressure to give desired product.

EXAMPLE F

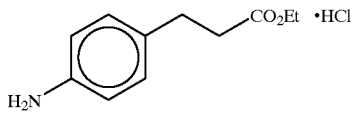

The above compound was prepared under conditions similar to Example E, replacing 4-aminophenylacetic acid with p-aminohydrocinnamic acid.

EXAMPLE BF

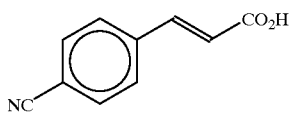

A mixture of p-cyanobenzaldehyde (5.025 g, 38 mmol), malonic acid (4.407 g, 42 mmol), and pyridine (0.50 mL, 6.5 mmol) in absolute ethanol (10 mL) was heated to 100° C. (bath) under argon. Upon heating, the mixture became a solution; and after 20–30 minutes, a yellow precipitate crashed out of solution. The reaction was monitored by TLC (10% MeOH/CH$_2$Cl$_2$). After 21.5 hours, the reaction mixture was allowed to cool to room temperature and the yellow precipitate collected by vacuum filtration. The solid was slurried with hot EtOH and collected by filtration to give the desired product as a yellow solid (4.77 g, 73% yield). NMR was consistent with proposed structure.

EXAMPLE BG

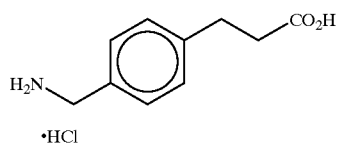

The compound of Example BF (2.038 g, 11.7 mmol) was dissolved in a MeOH (15 mL)/NH$_4$OH (7.5 mL) mixture and hydrogenated with W-2 Raney Ni in a Parr Shaker (60 psi, 25° C.) for 2.5 hours. The catalyst was filtered off and the purple filtrate concentrated in vacuo. The green solid residue was dissolved in 1 M HCl and concentrated in vacuo to give a white/green solid. The solid was purified by slurrying with 9:1 CH$_3$CN/MeOH mixture. The white solid was collected by vacuum filtration to give the desired product (0.824 g, 33% yield). NMR was consistent with proposed structure.

EXAMPLE BH

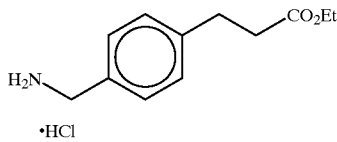

A mixture of the compound in Example BG (0.824 g) in absolute EtOH (50 mL) was cooled to 0° C. and HCl (g) was bubbled into it for 20 minutes. The resulting green/blue solution was allowed to stir for 2 hours. An aliquot was removed and concentrated in vacuo. $^1$H NMR showed the reaction to be complete. The reaction was concentrated in vacuo to give a slightly green-tinted white solid (0.841 g). NMR was consistent with proposed structure.

EXAMPLE 12

Synthesis of ethyl 4-[[[[3-(cyano)phenyl]-carbonyl]amino]methyl]benzenepropanoate

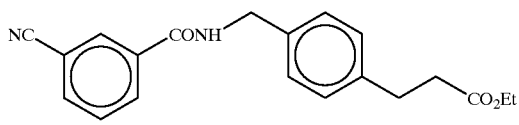

A solution of 3-cyanobenzoic acid (0.447 g, 3.0 mmol) and 1-methyl piperidine (0.37 mL, 3.0 mmol) in $CH_2Cl_2$ (15 mL) was cooled to 0° C. Isobutylchloroformate (0.39 mL, 3.0 mmol) was added slowly under argon and the reaction stirred for another 5 minutes. A solution of the compound of Example BH (0.705 g, 2.9 mmol) and 1-methyl piperidine (0.37 mL, 3.0 mmol) in $CH_2Cl_2$ (3 mL) was then added and the ice bath immediately removed. The reaction was allowed to stir at room temperature for 2 hours. The reaction was concentrated in vacuo to give a green solid residue. The residue was partitioned between EtOAc (25 mL) and water (25 mL). The organic layer was collected, washed with 1M HCl (1×25 mL), saturated $NaHCO_3$ (1×25 mL), and brine (1×25 mL), and then dried over $MgSO_4$. Concentration in vacuo gave the crude product as a pale yellow oil (1.17 g). The product was purified by column chromatography (50 g silica gel, 2% $MeOH/CH_2Cl_2$) to give a yellow\white solid (0.476 g, 44% yield). NMR was consistent with the proposed structure.

EXAMPLE G

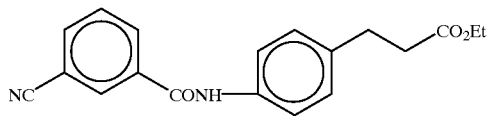

The above compound was synthesized under conditions similar to Example 12, replacing the compound of Example BH with the compound of Example F.

Analysis Calculated for $C_{19}H_{18}N_2O_3$: C, 70.79; H, 5.63; N, 8.69. Found: C, 70.49; H, 5.65; N, 8.62.

EXAMPLE 13

Ethyl 4-[[[[3-[amino(hydroxyimino)methyl]-phenyl]carbonyl]amino]methyl)benzenepropanoate

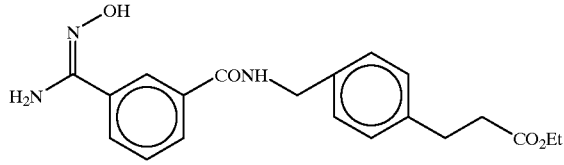

A solution of the compound of Example 12 (0.476 g, 1.3 mmol), hydroxylamine hydrochloride (0.089 g, 1.3 mmol), and triethylamine (0.18 mL, 1.3 mmol) in absolute EtOH (10 mL) was heated to reflux (86–90° C.). After 5 hours, TLC [1:1 EtOAc/hexane (10 mL)+5 drops of AcOH] showed that starting material was still present. Additional hydroxylamine hydrochloride (0.04 g, 0.6 equivalent) and triethylamine (0.09 mL) was added. After 40 minutes, the TLC showed no change. The reaction was concentrated in vacuo and the residue was dissolved in $H_2O$ (30 mL). The aqueous layer was extracted with EtOAc (40 mL). The organic layer was collected, dried over $MgSO_4$, and concentrated in vacuo to give a white solid (0.49 g). NMR was consistent with the proposed structure.

EXAMPLE 14

Ethyl 4-[[[3-[amino(hydroxyimino)methyl]phenyl]-carbonyl]amino]benzenepropanoate

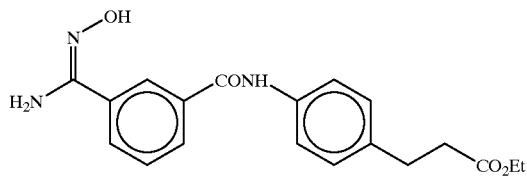

The above compound was synthesized under conditions similar to Example 13, replacing the compound of Example 12 with the compound of Example G.

EXAMPLE 15

Ethyl 4-[[[[3-(aminoiminomethyl)phenyl]-carbonyl]amino]methyl]benzenepropanoate

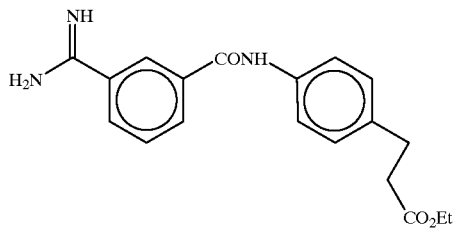

The compound of Example 13 (0.49 g, 1.3 mmol) was dissolved in ACOH and hydrogenated with 4% Pd/C (53% wet, 0.050 g) in a Parr Shaker (60 psi, 60C). The catalyst was filtered off and the filtrate concentrated in vacuo to give a white solid. The solid was slurried with acetonitrile and the resulting white solid was collected by vacuum filtration (0.423 g). Analysis Calculated for $C_{20}H_{23}N_3O_3 \cdot 1.6$ AcOH: C, 61.99; H, 6.59; N, 9.35. Found: C, 61.81; H, 6.50; N, 9.42. M+=353.

EXAMPLE 17

Ethyl 4-[[[3-(aminoiminomethyl)phenyl]-carbonyl]amino]benzenepropanoate

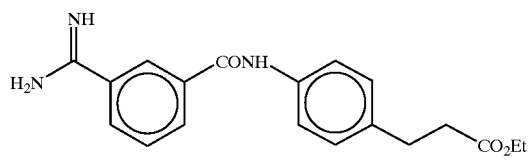

The compound of Example 14 was reduced under conditions similar to the conditions described in Example 15, replacing the compound of Example 13 with the compound of Example 14.

Analysis Calculated for $C_{19}H_{31}N_3O_3 \cdot 1.7$ AcOH: C, 60.94; H, 6.35; N, 9.52. Found: C, 61.02; H, 6.38; N, 9.12.

EXAMPLE 19

Synthesis of 4-[[[3-(aminoiminomethyl)phenyl]carbonyl]amino]methyl]benzenepropanoic acid, trifluoroacetate Salt

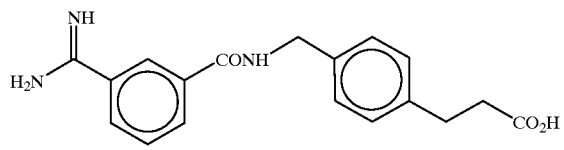

To a mixture of the compound of Example 15 (0.200 g, 0.57 mmol) in 1 M phosphate buffer (8 mL) was added esterase from porcine liver (Sigma, 0.5 mL) at room temperature. The reaction was stirred for 18 hours and then concentrated in vacuo. A solution of 1 M HCl (3 mL)/$CH_3CN$ (3 mL) was added to the resulting residue and the undissolved solid filtered off. The filtrate was collected, concentrated in vacuo, and purified by HPLC-Method 1 to give the desired product as a white solid (0.17 g).

Analysis Calculated for $C_{18}H_{19}N_3O_3 \cdot 1.0$ TFA+0.1 $H_2O$: C, 54.45; H, 4.61; N, 9.52. Found: C, 54.47; H, 4.53; N, 9.52. MH+=326.

EXAMPLE 20

4-[[[3-(Aminoiminomethyl)phenyl]carbonyl]-amino]benzenepropanoic Acid

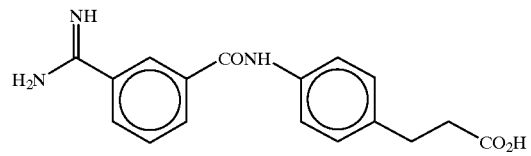

The above compound was synthesized under conditions similar to the conditions described in Example 19 replacing the compound of Example 15 with the compound of Example 17.

Analysis Calculated for $C_{17}H_{17}N_3O_3 \cdot 1$TFA: C, 53.65; H, 4.27; N, 9.88. Found: C, 53.41; H, 4.17; N, 9.56.

EXAMPLE GA

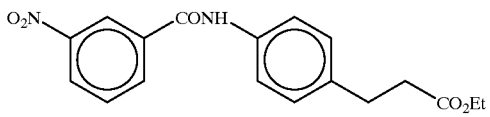

A solution of 3-nitrobenzoic acid (0.5 g, 3 mmol) and 1-methyl piperidine (0.37 mL, 3 mmol) in $CH_2Cl_2$ (15 mL) was cooled to 0° C. and isobutyl chloroformate (0.4 mL, 3 mmol) was added under argon. The reaction was allowed to stir for 5 minutes before adding a mixture of the compound of Example F (0.687 g, 3 mmol) and 1-methyl piperidine (0.37 mL, 3 mmol) in $CH_2Cl_2$ (3 mL). The ice bath was removed and the reaction was allowed to stir at room temperature over 24 hours. The reaction was concentrated in vacuo and the residue was purified by column chromatography (300 g silica gel, 1% MeOH/$CH_2Cl_2$) to give the desired product as a yellow solid.

Analysis Calculated for $C_{18}H_{18}N_2O_5$: C, 63.15; H, 5.30; N, 8.18. Found: C, 63.14; H, 5.41; N, 8.13.

EXAMPLE H

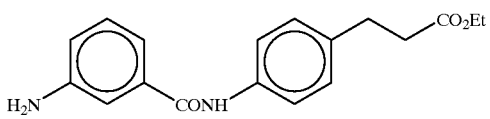

The compound of Example GA (1 g, 2.9 mmol) was hydrogenated (4% Pd/C, EtOH-THF, 5 psi, room temperature, 1.5 hours) and the filtrate concentrated in vacuo to give a yellow oil (0.8 g, 88% yield). NMR was consistent with the proposed structure.

EXAMPLE 22

Ethyl 4-[[[3-[(aminocarbonyl)amino]phenyl]-carbonyl]amino]benzenepropanoate

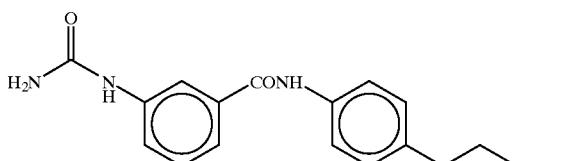

A mixture of the compound of Example H (480 mg, 1.54 mmol) and acetic acid (1 mL) in water (2 mL) was heated to 38° C. (bath). A solution of potassium cyanate (250 mg, 3.08 mmol) in water (2 mL) was then added slowly. The reaction became cloudy and a white precipitate resulted. The reaction was allowed to cool to room temperature and stirred for 1.5 hours. The reaction was monitored by TLC (10% MeOH/$CH_2Cl_2$). The white solid was collected by vacuum filtration and washed with water (0.469 g, 58% yield). The product was purified by column chromatography (10% MeOH/$CH_2Cl_2$) to give 150 mg desired compound.

Analysis Calculated for $C_{19}H_{21}N_3O_4$+0.1 $H_2O$: C, 63.89; H, 5.98; N, 11.76. Found: C, 63.66; H, 5.52; N, 11.56.

EXAMPLE 24

Synthesis of 4-[[[3-[(aminocarbonyl)amino]phenyl]carbonyl]amino]benzenepropanoic Acid

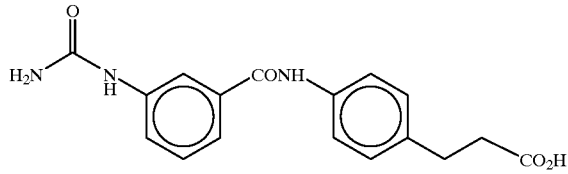

The Compound of Example 22 (0.12 g, 0.34 mmol) was dissolved in MeOH (2 mL) and 1 M LiOH (1 mL) was added. The reaction was stirred at room temperature over 16 hours. The reaction was concentrated in vacuo to give a white solid. The solid was dissolved in a small amount of $H_2O$ and acidified with 1 drop of TFA. The mixture was concentrated in vacuo and the residue was purified by HPLC—Method 1 to give a white solid (0.06 g,).

Analysis Calculated for $C_{17}H_{17}N_3O$: C, 62.38; H, 5.24; N, 12.84. Found: C, 62.00; H, 5.53; N, 12.75.

EXAMPLE 26

Synthesis of ethyl 4-[[[3-[[[((phenylmethyl)amino]carbonyl]amino]phenyl]carbonyl]amino]benzenepropanoate

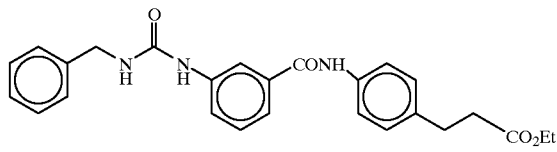

To a solution of benzyl isocyanate (0.146 g, 1.1 mmol) in $CH_2Cl_2$ (6 mL) was added a solution of the compound of Example H (0.36 g, 1.15 mmol) in $CH_2Cl_2$ (2 mL) under argon. The flask containing the compound of Example H was rinsed with $CH_2Cl_2$ (1 mL) and added to the reaction. The reaction was stirred at room temperature for 72 hours. The reaction was concentrated in vacuo and ether added to the yellow oil. Upon addition, the oil solidified. The resulting white solid was collected by vacuum filtration and washed with a small amount of ether (0.3 g).

Analysis Calculated for $C_{26}H_{27}N_3O_4$: C, 70.10; H, 6.11; N, 9.43. Found: C, 70.12; H, 6.35; N, 9.45.

EXAMPLE 28

Synthesis of 4-[[[3-[[[(phenylmethyl)amino]carbonyl]amino]phenyl]carbonyl]amino]benzenepropanoic Acid

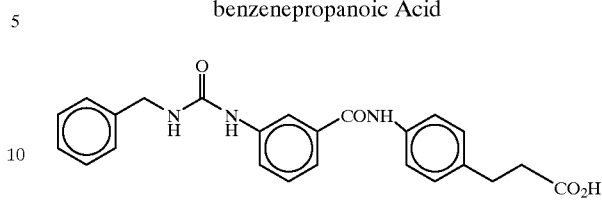

The compound of Example 26 was hydrolyzed under conditions similar to the conditions described in Example 24 to provide the title compound. Analysis Calculated for $C_{24}H_{23}N_3O_4 \cdot 0.6 H_2O$: C, 67.31; H, 5.70; N, 9.81. Found: C, 67.24; H, 5.35; N, 9.80.

EXAMPLE 29

4-[[[[3-[(aminoiminomethyl)amino]phenyl]carbonyl]amino]methyl]benzenepropanoic Acid, trifluoroacetate Salt

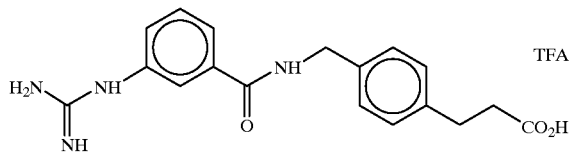

A solution of the compound of Example A (0.216 g, 1.0 mmol) and 1-methyl piperidine (0.12 mL, 1.0 mmol) in DMF (5 mL) was cooled to 0° C. and isobutyl chloroformate (0.13 mL, 1.0 mmol) was added under argon. The reaction was allowed to stir for 5 minutes before adding a mixture of the compound of Example BG (0.216 g, 1.0 mmol) and 1-methyl piperidine (0.12 mL, 1.0 mmol) in DMF (2 mL). The flask containing the compound of Example BG was rinsed with DMF (1 mL) and the rinse added to the reaction. The ice bath was removed after addition and the reaction was allowed to stir at room temperature over 24 hours. The reaction was concentrated in vacuo and the residue purified by HPLC-Method 1 to give the desired product as a white solid (0.051 g).

Analysis Calculated for $C_{18}H_{20}N_4O_3 \cdot 0.3 H_2O$: C, 52.24; H, 4.73; H, 12.18. Found: C, 52.35; H, 4.64; N, 12.21. MH+=341.

EXAMPLE J

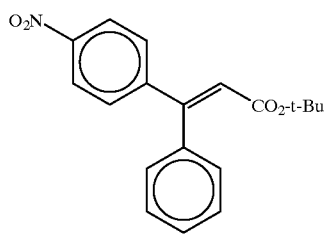

A suspension of 60% NaH in mineral oil (washed with hexane before use, 0.54 g, 13.5 mmol) in distilled THF (15 mL) was cooled to 0C and t-butyl P,P-dimethylphospononacetate (2.7 mL, 13.5 mmol) was added very slowly under argon. Vigorous bubbling was observed and the reaction became a white slurry. The reaction was allowed to stir at 0° C. for 1.5 hours before adding a solution of 4-nitrobenzophenone (3.073 g, 13.2 mmol) in THF (15 mL). The flask containing 4-nitrobenzophenone was rinsed with THF (5 mL) and the solution added to the reaction. The reaction was allowed to warm to room temperature. After 2 hours, the reaction was quenched with water (25 mL) and extracted with EtOAc (2×25 mL). The organic layers were collected, dried over MgSO₄, and concentrated in vacuo to give a pale yellow solid (4.87 g). The crude material was purified by column chromatography (150 g silica gel, 5% EtOAc/hexane) and one isomer was isolated as a white solid (1.97 g). NMR was consistent with proposed structure.

EXAMPLE K

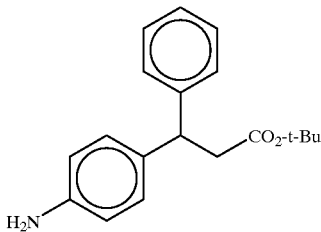

The compound of Example J (1.97 g, 6.15 mmol) was hydrogenated (EtOH/THF, 4% Pd/C, 5 psi, room temperature, 24 hours) and the filtrate concentrated in vacuo. The residue was purified by column chromatography (70 g silica, 1:1 hexane/EtOAc) to give the desired product as a white solid (1.51 g, 83% yield). NMR was consistent with the proposed structure.

EXAMPLE L

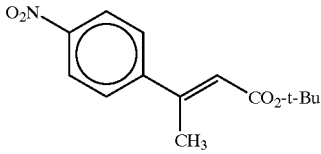

4-Nitroacetophenone (1.45 g, 8.8 mmol) was treated with t-butyl P,P-dimethylphosphonoacetate (2 g, 9 mmol) under similar conditions to the conditions described in Example J. The crude compound was chromatographed on silica gel using 10% EtOAc/Hex as eluant to give 700 mg of pure desired compound.

Analysis Calculated for $C_{14}H_{17}NO_4$: C, 63.87; H, 6.51; N, 5.32. Found: C, 63.79; H, 6.21; N, 5.16.

EXAMPLE M

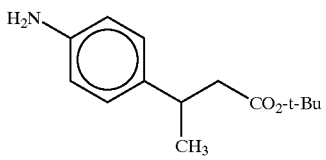

The compound of Example L was hydrogenated (EtOH/THF, 4% Pd/C, 5 psi, room temperature, 1 hour) and the filtrate concentrated in vacuo to afford 600 mg of the desired compound as brown oil.

EXAMPLE 30

Synthesis of 1,1-dimethylethyl 4-[[[3-[(aminoiminomethyl)amino]phenyl]carbonyl]amino]-β-methylbenzenepropanoate, trifluoroacetate Salt

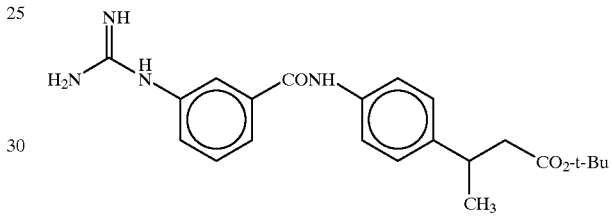

The compound of Example M was coupled with the compound of Example A under similar reaction conditions as described in Example 34.

Analysis Calculated for $C_{22}H_{28}N_4O_3 \cdot 1.5$ TFA·1.1 $H_2O$: C, 51.12; H, 5.44; N, 9.54. Found: C, 51.12; H, 5.05; N, 9.59.

EXAMPLE 31

Synthesis of 4-[[[3-[(aminoiminomethyl)amino]phenyl]carbonyl]amino]-β-methylbenzenepropanoic Acid, trifluoroacetate Salt

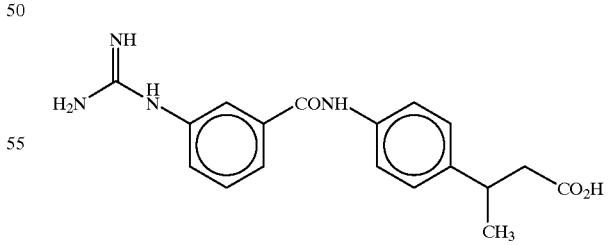

The compound of Example 30 was hydrolyzed with TFA under conditions similar to those described in Example 33.

Analysis Calculated for $C_{18}H_{20}N_4O_3 \cdot 1.2$ TFA+0.8 $H_2O$: C, 49.84; H, 4.67; N, 11.40. Found: C, 49.99; H, 4.33; N, 11.44.

EXAMPLE 32

1,1-Dimethylethyl 4-[[[3-[(aminoiminomethyl)-amino]phenyl]carbonyl]amino]β-phenyl benzenepropanoate

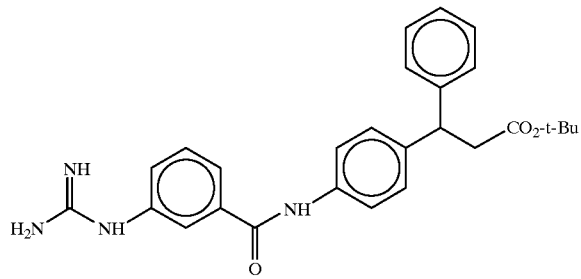

The compound of Example K (0.511 g, 1.7 mmol) was coupled with the compound of Example A under the same reaction conditions as described in Example 34. The crude material was purified by HPLC-Method 1 to give the desired product as a pale yellow oil (0.270 g, 35% yield).

Analysis Calculated for $C_{27}H_{30}N_4O_3 \cdot 1.1$ TFA+1.0 $H_2O$: C, 58.26; H, 5.54; N, 9.31. Found: C, 58.00; H, 5.19; N, 9.67. M+=458.

EXAMPLE 33

Synthesis of 4-[[[3-[(aminoiminomethyl)amino]phenyl]carbonyl]amino]-β-phenylbenzenepropanoic Acid, trifluoroacetate Salt

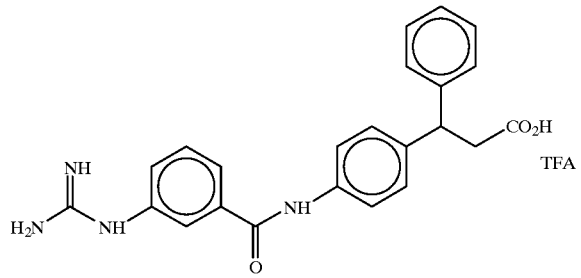

A solution of the compound of Example 32 (0.23 g) in $CH_2Cl_2$ (4 mL) was cooled to 0° C. and TFA (3 mL) was added under argon. The ice bath was removed and the reaction allowed to warm to room temperature. The reaction was stirred for 4.5 hours, then concentrated under a stream of $H_2$. The residue was purified by HPLC-Method 1 to give the desired product as a white solid (0.085 g).

Analysis Calculated for $C_{23}H_{22}N_4O_3 \cdot 1.0$ TFA+0.5 $H_2O$: C, 57.14; H, 4.60; N, 10.66. Found: C, 57.27; H, 4.65; N, 10.69. MH+=403.

EXAMPLE N

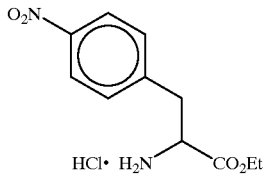

4-Nitro-DL-phenylalanine (5 g, 23.8 mmol) was suspended in dry ethanol (80 mL) at 0° C. and a stream of hydrogen chloride gas was bubbled into the solution for 10 minutes. The mixture was then refluxed overnight. The reaction was cooled to room temperature and the solvent removed under reduced pressure to give 6.3 g of the desired compound as white solid.

EXAMPLE O

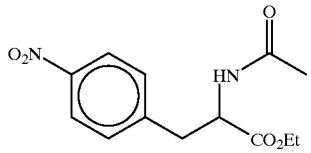

4-Nitro-DL-phenylalanine hydrochloride ethyl ester as prepared in Example N (1.5 g, 5.5 mmol) was dissolved in methylene chloride (30 mL) and cooled to 0° C. To this was added acetyl chloride (475 mg, 6 mmol) and trimethylamine (1.7 mL, 12 mmol). The reaction mixture was warmed to room temperature and stirred overnight. The solvent was removed under reduced pressure. Water was added and the solution was extracted with ethyl acetate. The combined organic layers were washed with brine, dried over $Na_2SO_4$, filtered and concentrated in vacuo to give 1.5 g of the desired compound as white solid.

EXAMPLE P

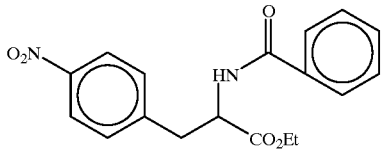

The above compound was prepared in the same manner as described in Example O, replacing acetyl chloride with benzoyl chloride. The residue was chromatographed on silica gel using EtOAc/Heptane (20/80) as eluant to give 1.7 g of the desired compound as yellow solid.

EXAMPLE Q

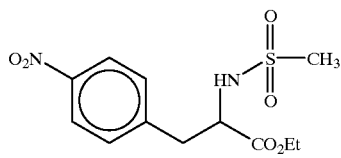

The above compound was prepared in the same manner as described in Example Q, replacing acetyl chloride with methane sulfonylchloride. The residue was chromatographed on silica gel using EtOAc/Heptane (50/50) as eluant to give 1.2 g of the desired compound as a white solid.

EXAMPLE R

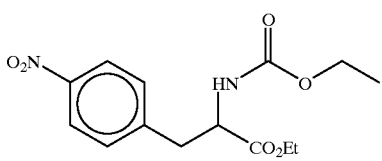

The above compound was prepared in the same manner as described in Example O replacing acetyl chloride with ethyl chloroformate. The residue was chromatographed on silica gel using EtOAc/Heptane (50/50) as eluant to give 600 mg of the desired compound as yellow oil.

EXAMPLE S

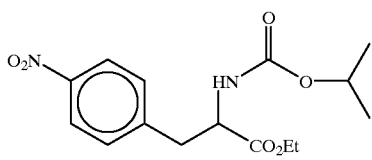

The above compound was prepared in the same manner as described in Example O, replacing acetyl chloride with isopropyl chloroformate. The residue was chromatographed on silica gel using EtOAc/Heptane (50/50) as eluant to give 600 mg of the desired compound.

EXAMPLE T

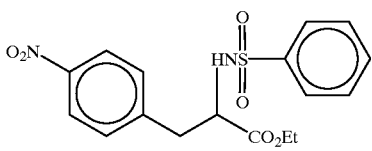

The above compound was prepared in the same manner as described in Example O, replacing acetyl chloride with benzenesulfonylchloride. The residue was chromatographed on silica gel using EtOAc/Hexane (50/50) as eluant to give 1.3 g of the desired compound as white solid.

EXAMPLE U

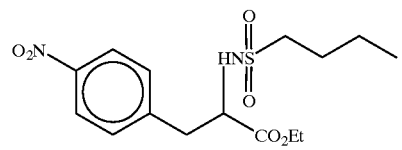

The above compound was prepared in the same manner as described in Example O, replacing acetyl chloride with 1-butanesulfonyl chloride. The residue was chromatographed on silica gel using EtOAc/Heptane (50/50) as eluant to give 900 mg of the desired compound.

EXAMPLE V

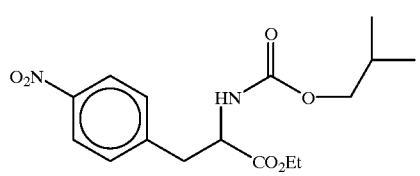

The above compound was prepared in the same manner as described in Example O, replacing acetyl chloride with isobutyl chloroformate. The residue was chromatographed on silica gel using EtOAc/Heptane (50/50) as eluant to give 1.1 g of the desired compound.

EXAMPLE W

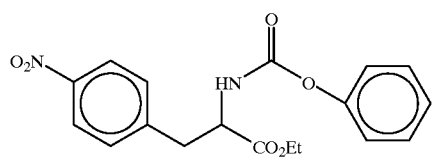

The above compound was prepared in the same manner as described in Example O, replacing acetyl chloride with phenyl chloroformate. The residue was chromatographed on silica gel using EtOAc/Heptane (50/5) as eluant to give 1.1 g of the desired compound.

EXAMPLE X

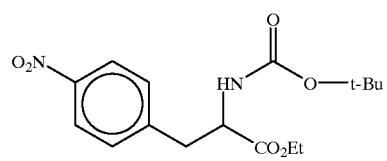

A mixture of the compound of Example N (1.5 g 5.5 mmol), di-tert-butyl dicarbonate (1.32 g, 6 mmol) and potassium carbonate (2.3 g, 16.5 mmol) in THF/H$_2$O (1:1, 20 mL) was stirred at room temperature overnight. The solution was concentrated and the residue was dissolved in ethyl acetate. The solution was treated with water, and extracted with ethyl ether. The combined organic phases were washed with brine, dried over Na$_2$SO$_4$ and evaporated to afford 1.8 g yellow solid.

EXAMPLE Y

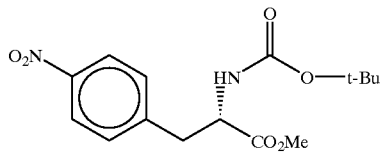

A mixture of (S)-4-nitrophenylalanine methyl ester hydrochloride (1.43 g, 5.5 mmol), di-tert-butyl dicarbonate (1.3 g, 6 mmol) and potassium carbonate (2.3 g, 16.5 mmol) in THF/H$_2$O (1:1, 20 mL) was stirred at room temperature overnight. The solution was concentrated and the residue was dissolved in ethyl acetate. The solution was treated with water, and extracted with ethyl ether. The combined organic phases were washed with brine, dried over Na$_2$SO$_4$ and evaporated to afford 1.8 g yellow solid.

EXAMPLE Z

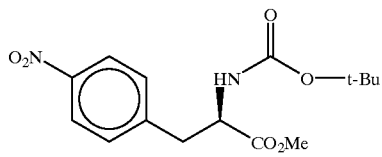

N-Boc-p-nitro-D-phenylalanine (1 g, 3.2 mmol, Bachem) was treated with ethereal CH$_2$N$_2$ solution (15 mL), (prepared from 1.65 g N-nitroso-N-methyl urea) at 0° C. The reaction mixture was warmed to room temperature and stirred for 3 hours. The solvent was removed under reduced pressure to give 1.1 g title compound as white solid.

EXAMPLE AA

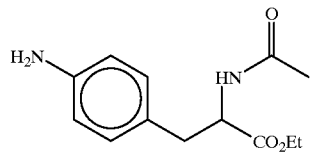

The product of Example O (1.5 g, 5.3 mmol) was dissolved in EtOH/THF and transferred to a Parr Shaker containing a catalytic amount of 4% Pd/C. The reaction was shaken for 16 hours at room temperature under 5 psi pressure of H$_2$. The reaction mixture was filtered and concentrated to afford 1.2 g of a brown solid.

The following compounds were prepared in the same manner as described in Example AA.

EXAMPLE AB

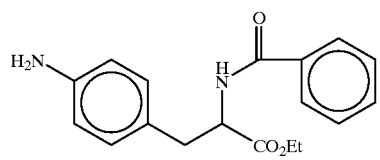

EXAMPLE AC

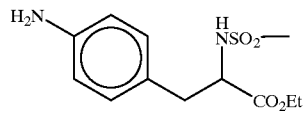

EXAMPLE AD

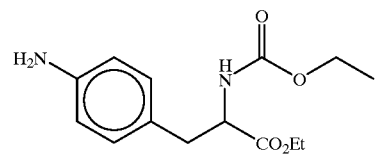

EXAMPLE AE

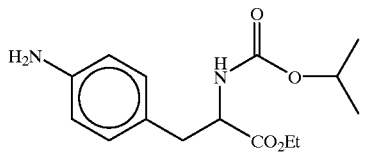

EXAMPLE AF

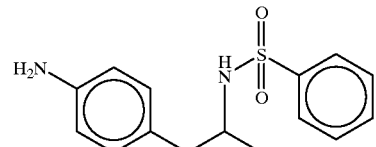

EXAMPLE AG

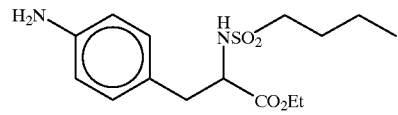

EXAMPLE AH

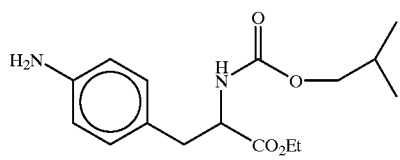

EXAMPLE AI

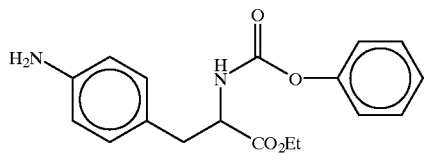

EXAMPLE AJ

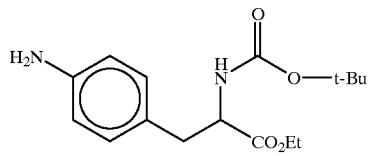

EXAMPLE AK

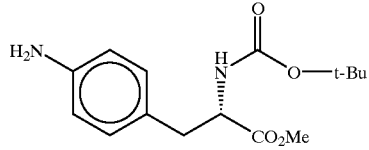

EXAMPLE AL

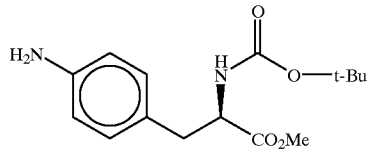

EXAMPLE 34

Synthesis of N-acetyl-4-[[[3-[(aminoiminomethyl) amino]phenyl)carbonyl]amino]phenylalanine Ethyl Ester, trifluoroacetate Salt

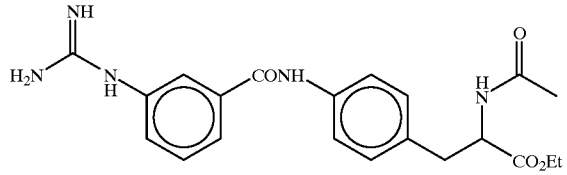

To a stirred solution of the compound of Example A (517 mg, 2.4 mmol) in dimethyl formamide (10 mL) at 0° C. was added 1-methylpiperidine (238 mg, 2.4 mmol) followed by the addition of isobutyl chloroformate (328 mg, 2.4 mmol). After 5 minutes the compound of Example AA (600 mg, 2.4 mmol) in dimethyl formamide (1 mL) was introduced. The reaction mixture was warmed to room temperature and stirred overnight. The solvent was removed under reduced pressure, and the residue was purified by reverse phase HPLC-Method 1 to give 600 mg white solid. Analysis Calculated for $C_{21}H_{25}N_5O_4 \cdot 1.6TFA \cdot 0.8\ H_2O$: C, 47.78; H, 4.67; N, 11.51. Found: C, 47.54; H, 4.67; N, 11.86.

EXAMPLE 35

Synthesis of N-acetyl-4-[[[3-[(aminoiminomethyl) amino]-phenyl]carbonyl]amino]phenylalanine, trifluoroacetate Salt

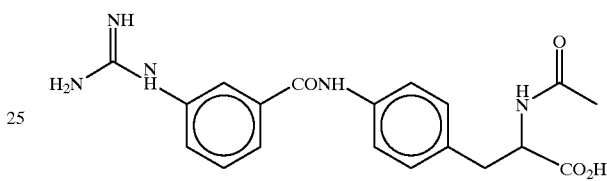

The product of Example 34 (420 mg, 1 mmol) was dissolved in methanol (4 mL) at room temperature. Lithium hydroxide (1M, 2 mL) was added and the reaction mixture was stirred overnight. The solution was concentrated and purified by reverse phase HPLC-Method 1 to give 120 mg white solid.

Analysis Calculated for $C_{19}H_{21}N_5O_4 \cdot 1.6TFA \cdot 0.6\ H_2O$: C, 46.24; H, 4.16; N, 12.14. Found: C, 46.41; H, 4.15; N 11.83.

EXAMPLE 36

Synthesis of 4-[[[3-[(aminoiminomethyl)amino] phenyl]-carbonyl]amino]-N-(phenylcarbonyl) phenylalanine Ethyl Ester, monohydrate trifluoroacetate Salt

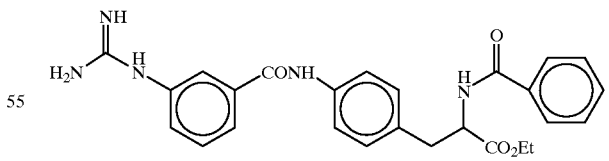

The title compound was prepared in the same manner as described in Example 34, replacing the compound of Example AA with the compound of Example AB.

Analysis Calculated for $C_{26}H_{27}N_5O_4 \cdot 1.1\ TFA \cdot 1\ H_2O$: C, 54.90; H, 4.92; N, 11.35. Found: C, 54.82; H, 4.60; N, 11.51.

EXAMPLE 37

Synthesis of 4-[[[3-[(aminoiminomethyl)amino]phenyl]carbonyl]amino]-N-(methylsulfonyl)phenylalanine Ethyl Ester, monohydrate trifluoroacetate Salt

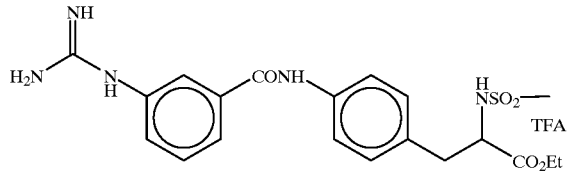

The title compound was prepared in the same manner as described in Example 34, replacing the compound of Example AA with the compound of Example AC.

Analysis Calculated for $C_{20}H_{25}N_5O_5S.1TFA.1\ H_2O$: C, 45.59; H, 4.87; N, 12.08. Found: C, 45.38; H, 4.79; N, 11.89.

EXAMPLE 38

Synthesis of 4-[[[3-[(aminoiminomethyl)amino]phenyl]-carbonyl]amino]-N-(ethoxycarbonyl)phenylalanine Ethyl Ester, trifluoroacetate Salt

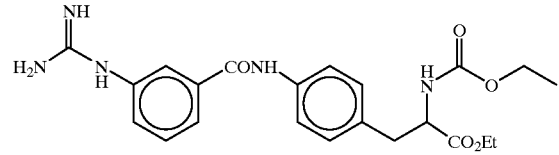

The title compound was prepared in the same manner as described in Example 34, replacing the compound of Example AA with the compound of Example AD.

Analysis Calculated for $C_{22}H_{27}N_5O_5.1.4\ TFA.0.8\ H_2O$: C, 48.39; H, 4.91; N, 11.38. Found: C, 48.43; H, 4.98; N, 11.45.

EXAMPLE 39

Synthesis of 4-[[[3-[(aminoiminomethyl)amino]phenyl]-carbonyl]amino]-N-[(1-methylethoxy)carbonyl]phenylalanine Ethyl Ester, monohydrate trifluoroacetate Salt

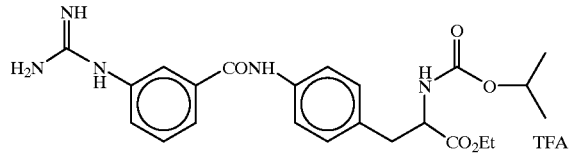

The title compound was prepared in the same manner as described in Example 34, replacing the compound of Example AA with the compound of Example AE.

Analysis Calculated for $C_{23}H_{29}N_5O_5.1TFA.1\ H_2O$: C, 51.11; H, 5.49; N, 11.92. Found: C, 50.91; H, 5.26; N, 11.92.

EXAMPLE 40

Synthesis of 4-[[[3-[(aminoiminomethyl)amino]phenyl]-carbonyl]amino]-N-(phenylsulfonyl)phenylalanine Ethyl Ester, monohydrate trifluoroacetate Salt

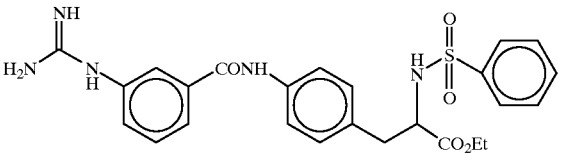

The title compound was prepared in the same manner as described in Example 34 replacing the compound of Example AA with the compound of Example AF.

Analysis Calculated for $C_{25}H_{27}N_5O_5S.1.1\ TFA.1\ H_2O$: C, 50.03; H, 4.65; N, 10.72. Found: C, 50.02; H, 4.33; N, 10.77.

EXAMPLE 41

Synthesis of 4-[[[3-[(aminoiminomethyl)amino]phenyl]-carbonyl]amino]-N-(butylsulfonyl)phenylalanine Ethyl Ester, trifluoroacetate Salt

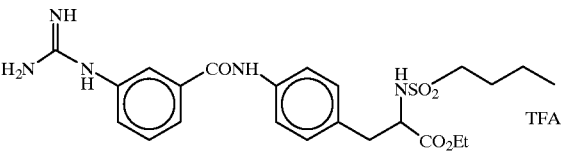

The title compound was prepared in the same manner as described in Example 34, replacing the compound of Example AA with the compound of Example AG.

Analysis Calculated for $C_{23}H_{31}NO_5O_5S.1TFA.0.2H_2O$: C, 49.45; H, 5.38; N, 11.53. Found: C, 49.25; H, 5.04; N, 11.92.

EXAMPLE 42

Synthesis of 4-[[[3-[(aminoiminomethyl)amino]phenyl]-carbonyl]amino]-N-[(2-methylpropoxy)carbonyl)phenyl-alanine, Ethyl Ester, trifluoroacetate Salt

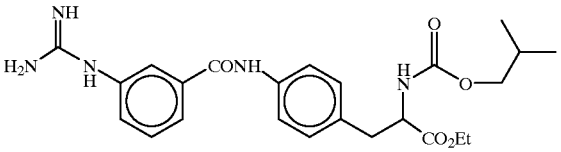

The above compound was prepared in the same manner as described in Example 34, replacing the compound of Example AA with the compound of Example AH.

Analysis Calculated for $C_{24}H_{31}N_5O_5.1.4TFA.0.3\ H_2O$: C, 50.73; H, 5.24; N, 11.30. Found: C, 50.33; H, 5.01; N. 11.53.

EXAMPLE 43

4-[[[3-[(Aminoiminomethyl)amino]phenyl]carbonyl]-amino]-N-[(phenoxy)carbonyl]phenylalanine, Ethyl Ester

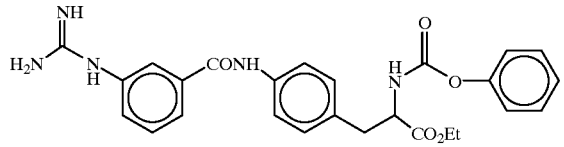

The above compound was prepared in the same manner as described in Example 34, replacing the compound of Example AA with the compound of Example AI.

Analysis Calculated for $C_{26}H_{27}N_5O_4$.1.1 TFA.1 $H_2O$: C, 54.90; H, 4.92; N, 11.35. Found: C, 54.82; H, 4.60; N, 11.51.

EXAMPLE 44

Synthesis of 4-[[[3-[(aminoiminomethyl)amino]phenyl]carbonyl]amino]-N-[(1,1-dimethylethoxy)carbonyl]phenylalanine Ethyl Ester, trifluoroacetate Salt

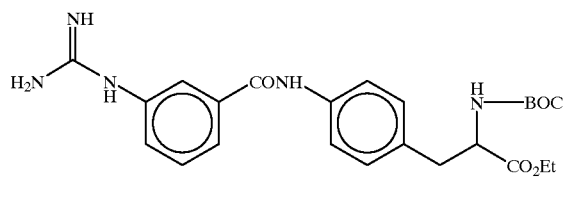

The title compound was prepared in the same manner as described in Example 34, replacing the compound of Example AA with the compound of Example AJ.

Analysis Calculated for $C_{26}H_{27}N_5O_5$.1.2 TFA.1 $H_2O$: C, 52.94; H, 4.73; N, 10.87. Found: C, 53.04; H, 4.71; N, 10.81.

EXAMPLE 45

Synthesis of 4-[[[3-[(aminoiminomethyl)amino]phenyl]-carbonyl]amino]-N-[(1,1-dimethylethoxy)carbonyl]-L-phenylalanine, methyl Ester, trifluoroacetate Salt

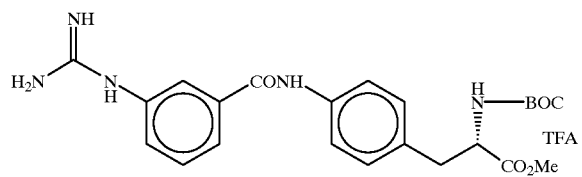

The above compound was prepared in the same manner as described in Example 34, replacing the compound of Example AA with the compound of Example AK.

Analysis Calculated for $C_{23}H_{29}N_5O_5$.1 TFA.0.9 $H_2O$: C, 51.26; H, 5.47; N, 11.96. Found: C, 51.26; H, 5.26; N, 11.85.

EXAMPLE 46

Synthesis of 4-[[[3-[(aminoiminomethyl)amino]phenyl]carbonyl]amino]-N-[(1,1-dimethylethoxy)carbonyl]-D-phenylalanine, methyl Ester

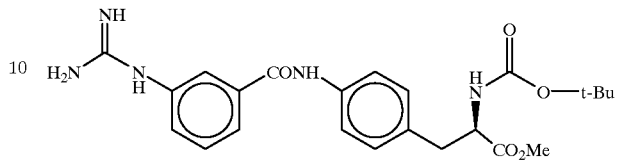

The above compound was prepared in the same manner as described in Example 34, replacing the compound of Example AA with the compound of Example AL.

The above compounds of Examples 36 through 46 were hydrolyzed in the same manner as described in Example 35 to produce the compounds of the following Examples:

EXAMPLE 47

Synthesis of 4-[[[3-[(aminoiminomethyl)amino]phenyl]carbonyl]amino]-N-(phenylcarbonyl)phenylalanine, trifluoroacetate Salt

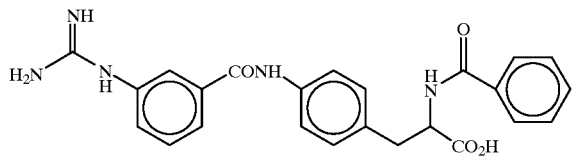

Analysis Calculated for $C_{24}H_{23}N_5O_4$.1.4 TFA.0.9 $H_2O$: C, 51.81; H, 4.25; N, 11.27. Found: C, 51.75; H, 4.25; N, 11.45.

EXAMPLE 48

Synthesis of 4-[[[3-[(aminoiminomethyl)amino]phenyl]carbonyl]amino]-N-(methylsulfonyl)phenylalanine, trifluoroacetate Salt

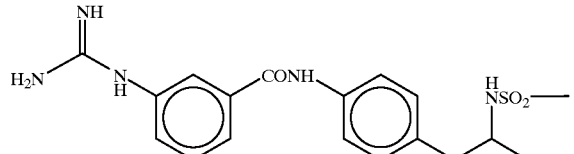

Analysis Calculated for $C_{18}H_{21}N_5O_5S$.1.1 TFA.0.2 $H_2O$: C, 44.73; H, 4.20; N, 13.04. Found: C, 44.66; H, 4.02; N, 13.11.

EXAMPLE 49

Synthesis of 4-[[[3-[(aminoiminomethyl)amino]phenyl]carbonyl]amino]-N-(ethoxycarbonyl)phenylalanine, trifluoroacetate Salt

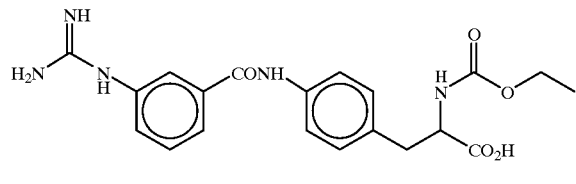

Analysis Calculated for $C_{28}H_{23}N_5O_5 \cdot 1.4$ TFA$\cdot 0.5$ $H_2O$: C, 46.89; H, 4.38; N, 11.99. Found: C, 46.96; H, 4.33; N, 11.75.

EXAMPLE 50

Synthesis of 4-[[[3-[(aminoiminomethyl)amino]phenyl]carbonyl]amino]-N-[(1-methylethoxy)carbonyl]-phenylalanine, trifluoroacetate Salt

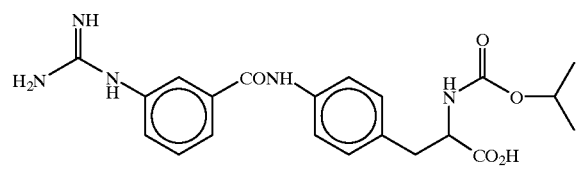

Analysis Calculated for $C_{21}H_{25}N_5O_5 \cdot 1.1$ TFA$\cdot 0.9$ $H_2O$: C, 48.96; H, 4.97; N, 12.31. Found: C, 48.93; H, 4.80; N, 12.48.

EXAMPLE 51

Synthesis of 4-[[[3-[(aminoiminomethyl)amino]phenyl]carbonyl]amino]-N-(phenylsulfonyl)phenylalanine, trifluoroacetate Salt

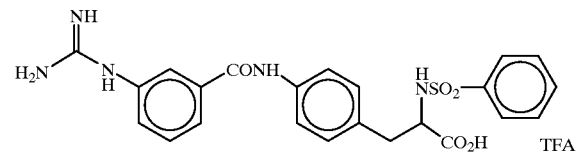

Analysis Calculated for $C_{23}H_{23}N_5O_5S \cdot 1$ TFA$\cdot 0.5$ $H_2O$: C, 49.67; H, 4.17; N, 11.58. Found: C, 49.74; H, 4.22; N, 11.68.

EXAMPLE 52

Synthesis of 4-[[[3-[(aminoiminomethyl)amino]phenyl]carbonyl]amino]-N-(butylsulfonyl)phenylalanine, trifluoroacetate Salt

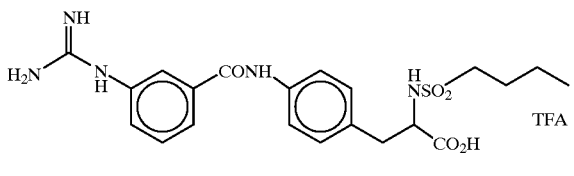

Analysis Calculated for $C_{21}H_{27}N_5O_5S \cdot 1$TFA$\cdot 0.1$ $H_2O$: C, 47.58; H, 4.92; N, 12.13. Found: C, 47.79; H, 4.84; N, 12.12.

EXAMPLE 53

Synthesis of 4-[[[3-[(aminoiminomethyl)amino]phenyl]-carbonyl]amino]-N-[(2-methylpropoxy)carbonyl]-phenylalanine, trifluoroacetate Salt

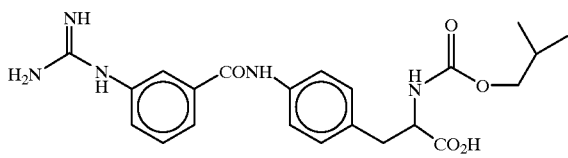

Analysis Calculated for $C_{22}H_{27}N_5O_5 \cdot 1.1$TFA$\cdot 1$ $H_2O$: C, 54.90; H, 4.92; N, 11.35. Found: C, 54.82; H, 4.60; N, 11.51.

EXAMPLE 54

Synthesis of 4-[[[3-[(aminoiminomethyl)amino]phenyl]carbonyl]amino]-N-(methoxycarbonyl)phenylalanine, trifluoroacetate Salt

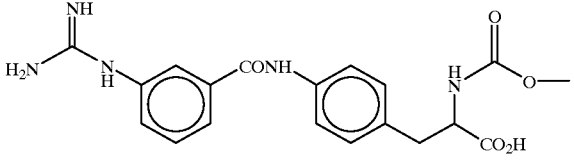

Analysis Calculated for $C_{19}H_{21}N_5O_5 \cdot 1.3$ TFA$\cdot 0.4$ $H_2O$: C, 46.76; H, 4.20; N, 12.62. Found: C, 46.76; H, 3.95; N, 12.65.

EXAMPLE 55

Synthesis of 4-[[[3-[(aminoiminomethyl)amino]phenyl]carbonyl]amino]-N-[(1,1-dimethylethoxy)carbonyl]-phenylalanine, monohydrate trifluoroacetate Salt

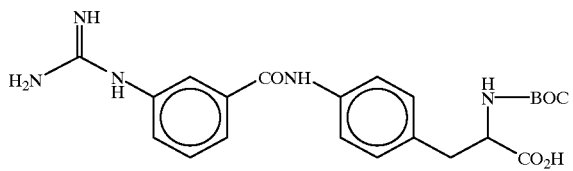

Analysis Calculated for $C_{22}H_{27}N_5O_5 \cdot 1.1 TFA \cdot 1 H_2O$: C, 49.69; H, 5.19; N, 11.99. Found: C, 49.65; H, 4.95; N, 11.95.

EXAMPLE 56

Synthesis of 4-[[[3-[(aminoiminomethyl)amino]phenyl]carbonyl]amino]-N-[(1,1-dimethylethoxy)carbonyl]-L-phenylalanine, trifluoroacetate Salt

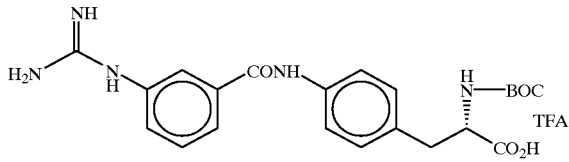

Analysis Calculated for $C_{22}H_{27}N_5O_5 \cdot 1 TFA \cdot 1.1 H_2O$: C, 50.10; H, 5.29; N, 12.17. Found: C, 49.86; H, 5.27; N, 12.20.

EXAMPLE 57

Synthesis of 4-[[[3-[(aminoiminomethyl)amino]phenyl]carbonyl]amino]-N-[(1,1-dimethylethoxy)carbonyl]-D-phenylalanine, monohydrate trifluoroacetate Salt

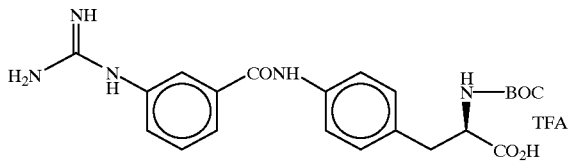

Analysis Calculated for $C_{22}H_{27}N_5O_5 \cdot 1 TFA \cdot 1 H_2O$: C, 50.26; H, 5.27; N, 12.21. Found: C, 50.20; H, 4.95; N, 12.25.

EXAMPLE 58

1,1-dimethylethyl-4-[2-[[[3-[(aminoiminomethyl)amino]-phenyl]carbonyl]amino]ethyl]benzenepropanoate, monohydrate trifluoroacetate Salt

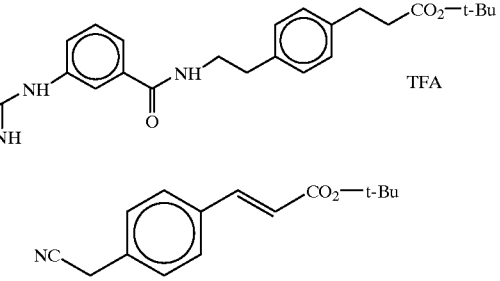

Step A

A mixture of p-bromophenylacetonitrile (5.03 g, 25.6 mmol), t-butyl acrylate (6.0 mL, 40.8 mmol), palladium acetate (0.060 g, 0.26 mmol), and tri-o-tolylphosphine (0.326 g, 1.0 mmol) in triethylamine (12 mL) was heated to reflux under argon for 6 hours. The resulting orange mixture was poured into ice and acidified to pH 1 (pH paper) with 1 M HCl. The mixture was extracted with EtOAc (150 mL). The organic layer was collected, dried over $MgSO_4$, and concentrated in vacuo to give an orange/yellow solid. The solid was recrystallized from ether/hexane to give yellow crystals (1.91 g). NMR was consistent with the proposed structure.

Step B

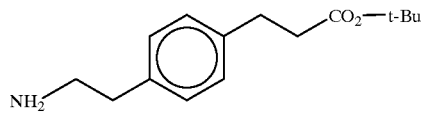

The compound of Step A (1.9 g, 7.8 mmol) was dissolved in i-PrOH/HCl and hydrogenated with 10% Pd/C in a Parr Shaker (60 psi) for 10 hours at room temperature. The catalyst was removed and the filtrate was concentrated in vacuo. The residue was partitioned between saturated $NaHCO_3$ and ether. The aqueous layer was back-extracted with ether. The organic layers were combined, dried over $K_2CO_3$, and concentrated in vacuo to give a pale yellow oil (1.93 g, 98% yield). NMR was consistent with proposed structure.

Step C

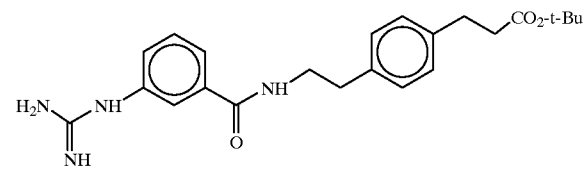

The compound of Step B (0.504 g, 2.0 mmol) was coupled with the compound of Example A according to procedures described in Example 29. The crude material was purified by HPLC-Method 1 to give a sticky white solid (0.50 g).

Analysis Calculated for $C_{23}H_{30}N_4 \cdot 1.0$ TFA+1.0 $H_2O$: C, 55.34; H, 6.13; N, 10.33. Found: C, 55.34; H, 5.77; N, 10.16. M+=410.

EXAMPLE 59

4-[2-[[[3-[(aminoiminomethyl)amino]phenyl]carbonyl]amino]ethyl]benzenepropanoic Acid, trifluoroacetate Salt

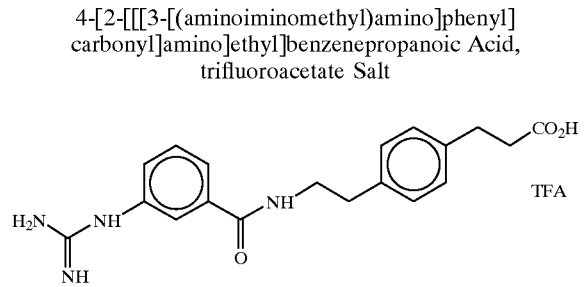

A solution of the compound of Example 58 in $CH_2Cl_2$ (4 mL) was cooled to 0° C. and TFA (3 mL) was added under argon. The ice bath was removed and the reaction allowed to warm to room temperature. The reaction was stirred for 4.5 hours, then concentrated under a stream of $N_2$. The crude material was slurried with acetonitrile and the resulting white solid was collected by vacuum filtration (0.235 g).

Analysis Calculated for $C_{19}H_{22}N_4O_3 \cdot 1.0$ TFA: C, 53.85; H, 4.95; N, 11.96. Found: C, 53.59; H, 4.93; N, 11.98. MH+=355.

EXAMPLE AM

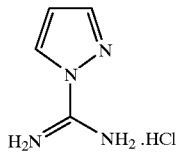

The above compound was prepared according to (Bernatowicz, JOC, Vol. 57, No. 8, (1992), p. 2497–2502. NMR was consistent with the proposed structure.

EXAMPLE AN

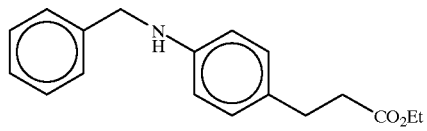

To a stirred solution of benzaldehyde (763 mg, 7.2 mmol), and the compound of Example F (1.5 g, 6.5 mmol) in ethanol (10 mL) was added borane-pyridine complex (0.2 mL), and the mixture was stirred at room temperature for 30 minutes. The reaction mixture was then concentrated and the residue was dissolved in ethyl acetate, washed with saturated sodium bicarbonate and brine, dried over $Na_2SO_4$, and evaporated. The crude product was chromatographed on silica gel using EtOAc/Hexane (1:8) as eluant to give 1.3 g of the desired compound as yellow oil.

EXAMPLE AO

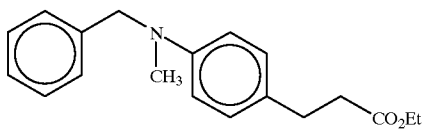

To a stirred solution of formaldehyde (37%, 0.28 mL, 3.5 mmol), the compound of Example AN (0.9 g, 3.2 mmol) in ethanol (5 mL) was added borane-pyridine complex (BPC) (0.32 mL 3.5 mmol), and the mixture was stirred at room temperature for 1 hour. One additional equivalent of formaldehyde and BPC were added to the reaction and stirred overnight. The reaction mixture was concentrated and the residue was dissolved in ethyl acetate, washed with saturated sodium bicarbonate and brine, dried over $Na_2SO_4$ and evaporated. The crude product was chromatographed on silica gel using EtOAc/Hexane (1:8) as eluant to give 900 mg of the desired compound as colorless oil.

EXAMPLE AP

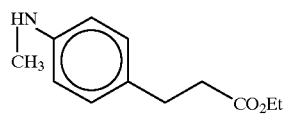

The compound of Example AO (1.3 g, 4.5 mmol) was dissolved in a mixture of EtOH (20 mL) and acetyl chloride (353 mg, 4.5 mmol) was added. This mixture was transferred to a pressure bottle with a catalytic amount of 10% Pd/C wetted with ethanol. The reaction was stirred for 3 hours at room temperature under a $H_2$ pressure of 5 psi. The reaction mixture was filtered and concentrated to afford 750 mg of an oil.

EXAMPLE AQ

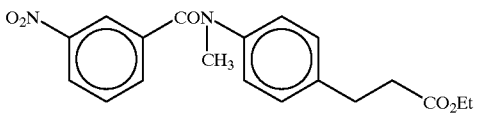

To a stirred solution of the product of Example AP (710 mg, 2.9 mmol) in methylene chloride (15 mL) at 0° C. was added 3-nitrobenzoyl chloride (557 mg, 3 mmol), followed by triethylamine (0.85 mL, 6 mmol). The reaction mixture was stirred at room temperature overnight. The reaction mixture was then concentrated and the residue was dissolved in ethyl acetate, washed with water and brine, dried over $Na_2SO_4$ and evaporated. The residue was chromatographed on silica gel using EtOAc/Heptane (60/40) as eluant to give 1 g of the pure desired compound.

EXAMPLE AR

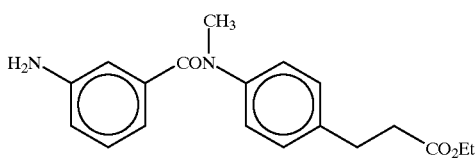

The compound of Example AQ was reduced in a similar manner as described in Example AA.

EXAMPLE AS

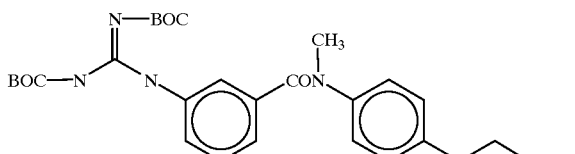

To a stirred mixture of the compound of Example AR (610 mg, 1.87 mmol), the compound of Example AZ (530 mg, 1.92 mmol) and triethylamine (0.86 mL, 6.1 mmol) in dimethyl formamide (7 mL) at 0° C. under argon was added mercury dichloride and the mixture was stirred at 0° C. for 3 hours. The mixture was diluted with ethyl acetate and filtered through celite. The filtrate was concentrated and the residue was treated with water and, extracted with ethyl acetate. The combined organic phases were washed with brine, dried over $Na_2SO_4$ and evaporated. The residue was chromatographed on silica gel using EtOAc/Heptane (50/50) as eluant to give 730 mg of the pure desired compound as a white solid.

EXAMPLE 60

Synthesis of ethyl 4-[[[3-[(aminoiminomethyl)amino]phenyl]carbonyl]methylamino]benzenepropanoate, trifluoroacetate Salt

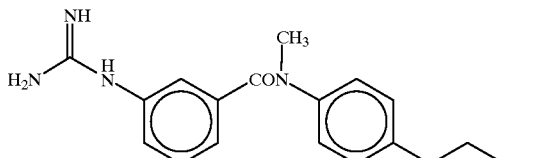

The compound of Example AS (720 mg, 1.27 mmol) was dissolved in methylene chloride (6 mL) and cooled to 0° C. To the solution was added trifluoroacetic acid (2 mL). After 15 minutes the ice bath was removed and the reaction stirred for 4 hours. The reaction mixture was then concentrated and the residue was purified by reverse phase HPLC-Method 1 to give 610 mg of a colorless oil. Analysis Calculated for $C_{20}H_{24}N_4O_3$.1 TFA.1.2 $H_2O$: C, 52.42; H, 5.48; N, 11.11. Found: C, 52.25: H, 5.39; N, 11.08.

EXAMPLE 61

Synthesis of 4-[[[3-[(aminoiminomethyl)amino)phenyl]carbonyl]methylamino]nbenzenepropanoic Acid, monohydrate trifluoroacetate salt

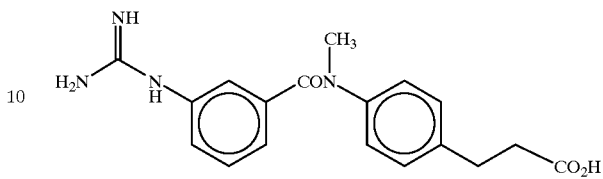

The compound of Example 60 was hydrolyzed in the same manner as described in Example 35.

Analysis calculated for $C_{18}H_{20}N_4O_3$.1.6 TFA.1 $H_2O$: C, 47.08; H, 4.40; N, 10.36. Found: C, 47.14; H, 4.34; N, 10.34.

EXAMPLE AT

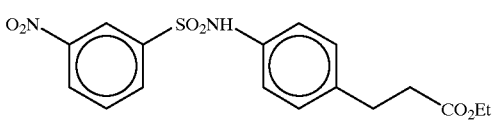

To a stirred solution of the compound of Example F (1.07 g, 4.7 mmol) in methylene chloride (15 mL) at 0° C. was added 3-nitrobenzenesulphonyl chloride (1.03 g, 4.7 mmol) followed by triethylamine (1.25 mL, 9 mmol). The mixture was stirred at room temperature overnight under argon. The reaction mixture was then concentrated and the residue was treated with water and extracted with chloroform. The combined organic phases were washed with brine, dried over $Na_2SO_4$ and evaporated. The residue was chromatographed on silica gel using 1% MeOH/$CH_2Cl_2$ as eluant to give 1.2 g of the pure desired compound as a yellow oil.

EXAMPLE AU

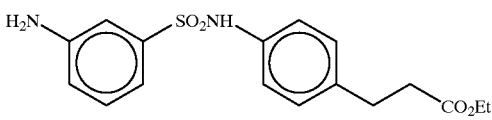

The compound of Example AT was reduced in the same manner as described in Example AA.

EXAMPLE AV

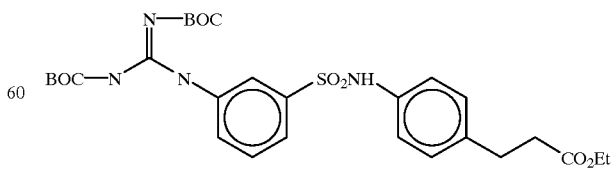

The above compound was synthesized under conditions similar to those described in Example AS.

EXAMPLE 62

Synthesis of 4-[[[3-[(aminoiminomethyl)amino]phenyl]sulfonyl]amino]benzenepropanoic Acid, trifluoroacetate Salt

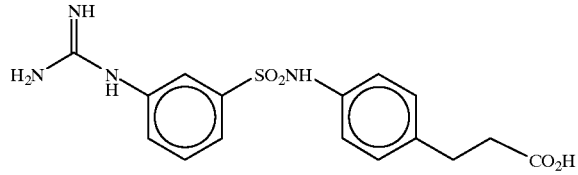

The compound of Example AV (130 mg, 0.22 mmol) was dissolved in dioxane (10 mL), and treated with 6 N HCl (10 mL). The reaction mixture was stirred at room temperature overnight, concentrated and purified by reverse phase HPLC-Method 1.

Analysis Calculated for $C_{16}H_{18}N_4O_4S.1.4$ TFA.0.3 $H_2O$: C, 42.81; H, 3.82; N, 10.61. Found: C, 43.15; H, 3.62; N, 10.07.

EXAMPLE AW

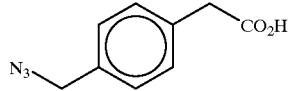

To a stirred solution of 4-(bromomethyl)-phenylacetic acid (1.18 g, 5.15 mmol) in dimethyl formamide (10 mL) was added sodium azide (402 mg, 6.18 mmol), and mixture was heated at 60° C. for 4 hours. The reaction mixture was cooled to room temperature, poured into water, and extracted with ethyl acetate. The combined organic phases were washed with water and brine, dried over $MgSO_4$ and evaporated to afford 0.92 g of the desired compound.

EXAMPLE AX

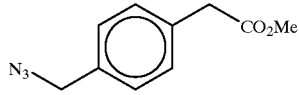

The compound of Example AW (0.92 g, 4.8 mmol) was dissolved in methanol (100 mL) at 0° C. and a stream of hydrogen chloride gas was bubbled into the solution for 10 minutes. The mixture was then stirred for 2 hours at 0° C. The solvent was removed under reduced pressure to give 1 g of the desired compound as a colorless oil.

Analysis Calculated for $C_{10}H_{11}N_3O_2$: C, 58.53; H, 5.40; N, 20.48. Found: C, 58,27; H, 5.35, N, 20.13.

EXAMPLE AY

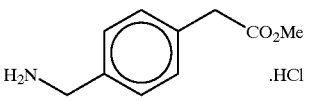

The compound of Example AX (800 mg, 3.9 mmol) was dissolved in EtOH (30 mL) and transferred to a Parr Shaker with 4% Pd/C (200 mg). The reaction was shaken for 24 hours at room temperature under 60 psi pressure of $H_2$. The reaction mixture was filtered and concentrated and the residue was dissolved in 4 N HCl dioxane solution (4 mL). The solvent was removed and the residue was recrystalized from ether to give 550 mg of pure title compound as white solid.

EXAMPLE 63

Synthesis of ethyl 4-[[[3-[(aminoiminomethyl)amino]phenyl]carbonyl]amino]benzenepropanoate, monohydrate trifluoroacetate Salt The title compound was prepared in the same manner as described in Example 34, replacing the compound of Example AA with the compound of Example F.

Analysis Calculated for $C_{19}H_{22}N_4O_3.1.1$ TFA.1 $H_2O$: C, 51.15; H, 5.08; N, 11.25. Found: C, 51.17; H, 4.54; N, 11.40.

EXAMPLE 64

Synthesis of 4-[[[3-[(aminoiminomethyl)amino]phenyl]carbonyl]amino]benzenepropanoic Acid, hydrochloride The compound of Example 63 was hydrolyzed in the same manner as described in Example 62.

Analysis Calculated for $C_{17}H_{18}N_4O_3.0.4$ $H_2O.1$ HCl: C, 55.18; H, 5.39; N, 15.14. Found: C, 55.25; H, 5.35; N, 15.00.

EXAMPLE 65

Synthesis of 4-[[[3-[(aminoiminomethyl)amino]phenyl]carbonyl]amino]phenylalanine, trifluoroacetate Salt

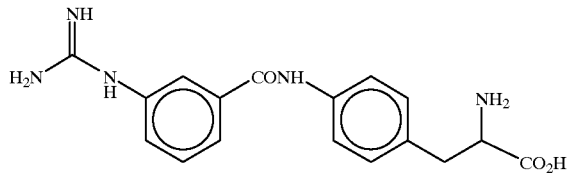

Step A

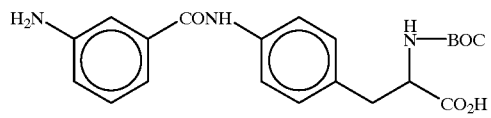

The compound of Example AJ was coupled to 3-nitrobenzoyl chloride as described in Example AQ. The resulting nitro compound was hydrogenated in the same manner as described in Example AA to produce the above compound.

Step B

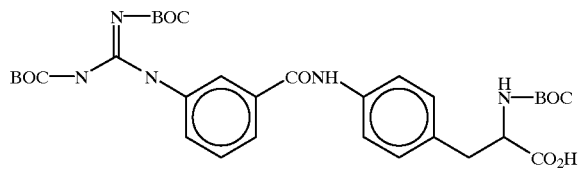

The above compound was synthesized under conditions similar to those described in Example AS using the product of Step A.

Step C

To a solution of the product of Step B (220 mg, 0.34 mmol) in $CH_2Cl_2$ (5 mL) was added trifluoroacetic acid (1 mL). The reaction was stirred for 4 hours, concentrated and purified by reverse phase HPLC to afford the title compound.

Analysis Calculated for $C_{17}H_{19}N_5O_3$.2.1 TFA.0.2 $H_2O$: C, 43.57; H, 3.71; N, 11.98. Found: C, 43.26; H, 3.49; N, 11.75.

EXAMPLE AZ

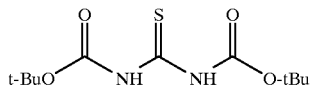

An oven-dried flask equipped with a stirring bar was charged with NaH (60% in mineral oil, 3.36 g, 140 mmol). The NaH was triturated with hexane followed by THF (distilled) under argon. The NaH was then suspended in THF (250 mL) and the mixture was cooled to 0° C. Thiourea (1.426 g, 18.7 mmol) was added in one portion. After 5 minutes, the reaction was allowed to stir at room temperature for 10 minutes. The reaction was cooled to 0° C. and di-t-butyl dicarbonate (9.001 g, 41.2 mmol) was added. Within 15 minutes of addition, the reaction became a tan slurry. The reaction was allowed to warm slowly to room temperature over 2 hours and then stirred at room temperature for an additional 1 hour. The reaction was quenched with saturated $NaHCO_3$ (50 mL) and poured into water (600 mL). The mixture was extracted with EtOAc (3×150 mL) and the organic layers were combined and dried over $Na_2SO_4$. Concentration in vacuo gave the product as a yellow solid (4.23 g, 82% yield). NMR was consistent with the proposed structure.

EXAMPLE 68

Synthesis of N-acetyl-4-[[[[3-[(aminoiminomethyl)amino]phenyl]amino]carbonyl]amino]phenylalanine, trifluoroacetate Salt

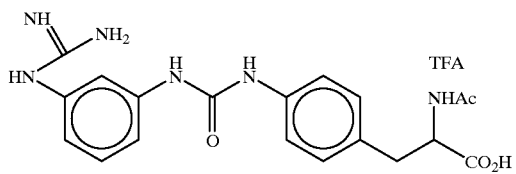

Step A

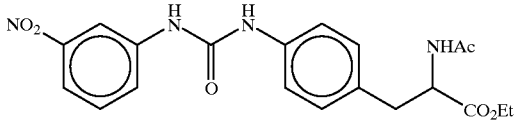

To a stirred solution of 3-nitrophenylisocyanate (0.082 g, 0.5 mmol, Aldrich) in methylene chloride (5 mL) was added to the product from Example AA (0.1 g, 0.4 mmol) in small portions over 5 minutes. The mixture was stirred 18 hours at room temperature. The mixture was then poured into 10% aqueous sodium hydroxide (50 mL) and washed with ethyl acetate (2×25 mL). The basic solution was acidified with 10% HCl and the resulting precipitate was filtered and dried. This produced 0.16 g (97%) of the title compound.

HRMS (MH+) for $C_{20}H_{23}N_4O_6$ Calculated: 415.1618; Found: 415.1654.

Step B

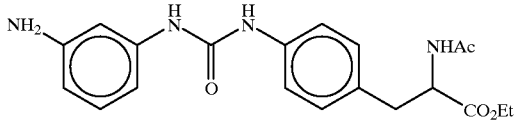

A stirred solution of the product of Example 68A (0.16 g, 0.39 mmol) in ethyl alcohol (25 mL) and THF (50 mL) was hydrogenated over 4% palladium on carbon under an atmosphere of hydrogen at 5 psi. The solvent was removed at reduced pressure. This produced 0.14 g (93%) of the title compound.

HRMS (M+) for $C_{20}H_{24}N_4O_4$ Calculated: 384.1797; Found: 384.1837

Step D

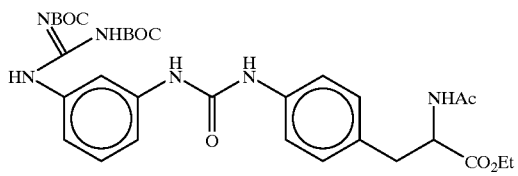

The product from Example 68B (0.14 g, 0.36 mmol) was subjected to the reaction conditions described for the preparation of Example AS. The crude product was chromatographed on silica gel eluting with ethyl acetate which produced 0.21 g (93%) of the title compound.

APCI MS (MH+) for $C_{31}H_{43}N_6O_8$ Calculated: 627; Found: 627.

Step D

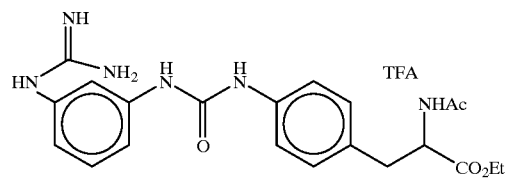

The product from Example 68C (0.21 g, 0.34 mmol) was subjected to the reaction conditions described for the preparation of Example 60. This produced 0.17 g (93%) of the title compound.

APCI MS (free base MH+) for $C_{21}H_{27}N_6O_4$ Calculated: 427; Found: 427.

Step E

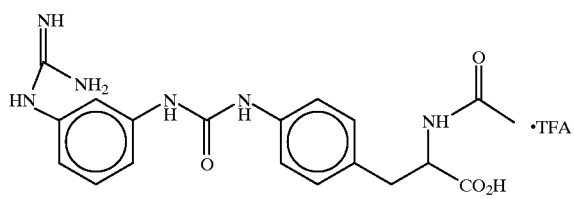

The product of Example 68D (0.17 g, 0.31 mmol) in methyl alcohol (1 mL) was cooled (0° C.) and treated with 1 N lithium hydroxide solution (0.7 mL, 0.7 mmol). The solution was warmed to room temperature and stirred 18 hours. The volatile components were removed at reduced pressure on a rotary evaporator. The crude product was chromatographed (reverse phase HPLC, gradient elution with water/acetonitrile/trifluoroacetic acid). This produced 100 mg (63%) of the title compound.

ESI MS (free base MH+) for $C_{19}H_{23}N_6O_4$ Calculated: 399; Found: 399.

EXAMPLE 69

Synthesis of [4-[[[3-[(aminoiminomethyl)amino]-phenyl]carbonyl]amino]phenyl]butanedioic Acid, trifluoroacetate Salt

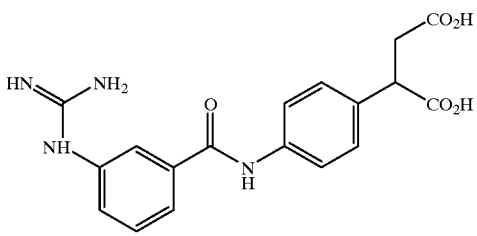

Step A

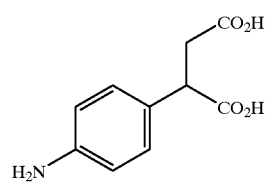

4-Nitrophenylsuccinic acid (Lancaster) (5 g, 2.0 mmol) was added to absolute ethanol (70 mL) in a Parr jar. Palladium on carbon 5% (700 mg) was added and the mixture was hydrogenated under 50 psi in a Parr apparatus for a period of 2.5 hours. After complete reaction the palladium catalyst was removed under reduced pressure and the sample dried in vacuo to give a white colored solid (5 g, 99% yield). NMR and MS were consistent with the proposed structure.

Step B

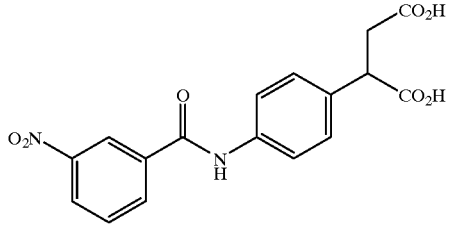

The 4-anilinophenylsuccinic acid (2 g) from Step A was placed in a flask followed by water (50 mL) and KOH (1 g). To this solution 3-nitrobenzoyl chloride (Aldrich) dissolved in acetonitrile (10 mL) was added dropwise. The reaction was monitored by HPLC. After the reaction was complete (1 hour), 10% HCl was added and the solution was extracted with ethyl acetate and dried over $Na_2SO_4$. After evaporation of the solvent a white solid remained (1.5 g). NMR and MS were consistent with the proposed structure.

Step C

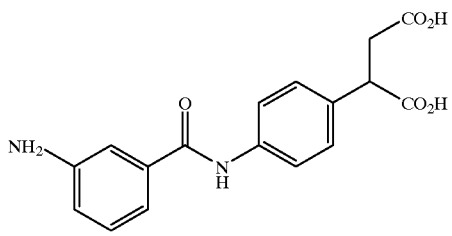

The white solid from Step B (1.5 g) was added to absolute ethanol (50 mL) and acetic acid (2 mL) in a Parr jar. Palladium on carbon 5% (500 mg) was added and the mixture was hydrogenated under 50 psi in a Parr apparatus for a period of 1.5 hours. After complete reaction the palladium catalyst was removed by filtration through a plug of celite. The solvent was removed under reduced pressure and the sample dried in vacuo to give a white colored solid (1.5 g, 99% yield). NMR and MS were consistent with the proposed structure.

Step D

A portion of the white solid from Step C above (400 mg) was added to acetonitrile (20 mL) followed by pyrazole carboxamidine HCl (Aldrich) (1 g) and DIEA. The mixture was heated to reflux for 4 hours. After the reaction was complete water was added and TFA was added to bring the pH=2. The product was purified by reverse phase chromatography (water/acetonitrile) to result in the title compound as a white solid (320 mg). NMR and MS were consistent with the proposed structure.

EXAMPLE 70

Synthesis of 4-(1,1-dimethylethyl) 1-ethyl[4-[[[3-[(aminoiminomethyl)amino]phenyl]carbonyl]amino]phenyl]-butanedioate, trifluoroacetate Salt

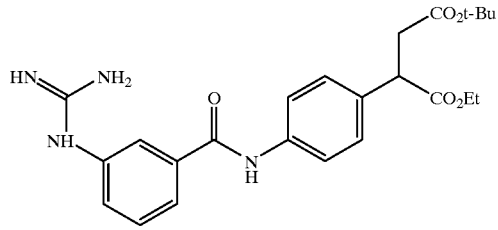

Step A

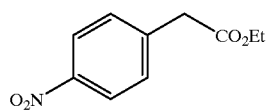

4-Nitrophenylacetic acid (Aldrich) (10 g) was added to a flask containing ethanol (200 mL) and acetyl chloride (20 mL). The solution was heated to reflux for 1 hour then left to stir overnight at room temperature. The solvent was removed under reduced pressure to result in a solid which was dissolved in hexane (150 mL) and washed with water (100 mL). The hexane solution was dried over $Na_2SO_4$ and the solvent removed under reduced pressure to give the ethyl ester (12 g) as a white solid. NMR and MS were consistent with the proposed structure.

Step B

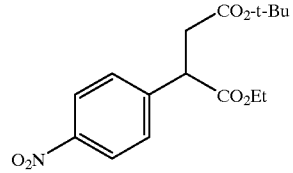

Ethyl 4-nitrophenylacetate (5 g) from Step A was dissolved in THF (100 mL). Potassium tert-butoxide (45 mL) was added at 0° C. The solution turned a deep purple indicating the anion was formed. After 15 minutes at 0° C. tert-butyl bromacetate (5.2 g) was added. After the reaction was complete 10% HCl was added and the product extracted with ethyl acetate, and dried over $Na_2SO_4$ to give a dark yellow oil (7 g). NMR and MS were consistent with the proposed structure.

Step C

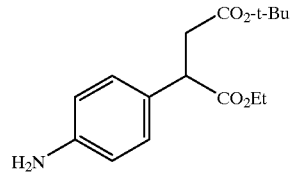

The compound from Step B (5 g) was added to absolute ethanol (70 mL) and acetic acid (2 mL) in a Parr jar. Palladium on carbon 5% (700 mg) was added and the mixture was hydrogenated under 50 psi in a Parr apparatus for a period of 2.5 hours. After complete reaction the palladium catalyst was removed by filtration through a plug of celite. The solvent was removed under reduced pressure and the sample dried in vacuo to give a white colored solid (5 g, 99% yield). NMR and MS were consistent with the proposed structure.

Step D

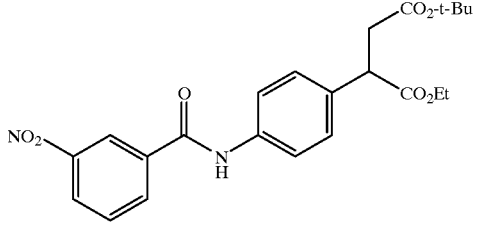

The 4-anilinophenylsuccinic diester (2 g) from Step C was placed in a flask followed by water (50 mL) and $K_2CO_3$ (1 g). To this solution 3-nitrobenzoyl chloride (Aldrich) dissolved in acetonitrile (10 mL) was added dropwise. The reaction was monitored by HPLC. After the reaction was complete (1 hour), 10% HCl was added and a white solid was separated (1.5 g). NMR and MS were consistent with the proposed structure.

Step E

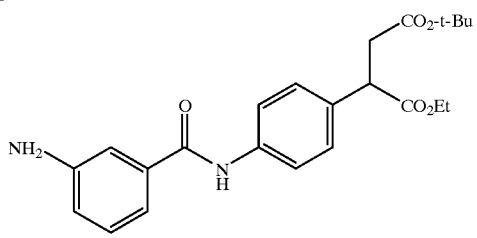

The compound from Step D (1 g) was added to absolute ethanol (70 mL) and acetic acid (2 mL) in a Parr jar. Palladium on carbon 5% (700 mg) was added and the mixture was hydrogenated under 50 psi in a Parr apparatus for a period of 2.5 hours. After complete reaction the palladium catalyst was removed by filtration through a plug of celite. The solvent was removed under reduced pressure and the sample dried in vacuo to give a white colored solid (1 g, 99% yield). NMR and MS were consistent with the proposed structure.

Step F

A portion of the white solid from Step E (1 g) was added to acetonitrile (20 mL) followed by pyrazole carboxamidine HCl (Aldrich) (2 g) and DIEA (2 g). The mixture was heated to reflux for 6 hours. After the reaction was complete water was added and TFA was added to bring the pH=2. The product was purified by reverse phase chromatography (water/acetonitrile) to result in the title compound as a white solid (820 mg). NMR and MS were consistent with the proposed structure.

EXAMPLE 71

Synthesis of 1-ethyl hydrogen[4-[[[3-[(aminoiminomethyl)amino]phenyl]carbonyl]amino]-phenyl]butanedioate, trifluoroacetate Salt

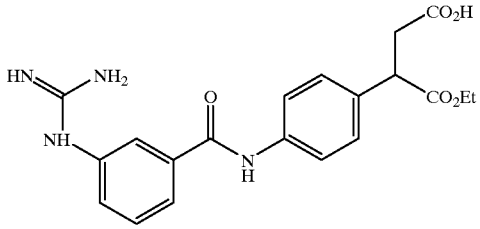

Step A

The compound from Step D in Example 70 (500 mg) was added to methylene chloride (5 mL) followed by TFA (2 mL). The reaction was monitored by HPLC. After the reaction was complete the product was purified by reverse phase chromatography (water/acetonitrile) to result in a white solid (310 mg). NMR and MS were consistent with the proposed structure.

EXAMPLE 72

Synthesis of 1,1-dimethylethyl 4-[[[3-[(aminoiminomethyl)amino]phenyl]carbonyl]-amino]-β-[[[(ethoxycarbonyl)methyl]amino]-carbonyl]benzenepropanoate, trifluoroacetate Salt

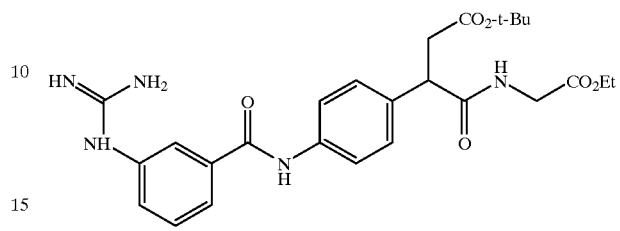

Step A

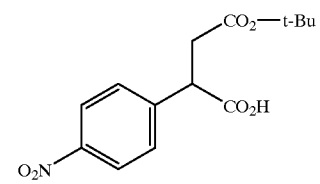

The product from Step B (2 g) of Example 70 was added to water/acetonitrile 1:1 (50 mL), followed by the addition of lithium hydroxide (100 mg, 0.4 mmol). The reaction was stirred at 25° C., and monitored by HPLC. After complete hydrolysis the product was extracted with ethyl acetate dried over $Na_2SO_4$ to give a yellow oil (1.7 g). NMR and MS were consistent with the proposed structure.

Step B

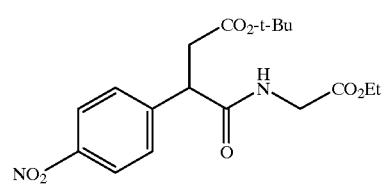

N,N'-Disuccinimidyl carbonate (1.7 g) was added to the 4-nitro-phenyl adduct from Step A (1.5 g) in dry dimethylformamide (20 mL) followed by dimethylaminopyridine (200 mg). After a period of 1 hour glycine ethyl ester hydrochloride (1 g) in DMF (10 mL) and NMM (2 mL) was added in one portion. After complete reaction, the product was extracted into ethyl acetate and worked up to give the desired product (1.5 g). NMR and MS were consistent with proposed structure.

Step C

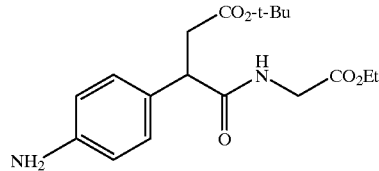

The compound from Step B (1 g) was added to absolute ethanol (70 mL) in a Parr jar. Palladium on carbon 5% (500 mg) was added and the mixture was hydrogenated under 50 psi in a Parr apparatus for a period of 2.5 hours. After complete reaction the palladium catalyst was removed by filtration through a plug of celite. The solvent was removed under reduced pressure and the sample dried in vacuo to give a white colored solid (1 g, 99% yield). NMR and MS were consistent with the proposed structure.

Step D

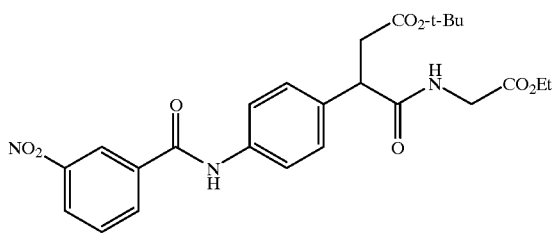

The product from Step C (1 g) was placed in a flask, followed by addition of water (50 mL) and $K_2CO_3$ (1 g). To this solution 3-nitrobenzoyl chloride (Aldrich) dissolved in acetonitrile (10 mL) was added dropwise. The reaction was monitored by HPLC. After the reaction was complete (1 hour), 10% HCl was added and the solution was extracted with ethyl acetate and dried over $Na_2SO_4$. After evaporation of the solvent a white solid remained (1.56 g). NMR and MS were consistent with the structure.

Step E

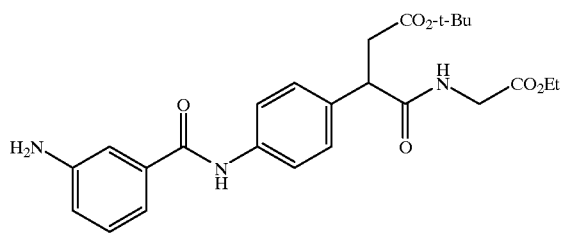

The compound from Step D (1.2 g) was added to absolute ethanol (70 mL) and acetic acid (2 mL) in a Parr jar. Palladium on carbon 5% (700 mg) was added and the mixture was hydrogenated under 50 psi in a Parr apparatus for a period of 2.5 hours. After complete reaction the palladium catalyst was removed by filtration through a plug of celite. The solvent was removed under reduced pressure and the sample dried in vacuo to give a white colored solid (1.1 g, 99% yield). NMR and MS were consistent with the proposed structure.

Step F

A portion of the white solid from Step E (1 g) was added to acetonitrile (20 mL) followed by pyrazole carboxamidine HCl (Aldrich) (2 g) and DIEA. The mixture was heated to reflux for 6 hours. After the reaction was complete water was added and TFA was added to bring the pH=2. The product was purified by reverse phase chromatography (water/acetonitrile) to result in the title compound as a white solid (700 mg). NMR and MS were consistent with the structure.

EXAMPLE 73

Synthesis of 4-[[[3-[(aminoiminomethyl)amino]phenyl]-carbonyl]amino]-beta-[[(carboxymethyl)amino]carbonyl]-benzenepropanoic Acid, trifluoroacetate Salt

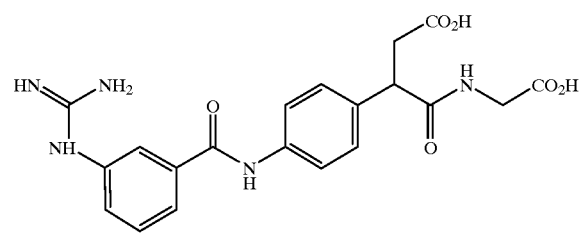

Step A

The compound of Example 72 (500 mg) was added to methylene chloride (5 mL) followed by the addition of TFA (2 mL). The reaction was monitored by HPLC. After the reaction was complete the product was freeze dried. The product was added to water/aceonitrile 1:1 (50 mL), followed by the addition of lithium hydroxide (100 mg, 0.4 mmol). The reaction was stirred at 25° C., and monitored by HPLC. After complete hydrolysis the product was extracted with ethyl acetate and dried over $Na_2SO_4$ to give a yellow oil (450 mg). NMR and MS were consistent with the proposed structure.

EXAMPLE 74

Synthesis of 1,1-dimethylethyl 4-[[[3-[(aminoiminomethyl)amino]phenyl]carbonyl]amino]-3-hydroxybenzenepropanoate, trifluoroacetate Salt

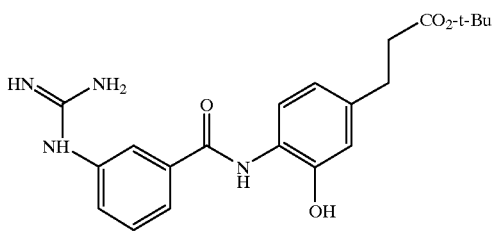

Step A

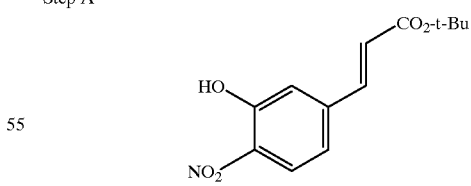

To 4-nitro-3-hydroxy benzaldehyde (Aldrich) (5 g) in acetonitrile (40 mL) was added (tert-butoxycarbonylmethylene)triphenylphosphorane (Aldrich) (11 g) and DBU (1 mL). The reaction was stirred for 1 hour. The solvent was concentrated to 20 mL and the product crystallized from the solution (4 g). NMR and MS were consistent with the proposed structure.

Step B

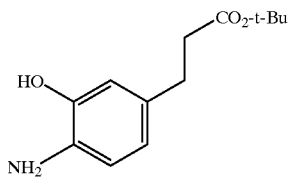

The compound from Step A (3 g) was added to absolute ethanol (70 mL) in a Parr jar. Palladium on carbon 5% (700 mg) was added and the mixture was hydrogenated under 50 psi in a Parr apparatus for a period of 2.5 hours. After complete reaction the palladium catalyst was removed by filtration through a plug of celite. The solvent was removed under reduced pressure and the sample dried in vacuo to give a white colored solid (3 g, 99% yield). NMR and MS were consistent with the proposed structure.

Step C

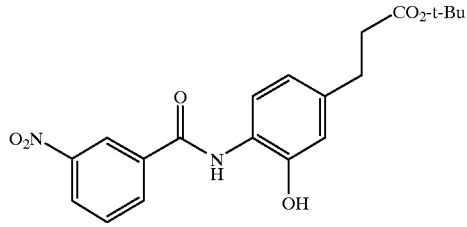

The product from Step B (1.5 g) was placed in a flask followed by the addition of methylenechloride (50 mL) and NMM (2 g). To this solution 3-nitrobenzoylchloride (Aldrich) was added. The reaction was monitored by HPLC. After the reaction was complete (1 hour) 10% HCl was added and the solution was extracted with ethyl acetate and dried over $Na_2SO_4$. After evaporation of the solvent a white solid remained (3 g). NMR and MS were consistent with the proposed structure.

Step D

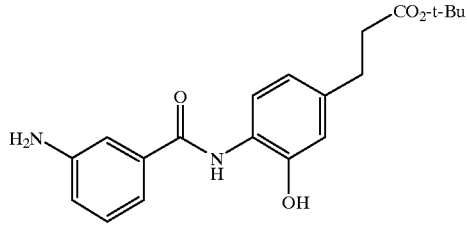

The compound from Step C (1 g) was added to absolute ethanol (70 mL) and acetic acid (2 mL) in a Parr jar. Palladium on carbon 5% (500 mg) was added and the mixture was hydrogenated under 50 psi in a Parr apparatus for a period of 2.5 hours. After complete reaction the palladium catalyst was removed by filtration through a plug of celite. The solvent was removed under reduced pressure and the sample dried in vacuo to give a white colored solid (1 g, 99% yield). NMR and MS were consistent with the proposed structure.

Step E

The product from Step D (1 g) was added to macetonitrile (20 mL) followed by pyrazole carboxamidine HCl (Aldrich) (23 g) and DIEA. The mixture was heated to reflux for 6 hours. After the reaction was complete, water and TFA were added to bring the pH=2. The product was purified by reverse phase chromatography (water/acetonitrile) to result in the title compound as a white solid (700 mg). NMR and MS were consistent with the proposed structure.

EXAMPLE 75

Synthesis of 4-[[[3-[(aminoiminomethyl)amino]phenyl]-carbonyl]amino]-3-hydroxybenzenepropanoic Acid, trifluoroacetate Salt

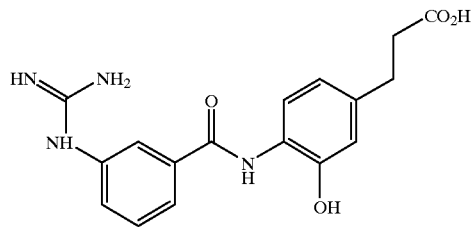

Step A

The compound of Example 74 (300 mg) was added to methylene chloride (5 mL) followed by the addition of TFA (2 mL). The reaction was monitored by HPLC. After the reaction was complete (2 hours) the product was purified by reverse phase chromatorgraphy (water/acetonitrile) to result in a white solid (110 mg). NMR and MS were consistent with the proposed structure.

EXAMPLE 76

4-[[[3-[(Aminoiminomethyl)amino]phenyl]carbonyl]-amino]-N-[(1,1-dimethylethoxy)carbonyl]-2-methoxyphenylalanine, Ethyl Ester

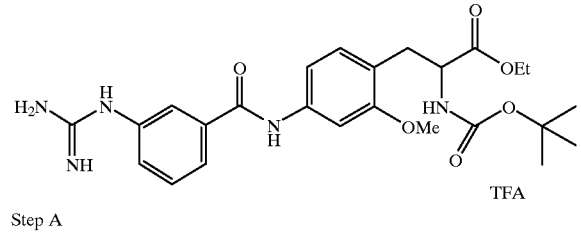

TFA

Step A

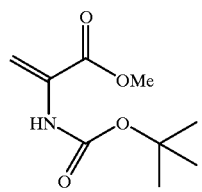

To a solution of methyl pyruvate (2.042 g, 20 mmol) in benzene (70 mL) was added tert-butyl carbamate (9.372 g, 80 mmol) and the resulting suspension was heated to obtain full dissolution. The mixture was heated to 70° C. and phosphorus oxychloride (7.3 mL, 80 mmol) was added dropwise over 1 minute. After 2 minutes a heavy white precipitate appeared and the reaction mixture was stirred at 70° C. for an additional 15 minutes. The mixture was rapidly cooled, poured into an aqueous solution of sodium dihydrogenphosphate (pH 4) and the aqueous layer extracted three times with dichloromethane. The organic layer was washed with water, dried and evaporated under reduced pressure. Chromatography of the resulting oil on silica gel eluting with dichloromethane afforded 1.6 g of the product.

Step B

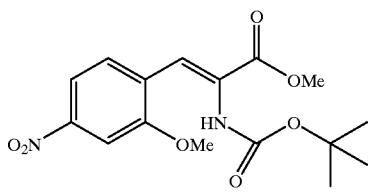

To 5 mL of dimethylformamide was added the compound of Step A (600 mg, 2.98 mmol), 2-bromo-5-nitroanisole (494 mg, 2.13 mmol), tetrabutylammonium chloride (591 mg, 2.13 mmol), sodium bicarbonate (447 mg, 5.3 mmol) and 2 mg of palladium(II) acetate. The slurry was degassed with argon, sealed and heated at 85° C. overnight. The reaction mixture was diluted with water and extracted with dichloromethane. The combined extracts were washed once with water, dried ($MgSO_4$) and concentrated to give the crude product. Chromatography on silica gel using 20/80 ethyl acetate/hexane as eluent gave 600 mg of product.

Analysis Calculated for $C_{16}H_{19}N_2O_7$: C, 54.70; H, 5.45; N, 7.97. Found: C, 54.43; H, 5.64; N, 8.09.

Step C

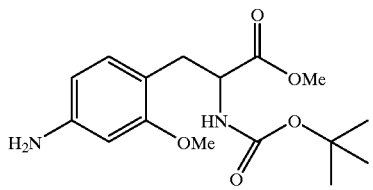

The compound of Step B was shaken in a Parr apparatus in ethanol with 5% Pd on carbon at room temperature under 5 psi $H_2$ for 16 hours. The solution was filtered and concentrated to give the product.

Step D

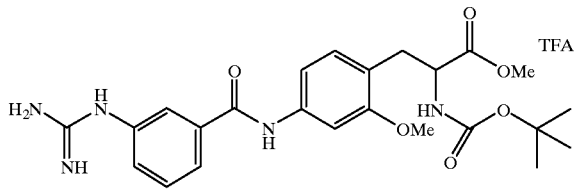

To 10 mL of dimethylformamide was added 3-guanidinobenzoic acid HCl (Example A) (299 mg, 1.387 mmol) and N-methylpiperidine (138 mg, 1.387 mmol). The reaction mixture was cooled to 0° C. and isobutylchloroformate (189 mg, 1.387 mmol) was added. After 5 minutes the compound of Step C (450 mg, 1.387 mmol) was added and the reaction mixture was stirred at room temperature overnight. The reaction mixture was concentrated and purified by HPLC on a C18 column using a $MeCN/H_2O$ gradient as eluant to give a white solid (495 mg).

Analysis Calculated for $C_{24}H_{31}N_5O_6$+TFA+0.3 $H_2O$: C, 51.62; H, 5.43; N, 11.58. Found: C, 51.27; H, 5.27; N, 11.49.

Step E

To the compound of Step D in 3 ml of methanol was added 1.0 mL of 1M LiOH. The reaction mixture was stirred at room temperature overnight. The solvent was removed under vacuum and 10 mL of water was added. The aqueous layer was acidified with trifluoroacetic acid and purified by HPLC on a C18 column using a $MeCN/H_2O$ gradient as eluant to give a white solid (89 mg).

Analysis Calculated for $C_{23}H_{29}N_5O_6$+TFA+0.6 $H_2O$: C, 50.35; H, 5.27; N, 11.74. Found: C, 50.23; H, 5.13; N, 11.71.

EXAMPLE 77

4-[[[3-[(4,5-dihydro-4-oxo-1H-imidazol-2-yl)amino]-phenyl]carbonyl]amino]-N-[(1-methylethoxy)-carbonyl]phenylalanine

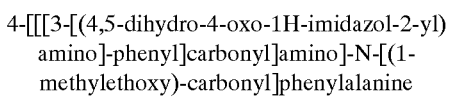

Step A

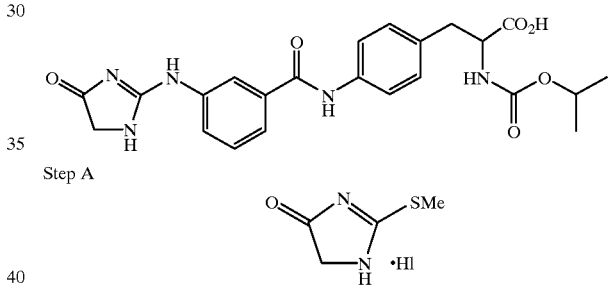

To a mixture of 2-thiohydantoin (5.5 g, 47.4 mmol) in absolute ethanol (60 mL) was added methyl iodide (3.5 mL, 56.6 mmol). The mixture was heated at reflux for 5 hours. The mixture was cooled to room temperature and concentrated in vacuo and the crude product used directly in the next step.

Step B

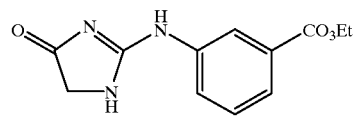

To a mixture of the thiomethyl compound from Step A (1.0 g, 3.8 mmol) in absolute ethanol (20 mL) was added ethyl 3-aminobenzoate (2.5 g, 15.3 mmol). The mixture was stirred at room temperature for 16 hours. The mixture was concentrated in vacuo and the residue chromatographed (85:14:1 $CH_2Cl_2$:MeOH:$NH_4OH$) to give the desired product (414 mg, 44%).

Step C

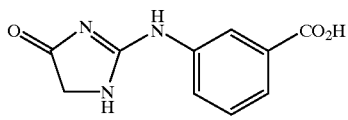

To a mixture of the ester (250 mg, 1.0 mmol) in THF (2 mL) and methanol (2 mL) was added 1.0 N NaOH solution (2 mL). The reaction solution was stirred at room temperature for 2 hours and concentrated in vacuo. The residue was suspended in water and carefully acidified to pH 4 with 1 N HCl. The solid was collected by filtration and washed with water and ether to give the desired product (190 mg, 87%).

Step D

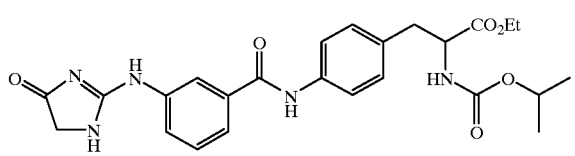

To a solution of the acid from Step C (150 mg, 0.7 mmol) in DMF (4 mL) at 0° C. was added 1-methylpiperidine (15 mL, 1.4 mmol) and isobutylchloroformate (0.088 mL, 0.7 mmol). The solution was stirred for 5 minutes and the amine from Example AE (186 mg, 0.7 mmol) was added. The mixture was stirred for 20 hours and then concentrated in vacuo. The residue was chromatographed (85:14:1 $CH_2Cl_2$:MeOH:$NH_4OH$) to give the desired product (73 mg, 22%).

Analysis Calculated for $C_{25}H_{29}N_5O_6$+0.25 $H_2O$: C, 60.05; H, 5.94; N, 14.00. Found: C, 60.10; H, 6.11; N, 14.11.

Step E

To a mixture of the ester from Step D (40 mg, 0.08 mmol) in THF (0.5 mL) and methanol (0.5 mL) was added 1.0 N NaOH solution (0.4 mL). The solution was stirred at room temperature for 3 hours and concentrated in vacuo. The residue was dissolved in water and carefully acidified to pH 4 with 1 N HCl. The white solid was collected by filtration to give the desired compound (27 mg, 71%). H NMR ($CD_3OD$) δ 7.19–7.90 (m, 8H), 4.75 (m, 1H); 4.34 (m, 1H); 3.95 (s, 2H); 3.13 (m, 1H); 2.91 (m, 1H); 1.18 (d, 3H, J=7.2 Hz); 1.12 (d, 3H, J=7.2 Hz).

EXAMPLE BJ

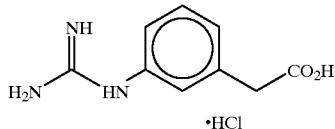

A solution of 3-aminophenylacetic acid (2.712 g, 17.9 mmol), Example AM (3.023 g, 20.6 mmol), and Hunig's base (3.6 mL, 20.6 mmol) in dioxane (30 mL)/water (15 mL) was refluxed for 16 hours under argon. With heating, a white precipitate was observed. The reaction was cooled to room temperature and the white solid filtered off. The solid was washed with 1:1 dioxane/water (3×5 mL). The solid was suspended in 15 mL of water and acidified with concentrated HCl until the solid dissolved. The solution was concentrated in vacuo and the resulting yellow residue slurried with ether. The yellow solid was collected by vacuum filtration (3.025 g, 74% yield). NMR was consistent with proposed structure.

EXAMPLE 78

Synthesis of 4-[[2-[4-[(aminoiminomethyl)amino] phenyl]-acetyl]amino]benzenepropanoic Acid, monohydrate trifluoroacetate Salt

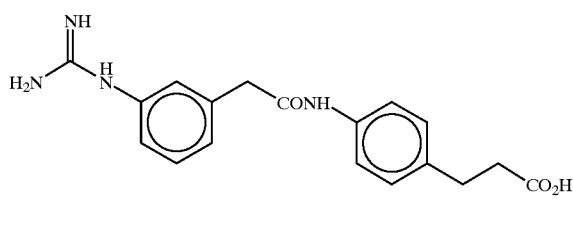

The compound of Example F (497 mg, 1.66 mmol) was coupled with the compound of Example BJ (380 mg, 1.66 mmol) according to the procedure described in Example 34. The crude product was purified by HPLC-Method 1 to give the desired product. The product was hydrolyzed under the conditions described in Example 35 and purified by HPLC-Method 1 to give a white solid.

Analysis Calculated for $C_{18}H_{20}N_4O_3$·1.5 TFA+1 $H_2O$: C, 47.64; H, 4.47; N, 10.58. Found: C, 47.56; H, 4.49; N, 10.77.

EXAMPLE 79

Synthesis of 4-[[[3-[[(cyanoimino)[(phenylmethyl)-amino]methyl]amino]phenyl]carbonyl]amino]-benzenepropanoic Acid

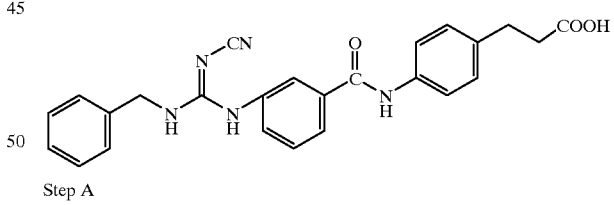

Step A

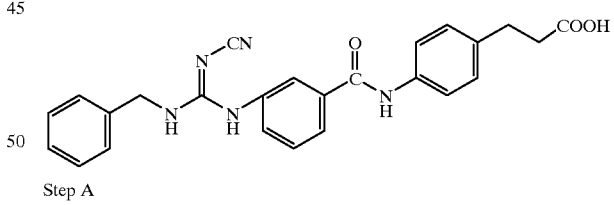

A stirred mixture of 3-amino methyl benzoate (6.04 g, 40 mmol) and dimethyl N-cyanodithioiminocarbonate (11.96 g, 80 mmol) in pyridine (70 ml) was heated at reflux under a nitrogen atmosphere for 2.5 hours. The reaction mixture was cooled to room temperature. On standing overnight at room temperature the title compound crystallized from the reaction mixture affording 6.2 g (two crops).

NMR was consistent with the proposed structure.

Step B

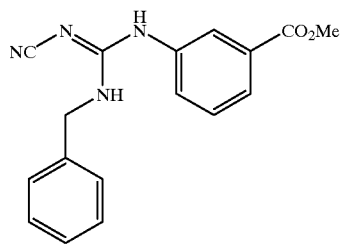

A stirred mixture of the compound from Step A (1.0 g) and benzylamine (440 mg) in ethanol (15 ml) was heated at reflux under a nitrogen atmosphere for 3 hours. The reaction mixture was cooled to room temperature. On standing overnight at room temperature a white solid was obtained and isolated by filtration (720 mg). The crude filtrate was further purified by chromatography on silica (eluant; ethyl acetate/hexane, 1:1) to afford the above compound (550 mg) as a white solid.

NMR was consistent with the proposed structure.

Step C

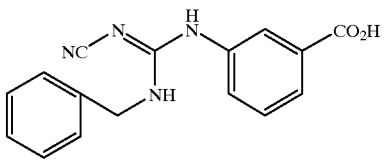

To a stirred solution of the compound from Step B (250 mg) in THF (2 ml) and MeOH (2 ml), 1N-NaOH (2 ml) was added. The reaction mixture was stirred at room temperature for 2 hours and concentrated in vacuo to afford a white solid. The residue was acidified by suspension in water followed by addition of 1N-HCl. The resultant solid was filtered, washed with diethyl ether and dried to afford the above compound (140 mg) which was used in the next step without further purification.

NMR was consistent with the proposed structure.

Step D

To a stirred solution of the product of Step C (440 mg, 1.5 mmol), in methylene chloride (20 mL) at 0° C., triethylamine (0.8 mL), DMAP (20 mg), EDCI (288 mg, 1.5 mmol) and the compound of Example F (448 mg, 1.5 mmol) were added. The reaction mixture was stirred at 0° C. for 15 minutes, allowed to attain room temperature and then stirred for another 16 hours. The reaction mixture was concentrated and the residue was dissolved in EtOAc. Washed with water, saturated aqueous $NaHCO_3$ and brine, dried over $Na_2SO_4$ and evaporated. The residue was chromatographed on silica gel using 2:1 Hexane/EtOAc as eluant to give 400 mg of pure ester as white solid. The white solid was dissolved in MeOH (4 mL) and lithium hydroxide (1 M, 2 mL) was added. The reaction mixture was stirred at room temperature overnight, and then concentrated. The residue was dissolved in water and acidified with TFA. White precipitate resulted was filtered, and washed with water and ether to give the title compound as white solid (300 mg).

Analysis Calculated for $C_{25}H_{23}N_5O_3 \cdot 0.1 H_2O$: C, 67.74; H, 5.27; N, 15.80. Found: C, 67.58; H, 5.09; N, 15.95.

EXAMPLE BA

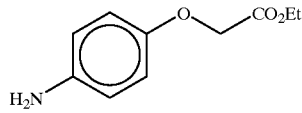

A solution of 4-aminophenol in THF (50 mL) was cooled to −30° C. Sodium hydride was added and the reaction mixture was warmed to 0° C. and kept at this temperature for 0.5 hour. The reaction mixture was cooled to −30° C. and ethyl bromoacetate was added. The reaction mixture was warmed to room temperature and stirred overnight. The solution was concentrated and partitioned between ethyl ether and water. The organic layer was washed two times with 10% NaOH solution and brine, dried over $Na_2SO_4$ and evaporated. The crude product was chromatographed on silica gel using $CHCl_3/EtOH/NH_4OH$ (95:5:1) as eluant to give 550 mg of the desired compound as a brown solid.

EXAMPLE BB

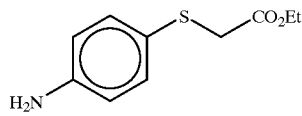

The above compound was synthesized in the same manner as described in Example BA, replacing 4-aminophenol with 4-aminothiophenol.

EXAMPLE BC

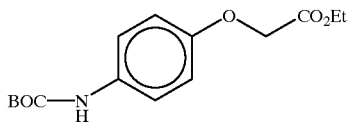

The compound of Example BB was protected with t-BOC in the same manner as described in Example X.

EXAMPLE BD

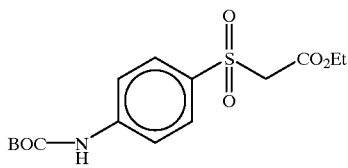

The compound of Example BC (0.9 g, 2.3 mmol) was dissolved in methanol (15 mL) and cooled to 0° C. Oxone (potassium peroxomonosulfate) (2.85 g, 4.6 mmol) in water (17 mL) was added and the solution was stirred at room temperature overnight. The solution was diluted with water, extracted with methylene chloride, dried over $Na_2SO_4$ and concentrated. Crystallization from EtOAc/Hexane resulted in 1.3 g of a white solid.

EXAMPLE BE

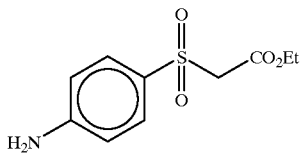

The compound of Example BD (0.8 g, 2.3 mmol) was dissolved in methylene chloride (4 mL) and cooled to 0° C. To the reaction mixture was added trifluoroacetic acid (2 mL). After 15 minutes ice bath was removed and the reaction continuously stirred for 3 hours. The reaction mixture was then concentrated to give 860 mg of desired compound.

EXAMPLE 80

Synthesis of ethyl [[4-[[[3-[(aminoiminomethyl)amino]phenyl]carbonyl]amino]phenyl]sulfonyl]acetate, monohydrate trifluoroacetate Salt

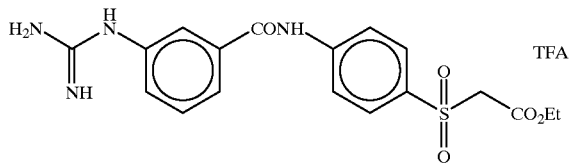

The title compound was prepared in the same manner as described in Example 34, replacing the compound of Example AA with the compound of Example BE.

Analysis Calculated for $C_{18}H_{20}N_4O_5S.1$ TFA.1 $H_2O$: C, 44.78; H, 4.32; N, 10.44. Found: C, 44.72; H, 4.03; N, 10.32.

The compounds of the following Examples were prepared by hydrolyzing the compounds of Examples 89, 90 and 80 in the same manner as described in Example 35:

EXAMPLE 81

Synthesis of [4-[[[3-[(aminoiminomethyl)amino]phenyl]-carbonyl]amino]phenoxy]acetic Acid, trifluoroacetate Salt

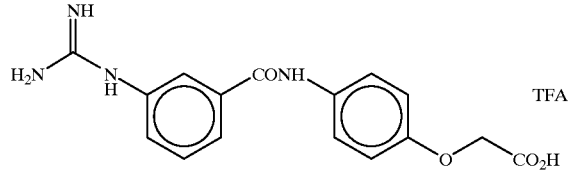

Analysis Calculated for $C_{16}H_{16}N_4O_4.1$ TFA.0.9 $H_2O$: C, 47.15; H, 4.13; N, 12.22. Found: C, 47.16; H, 3.85; N, 12.16.

EXAMPLE 82

Synthesis of [[4-[[[3-[(aminoiminomethyl)amino]phenyl]carbonyl]amino]phenyl]thio]acetic Acid, trifluoroacetate

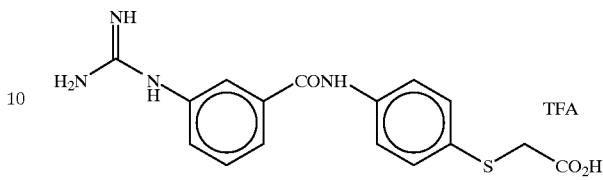

Analysis Calculated for $C_{16}H_{16}N_4O_3S.1$ TFA: C, 47.16; H, 3.34; N, 12.22. Found: C, 47.05; H, 3.61; N, 12.30.

EXAMPLE 83

Synthesis of [[4-[[[3-[(aminoiminomethyl)amino]phenyl]carbonyl]amino]phenyl]sulfonyl]acetic Acid

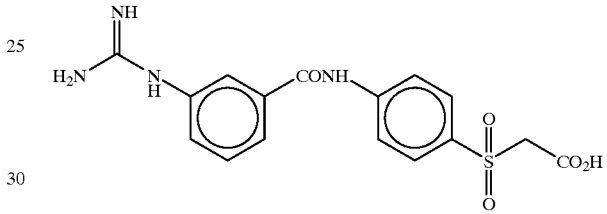

Analysis Calculated for $C_{16}H_{16}N_4O_5S.0.6$ TFA: C, 46.44; H, 3.77; N, 12.60. Found: C, 46.27; H, 3.69; N, 12.95.

EXAMPLE 84

Synthesis of [4-[2-[[3-[(aminoiminomethyl)amino]phenyl]amino]-2-oxoethyl]phenoxy]acetic Acid, trifluoroacetate Salt

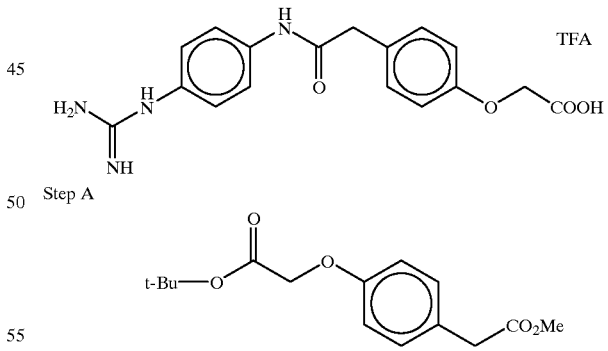

Step A

Methyl 4-hydroxyphenylacetate (2.0 g, 12.0 mmol, Aldrich) in THF (100 mL) was cooled (−30° C.) and treated with sodium hydride (50% dispersion in mineral oil, 0.6 g, 12.2 mmol) in small portions over 15 minutes. The solution was then warmed (0° C.) and stirred 30 minutes and then recooled to −30° C. To this solution was added neat t-butyl bromoacetate (2.6 g, 13.2 mmol, Aldrich) and the mixture was stirred 1 hour at −30° C. and then warmed to room temperature and stirred 1 hour. The volatile components were removed at reduced pressure on a rotary evaporator and the residue was taken up in ether (50 mL). The ether was washed with water (25 mL), 10% NaOH (25 mL) and brine (25 mL). This produced 3.4 g (100%) of the title compound.

HRMS (M+) for $C_{15}H_{20}O_5$ Calculated: 280.1311; Found: 280.1297.

Step B

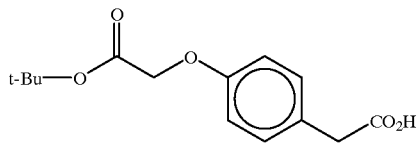

The product of Step A (0.5 g, 1.78 mmol) in THF (5 mL) was cooled (0° C.) and treated with 1N lithium hydroxide solution (1.9 mL, 1.9 mmol). The solution was warmed to room temperature and stirred for 18 hours. The volatile components were removed at reduced pressure on a rotary evaporator. The crude product was chromatographed on silica gel gradient eluting with ethyl acetate:hexane (1:19 to 1:9 containing 1% acetic acid) and produced 0.16 g (25%) of the above compound.

HRMS (M+) for $C_{15}H_{15}O_5$ Calculated: 266.1154; Found: 266.1163.

Step C

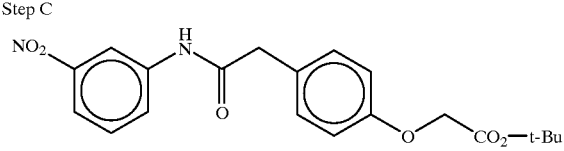

The product from Step B (0.16 g, 0.6 mmol) and 3-nitroaniline (0.2 g, 1.4 mmol, Aldrich) in methylene chloride (5 mL) was cooled (0° C.) and treated with 1-(3-dimethylaminopropyl)-3-ethylcarbodiimide hydrochloride (0.2 g, 1.04 mmol, Aldrich) and N-methylmorpholine (0.15 mL, 1.4 mmol, Aldrich). The solution was warmed to room temperature and stirred 18 hours. The mixture was poured into water and extracted with ethyl acetate (2×25 mL). The combined extracts were washed with water (2×10 mL) and saturated brine (10 mL), and dried over $MgSO_4$. The volatile components were removed at reduced pressure on a rotary evaporator to produce 0.19 g (82%) of the above compound.

HRMS (M+) for $C_{20}H_{22}N_2O_6$ Calculated: 386.1478; Found: 386.1492.

Step D

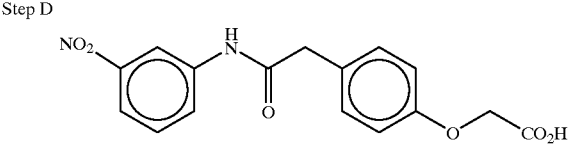

The product of Example 84C (0.19 g, 0.49 mmol) in methylene chloride (5 mL) was cooled (0° C.) and treated with trifluoroacetic acid (0.5 mL). The solution was warmed to room temperature and stirred 3 hours. The volatile components were removed at reduced pressure on a rotary evaporator. This produced 0.14 g (86%) of the title compound.

HRMS (M+) for $C_{16}H_{14}N_2O_6$ Calculated: 330.0851; Found: 330.0832.

Step E

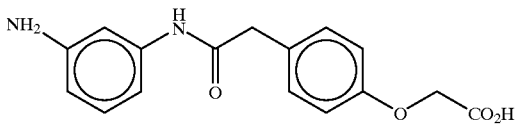

The product from Example 84D (0.14 g, 0.42 mmol) was subjected to the reaction conditions described for the preparation of Example 68B. This produced 0.11 g (88%) of the title compound.

HRMS (M+) for $C_{16}H_{16}N_2O_4$ Calculated: 300.1110; Found:

Step F

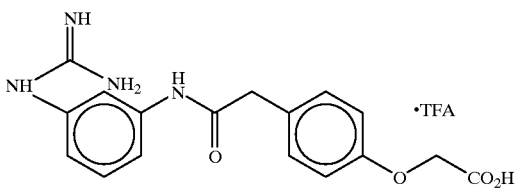

A stirred solution of the product of Example 84E (0.11 g, 0.37 mmol), diisopropylethylamine (0.09 mL) and pyrazole-1-carboxamidine hydrochloride (73 mg, 0.5 mmol) in dioxane (3 mL) and water (0.5 mL) was heated at reflux for 3 hours. After cooling to room temperature, the solvents were removed at reduced pressure and the residue was chromatographed (reverse phase HPLC, gradient elution with water/acetonitrile/trifluoroacetic acid). This produced 0.028 g (16%) of the title compound.

ESI MS (free base MH+) for $C_{17}H_{19}N_4O_4$; Calculated: 343; Found: 343.

EXAMPLE 85

Synthesis of 2-[4-[[[3-[(aminoiminomethyl)amino]phenyl]carbonyl]amino]phenoxy]propanoic Acid, trifluoroacetate Salt

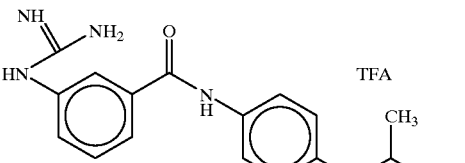

Step A

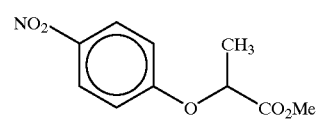

To a stirred and cooled (0° C.) solution of 4-nitrophenol (0.56 g, 4 mmol, Aldrich), methyl DL-lactate (0.37 g, 3.6 mmol) and diethyl azodicarboxylate (0.64 mL, 4 mmol) in THF (50 mL) was added portionwise triphenylphosphine (1.05 g, 4 mmol). After 1 hour, the mixture was warmed to room temperature and stirred for 18 hours. The volatile components were removed at reduced pressure and the residue taken up in ethyl acetate (100 mL). The solution was washed with 5% aqueous sodium carbonate (4×25 mL), water (25 mL), brine (25 mL) and dried over magnesium sulfate. The volatile components were removed at reduced pressure on a rotary evaporator and the crude product was chromatographed on silica gel eluting with ether which produced 1.06 g of a 3:1 mixture of the above compound contaminated with 1,2-dicarbethoxyhydrazine.

HRMS (M+) for $C_{10}H_{11}NO_5$ Calculated: 225.0637; Found: 225.0636.

Step B

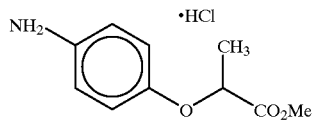

The crude product from Example 85A (1.06 g) was subjected to the reaction conditions described for the preparation of Example 68B. The crude product was treated with methanolic HCl (5 mL) and then the volatile components were removed at reduced pressure. The residue was triturated with ether which produced 0.34 g of the title compound.

HRMS (free base M+) for $C_{10}H_{13}NO_3$ Calculated: 195.0895; Found: 195.0899.

Step C

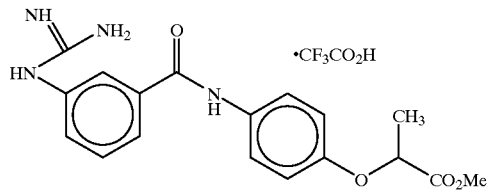

To a stirred and cooled (0° C.) solution of 3-guanidinobenzoic acid hydrochloride (0.093 g, 0.43 mmol) and N-methylmorpholine (0.05 g, 0.43 mmol) in DMF (3 mL) was added isobutyl chloroformate (0.06 mL, 0.43 mmol). The mixture was stirred for 30 minutes. To this solution was added a solution of the product from Step B (0.1 g, 0.43 mmol) and N-methylmorpholine (0.05 g, 0.43 mmol) in DMF (2 mL). The reaction mixture was then allowed to warm to room temperature and stirred for 18 hours. The volatile components were removed at reduced pressure and the residue was chromatographed (reverse phase HPLC, gradient elution with water/acetonitrile/trifluoroacetic acid). This produced 120 mg (59%) of the above compound.

APCI MS (free base MH+) for $C_{18}H_{21}N_4O_4$ Calculated: 357; Found: 357.

Step D

The product of Step C (0.05 g, 0.11 mmol) in methyl alcohol (1 mL) was cooled (0° C.) and treated with 1N lithium hydroxide solution (0.22 mL, 0.22 mmol). The solution was warmed to room temperature and stirred for 18 hours. The volatile components were removed at reduced pressure on a rotary evaporator. The crude product was chromatographed (reverse phase HPLC, gradient elution with water/acetonitrile/trifluoroacetic acid). This produced 50 mg (100%) of the above compound.

APCI MS (free base MH+) for $C_{17}H_{19}N_4O_4$ Calculated: 343; Found: 343.

EXAMPLE 86

Synthesis of α-[4-[[[3-[(aminoiminomethyl)amino]phenyl]carbonyl]amino]phenoxy]benzeneacetic Acid, trifluoroacetate Salt

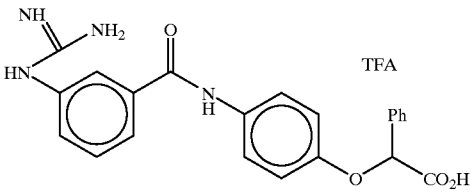

Step A

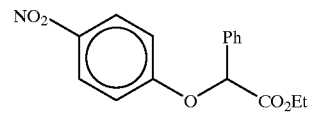

Ethyl DL-mandelate (0.65 g, 0.36 mmol) was subjected to the reaction conditions described in Example 85, Step A to produce 1.2 g of a mixture of the above compound contaminated with 1,2-dicarbethoxyhydrazine.

HRMS (M+) for $C_{16}H_{15}NO_5$ Calculated: 301.0950; Found: 301.0977.

Step B

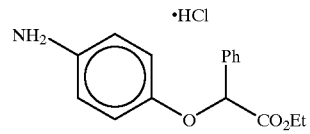

The crude product from Step A (1.2 g) in absolute ethanol (10 mL) was treated with tin (II) chloride (2.4 g, 12.7 mmol) and then heated at 70° C. for 1 hour. The mixture was then cooled to room temperature and treated with saturated sodium bicarbonate solution (25 mL) and then poured into water (100 mL). The aqueous solution was then extracted with ethyl acetate (2×25 mL) and then poured into water (100 mL). The aqueous solution was then extracted with ethyl acetate (2×25 mL) and the combined extracts were washed with water (2×10 mL), brine (10 mL) and then dried over magnesium sulfate. The volatile components were removed at reduced pressure on a rotary evaporator. The residue was treated with methanolic HCl (5 mL) and the volatile components were removed at reduced pressure. The residue was triturated with ether which produced 0.55 g of the above compound.

HRMS (free base M+) for $C_{16}H_{17}NO_3$ Calculated: 271.1208; Found: 271.1223.

Step C ethyl α-[4-[[[3-[(aminoiminomethyl)amino]phenyl]carbonyl]amino]phenoxy]benzeneacetate, trifluoroacetate Salt

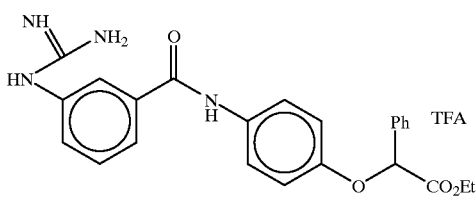

The product from Step B (0.13 g, 0.43 mmol) was subjected to the reaction conditions described in Example 85, Step C to produce 0.11 g (47%) of the above compound.

APCI MS (free base MH+) for $C_{24}H_{25}N_4O_4$ Calculated: 433; Found: 433.

Step D

The product from Step C (0.05 g, 0.09 mmol) was subjected to the reaction conditions described in Example 85, Step D to produce 0.03 g (64%) of the above compound.

APCI MS (free base MH+) for $C_{22}H_{21}N_4O_4$ Calculated: 405; Found: 405.

EXAMPLE 87

4[[[3-[(aminoiminomethyl)amino]-4-chlorophenyl]carbonyl]amino]-N-[(1-methylethoxy)carbonyl]phenylalanine

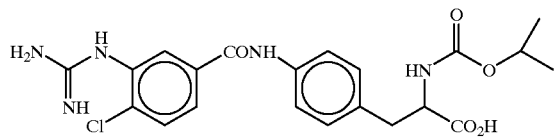

Step AA
Preparation of

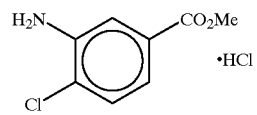

To a stirred suspension of 3-amino-4-chlorobenzoic acid (25.0 g, 157 mmol) in MeOH (300 ml) at 0° C., hydrogen chloride gas was added until the methanolic solution was saturated. The reaction mixture was stirred at 0–5° C. for 30 minutes, allowed to attain room temperature, and then stirred for a further 4 days.

The reaction mixture was concentrated in vacuo and the resulting white solid triturated with diethyl ether to afford the above compound; 26.2 g as a white solid.

NMR was consistent with the assigned structure.

Step AAA
Preparation of

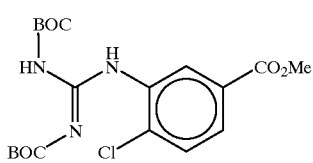

To a solution of Example AZ and (24.8 g, 90 mmol) methyl-3-amino-4-chlorobenzoate (20 g, 90 mmol) in dimethylformamide (120 ml) and triethylamine (45 ml) at 0° C. mercury II chloride (30.1 g, 111 mmol) was added. The reaction mixture was stirred for 15 minutes at 0° C., allowed to attain room temperature and stirred for a further 2 hours. The reaction mixture was diluted with ethyl acetate (600 ml) and the resulting slurry filtered under reduced pressure. The filtrate was concentrated, to afford an oily gum which was purified by chromatography on silica (eluent: ethyl acetate/heptane 20:80) to afford the above compound (8.6 g) as a white solid.

NMR was consistent with the assigned structure.

Step A

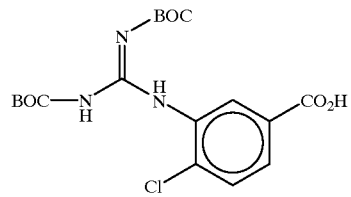

The product of Step AAA was dissolved in MeOH (3 mL) and 1 M NaOH (14 mL) was added at room temperature. The reaction was stirred at room temperature for 2 hours. The reaction was concentrated in vacuo and the residue dissolved in water, washed with ether. The aqueous layer was acidified to pH=3 with 1N HCl. A white precipitate formed, was filtered and washed with water and ether and dried to give 1.2 g white solid. NMR was consistent with the proposed structure.

Step B

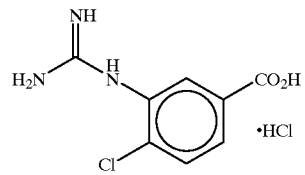

To a solution of the product of Step A (550 mg, 1.33 mmol) in $CH_2Cl_2$ (4 mL) was added TFA (1 mL) at 0° C. The ice bath was removed after the addition and the reaction was stirred at room temperature for 2 hours. The reaction was concentrated in vacuo to give a colorless oil. To this was added 4N HCl solution in dioxane (2 mL) and white precipitate formed. The solution was concentrated in vacuo to afford 280 g of the desired product as a white solid. NMR was consistent with the proposed structure.

Step C

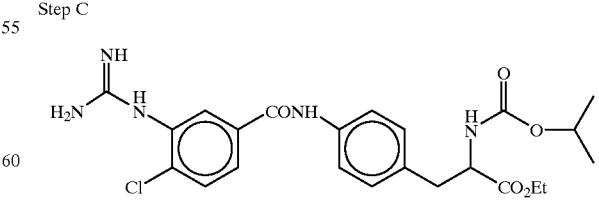

A solution of the product of Step B (280 mg, 1.1 mmol) and 1-methyl piperidine (0.14 mL, 1.1 mmol) in DMF (5 mL) was cooled to 0° C. and isobutyl chloroformate (0.14 mL, 1.1 mmol) was added under argon. The reaction was allowed to stir for 5 minutes before adding a solution of Example AE (328 mg, 1.1 mmol) in DMF (2 mL). The reaction was allowed to warm slowly to room temperature over 16 hours. The solution was concentrated in vacuo and the residue purified by HPLC to give the desired product as a yellow gummy oil (190 mg).

Analysis Calculated for $C_{23}H_{28}N_5O_5Cl.1.5$ TFA: C, 47.24; H, 4.50; N, 10.60. Found: C, 47.23; H, 4.49; N, 10.97. M+=489.

Step D

The compound of Step C (170 mg, 0.34 mmol) was dissolved in MeOH (2 mL) and 1 M LiOH (1 mL) was added at room temperature. The reaction was stirred for 23 hours. The solution was concentrated in vacuo and the residue purified by HPLC to give the desired product as a white solid (130 mg).

Analysis Calculated for $C_{21}H_{24}N_5O_5Cl.1.4$ TFA: C, 45.99; H, 4.12; N, 11.27. Found: C, 45.95; H, 4.25; N, 11.29. M+461.

EXAMPLE 89

Synthesis of ethyl [4-[[[3-[(aminoiminomethyl)amino]phenyl]carbonyl]amino]phenoxy]acetate, trifluoroacetate Salt

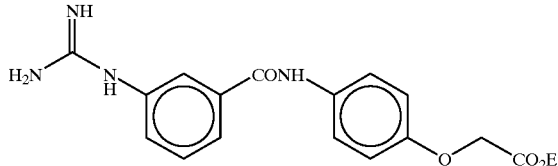

The title compound was prepared under similar conditions as described in Example 34, replacing the compound of Example AA with the compound of Example BA.

Analysis Calculated for $C_{18}H_{20}N_4O_4.1.1$ TFA.0.7 $H_2O$: C, 49.07; H, 4.59; N, 11.33. Found: C, 49.26; H, 4.23; N, 11.09.

EXAMPLE 90

Synthesis of ethyl[[4-[[(3-[(aminoiminomethyl)amino]phenyl]carbonyl]amino]phenyl]thio]acetic Acid, trifluoroacetate

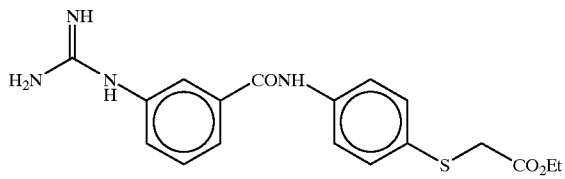

The title compound was prepared in a similar manner as described in Example 34, replacing the compound of Example AA with the compound of Example BB.

Analysis Calculated for $C_{18}H_{20}N_4O_3S$: C, 48.84; H, 4.43; N, 11.39. Found: C, 48.85; H, 4.12; N, 11.50.

EXAMPLE 91

Preparation of: 4-[[3-[(aminoiminomethyl)amino]phenyl]methoxy]-N-[(1,1-dimethylethoxy)carbonyl]phenylalanine

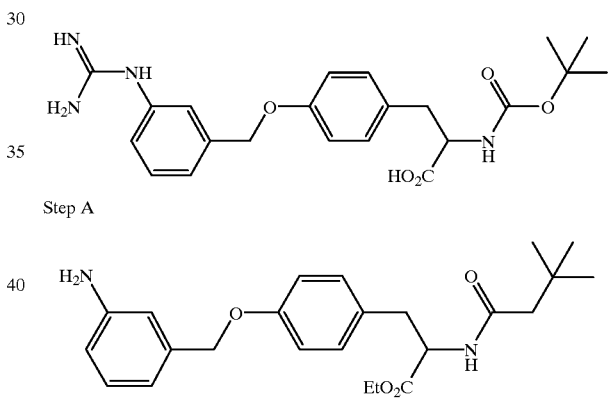

Step A

The n-t-BOC ethyl ester product of Example 11, Step A can be dissolved in absolute EtOH and reduced using substantially the quantities and procedure of Example 11, Step D to obtain the N-t-BOC aniline ethyl ester that can be isolated in substantially pure form by prep rphplc.

Step B

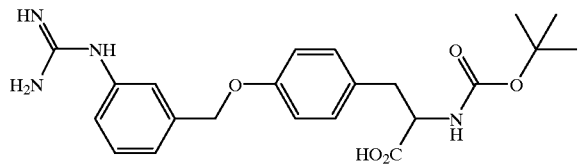

The N-t-BOC aniline ethyl ester of Step A can be converted to the guanidino—ethyl ester derivative using substantially the quantities, proportions and procedure of Example 11, Step E and subsequently hydrolyzed to the guanidino—acid derivative using the hydrolysis procedure of Example 11, Step E.

EXAMPLE 92A

Preparation of: 4-[[3-[(aminoiminomethyl)amino]phenyl]methoxy]-N-[(1,1-dimethylethoxy)-carbonyl]phenylalanine

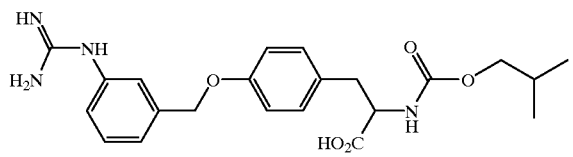

The title compound can be prepared using the methodology of Example 11, substituting an equivalent amount of isobutylchloroformate (Aldrich) for n-butanesulfonyl chloride in Step C.

EXAMPLE 92B

Preparation of: 4-[[3-[(aminoiminomethyl)amino]phenyl]methoxy]-N-(butylamino)carbonyl]phenylalanine

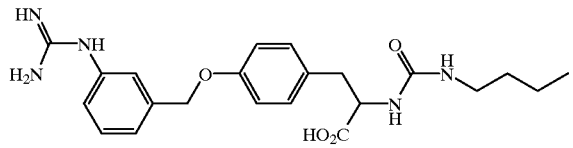

The above compound can be prepared using the methodology of Example 11, substituting an equivalent amount of n-butyl isocyanate (Aldrich) for n-butanesulfonyl chloride in Step C.

EXAMPLE 93

Preparation of: 4-[[3-[(aminoiminomethyl)amino]phenyl]methoxy]-N-[[(1,1-dimethylethyl)amino]-carbonyl]phenylalanine

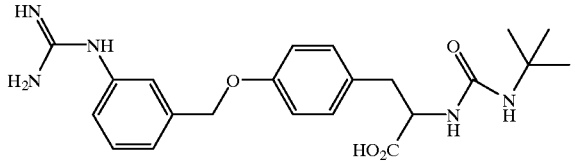

The above compound can be prepared using the methodology of Example 11, substituting an equivalent amount of t-butyl isocyanate (Aldrich) for n-butanesulfonyl chloride in Step C.

EXAMPLE 94

Preparation of: 4-[[3-[(aminoiminomethyl)amino]phenyl]-methoxy]-N-(phenylamino)carbonyl]phenylalanine

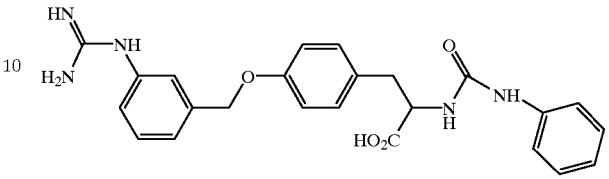

The above compound can be prepared using the methodology of Example 11, substituting an equivalent amount of phenyl isocyanate (Aldrich) for n-butanesulfonyl chloride in Step C.

EXAMPLE 95

Preparation of: 4-[[3-[(aminoiminomethyl)amino]phenyl]-methoxy]-N-(3,3-dimethyl-1-oxobutyl)phenylalanine

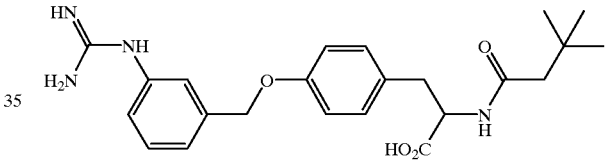

The above compound can be prepared using the methodology of Example 11, substituting an equivalent amount of isovaleryl chloride (Aldrich) for n-butanesulfonyl chloride in Step C.

EXAMPLE 96

Preparation of: N-acetyl-4-[[3-[(aminoiminomethyl)amino]phenyl]methoxy]phenylalanine

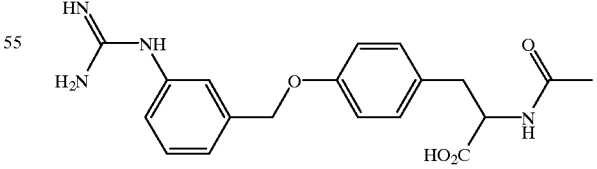

The above compound can be prepared using the methodology of Example 11, substituting an equivalent amount of acetyl chloride (Aldrich) for n-butanesulfonyl chloride in Step C.

EXAMPLE 97

Preparation of: N-[(3-methylpropoxy)carbonyl]-4-[[3-[(3,4,5,6-tetrahydro-2H-azepin-7-yl)amino]phenyl]methoxy]phenylalanine

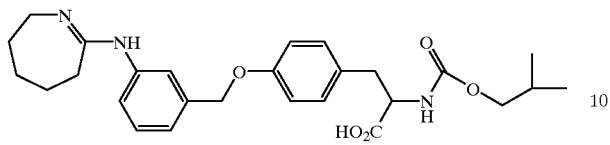

Step A.

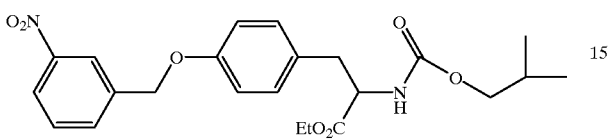

The above compound can be prepared using the procedure of Example 11 and substituting an equivalent amount of isobutyl chloroformate for butane sulfonylchloride in Example 11, Step C.

Step B.

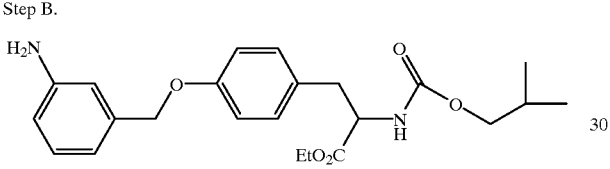

The nitro-tyrosine derivative of Step A can be reduced to the aniline using substantially equivalent amounts and the procedure of Example 11, Step D and substituting the product of Step A for the product of Example 11, Step C.

Step C.

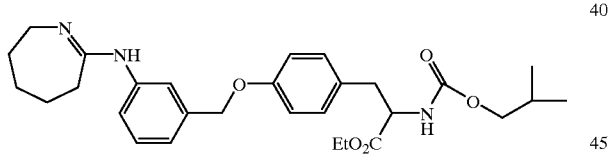

The above compound can be prepared by reacting essentially equivalent amounts of 1-aza-2-methoxy-1-cycloheptene with the anilino-tyrosine derivative prepared in Step B in a suitable solvent (EtOH, dimethylacetamide or dimethylformamide) until essentially complete reaction is obtained. The volatiles can be removed under reduced pressure and the desired product may be obtained by preparative RPHPLC.

Step D.

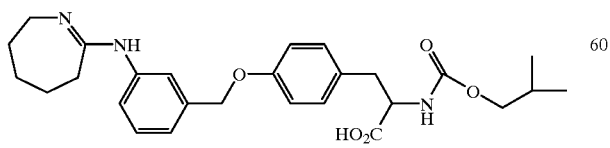

The ethyl ester obtained in Step C can be converted to the acid derivative using substantially the hydrolysis conditions of Example 11, Step E. The ethyl ester obtained in Step C can be dissolved in water:dioxane and aqueous lithium hydroxide added to pH 11. The reaction can be monitored by analytical RPHPLC until complete. The product can then be isolated by preparative RPHPLC.

EXAMPLE 98

Preparation of: N-(butylsulfonyl)-4-[[3-[(3,4,5,6-tetrahydro-2H-azepin-7-yl)amino]phenyl]methoxy]phenylalanine

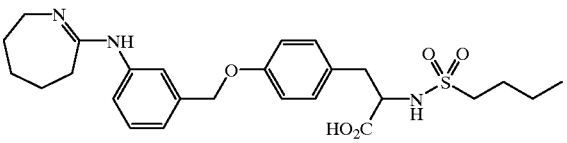

The above compound can be prepared using the procedures of Example 97 and using the procedure of Example 11, Step C to prepare the starting material (m-nitrobenzyl-N-n-butanesulfonyl tyrosine derivative). The product can be isolated using preparative RPHPLC.

EXAMPLE 99

Preparation of: N-(butylamino)carbonyl]-4-[[3-[(3,4,5,6-tetrahydro-2H-azepin-7-yl)amino]phenyl]methoxy]phenylalanine

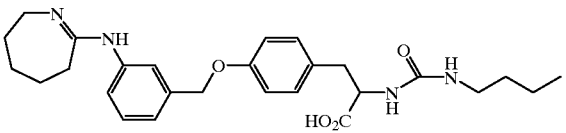

The above compound can be prepared using the procedures of Example 97 and substituting n-butyl A isocyanate for n-butanesulfonyl chloride in Example 11, Step C. The product can be isolated using preparative RPHPLC.

EXAMPLE 100

4-[[[3-[(aminoiminomethyl)amino]phenyl]carbonyl]amino]benzene-1,2-dipropanoic Acid, trifluoroacetate Salt

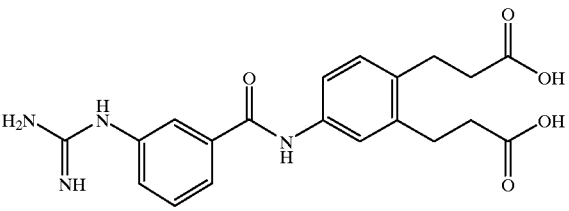

Step A

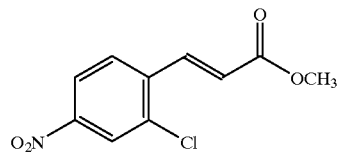

To 2-chloro-5-nitro cinnamic acid (912 mg, 4 mmol) in DMF (4 ml) was added NaHCO$_3$ (1.2 g) and MeI (1.1 g, 8 mmol) and the mixture stirred at room temperature overnight. The solvent was removed and the residue dissolved in CHCl$_3$. The solution was washed with water, dried and concentrated to provide the ester (800 mg). $^1$H NMR was consistent with the proposed structure.

Step B

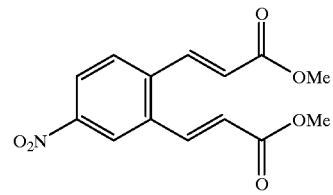

Methyl 2-chloro-5-nitrocinnamate acid (0.8 g, 3.3 mmol), methyl acrylate (450 mg, 5.2 mmol), tetra-n-butylammonium chloride (920 mg, 3.3 mmol), NaHCO$_3$ (880 mg) and cat. Pd(OAc)$_2$ (40 mg) were stirred in DMF (16 mL) at 80° C. overnight. The mixture was cooled and the solvent removed. Flash chromatography (toluene/EtOAc) provided of the desired product (620 mg). $^1$H NMR was consistent with the proposed structure.

Step C

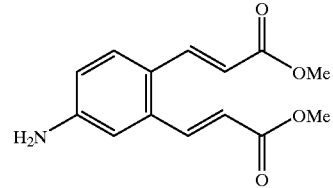

The product from Step B (620 mg, 2.1 mmol) and tin(II) chloride dihydrate (675 mg, 3 mmol) were stirred in 2:1 MeOH/concentrated HCl (19 ml) at 80° C. for 1 hour. The mixture was cooled and filtered. The filtrate was concentrated and purified by flash chromatography (EtOAc/toluene/NH$_4$OH) to provide the desired compound (310 mg). $^1$H NMR was consistent with the proposed structure.

Step D

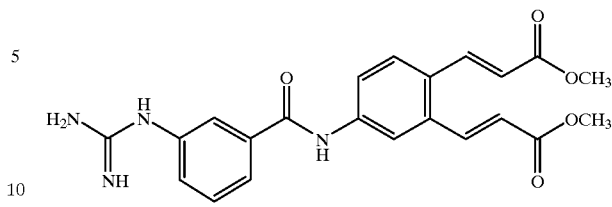

To the compound of Example A (3-guanidinobenzoic acid hydrochloride, 300 mg, 1.4 mmol) in DMF (2 ml) at 0° C. was added 1-hydroxybenzotriazole hydrate (HOBT, 200 mg, 1.5 mmol) and 1-(3-dimethylaminopropyl)-3-ethylcarbodiimide hydrochloride (EDCI, 300 mg, 1.6 mmol) and the mixture stirred at 0° C. for 3 hours. The compound from Step C (308 mg, 1.2 mmol) was added and the mixture was stirred at room temperature for 48 hours. Purification by flash chromatography (MeOH/CHCl$_3$) and reverse phase HPLC (CH$_3$CN/H$_2$O/TFA) provided the desired compound. $^1$H NMR and MS were consistent with the proposed structure.

Analysis calculated for C$_{22}$H$_{22}$N$_4$O$_5$.1.5 TFA: C, 50.60; H, 3.99; N, 9.44. Found: C, 50.50; H, 4.18; N, 9.35.

Step E

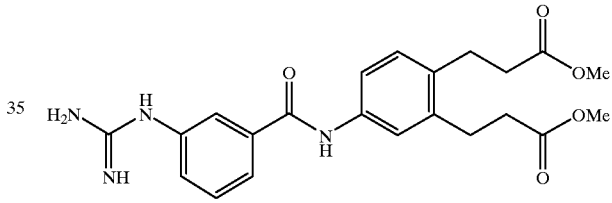

The product of Step D (300 mg) was hydrogenated at 5 psi H$_2$ in EtOH/MeOH/THF using 130 mg of 5% Pd/C as catalyst. Filtration, concentration, and purification by reverse phase HPLC (CH$_3$CN/H$_2$O/TFA) provided of the desired compound (260 mg). $^1$H NMR and MS were consistent with the proposed structure.

Step F

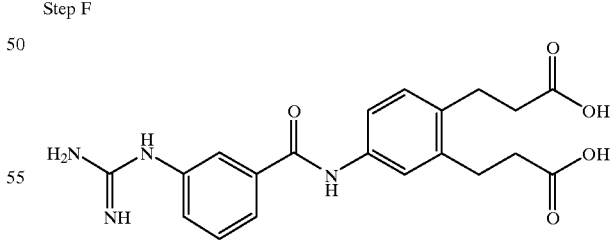

The product of Step E (200 mg, 0.47 mmol) was saponified as described in Example 35 to provide, after reverse phase HPLC (CH$_3$CN/H$_2$O/TFA), the desired compound. $^1$H NMR and MS were consistent with the proposed structure.

Analysis calculated for C$_{20}$H$_{22}$N$_4$O$_5$.1.5 TFA: C, 48.51; H, 4.16; N, 9.84. Found: C, 48.99; H, 4.20; N, 10.00.

EXAMPLE 101

A:

4-[[[3-[(aminoiminomethyl)amino]phenyl]carbonyl]
amino]-2-carboxybenzenepropanoic Acid, bis
(trifluoroacetate) Salt

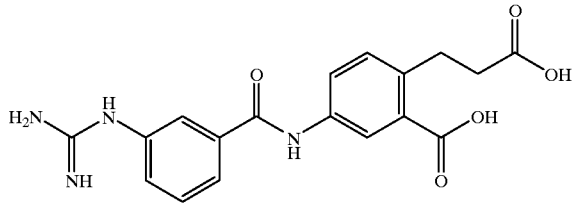

B:

4-[[[3-[(aminoiminomethyl)amino]phenyl]carbonyl]
amino]-2-methoxycarbonyl)benzenepropanoic Acid,
bis(trifluoroacetate) Salt

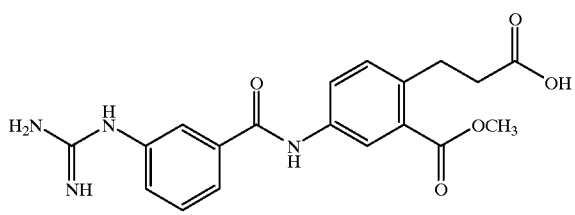

Step A/B

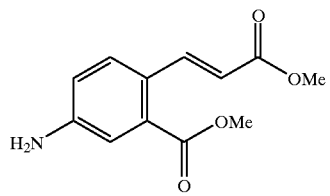

The desired compound was synthesized from methyl 2-bromo-5-nitrobenzoate using the procedure described in Example 100, Steps B and C. $^1$H NMR was consistent with the proposed structure.

Step C

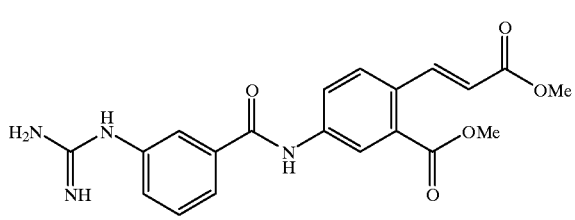

The compound of Step A/B and 3-guanidinobenzoic acid hydrochloride were coupled under the conditions described in Example 76, Step D to provide, after reverse phase HPLC (CH$_3$CN/H$_2$O/TFA), the desired compound. $^1$H NMR was consistent with the proposed structure.

Analysis calculated for $C_{20}H_{19}N_4O_5$·1.5 TFA: C, 48.77; H, 3.65; N, 9.89. Found: C, 48.43; H, 3.88; N, 9.80.

Step D

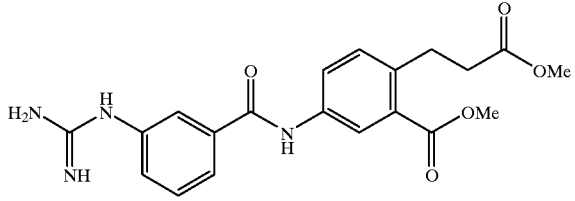

The product of Step C (80 mg) was hydrogenated using the conditions described in Example 100 Step E. Purification by reverse phase HPLC (CH$_3$CN/H$_2$O/TFA) provided the desired compound (75 mg). $^1$H NMR and MS were consistent with the proposed structure.

Analysis calculated for $C_{20}H_{24}N_4O_5$·2.0 TFA: C, 48.77; H, 3.65; N, 9.89. Found: C, 48.43; H, 3.88; N, 9.80.

Step E

A: 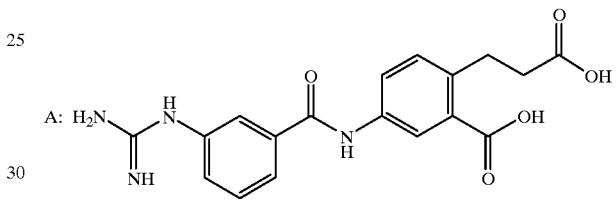

B: 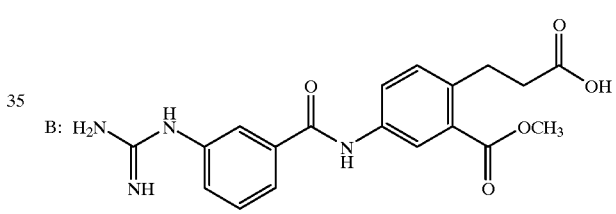

The product of Step D (75 mg) was saponified as described in Example 35. Purification by reverse phase HPLC (CH$_3$CN/H$_2$O/TFA) provided 32 mg of A and 36 mg of B. $^1$H NMR was consistent with the proposed structures A: Analysis calculated for $C_{18}H_{18}N_4O_5$·2.2 TFA: C, 43.31; H, 3.28; N, 9.02. Found: C, 43.22; H, 3.56; N, 9.03.

B: Analysis calculated for $C_{19}H_{20}N_4O_5$·2.0 TFA: C, 45.11; H, 3.62; N, 9.15. Found: C, 45.38; H, 3.18; N, 9.43.

EXAMPLE 102

2-carboxy-4-[[[3-[(1,4,5,6-tetrahydropyrimidin-2-
yl)-amino]phenyl]carbonyl]amino]benzenepropanoic
Acid, trifluoroacetate Salt

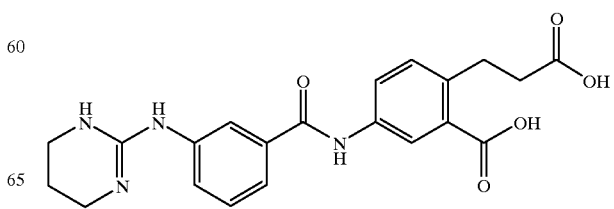

115

-continued

Step A

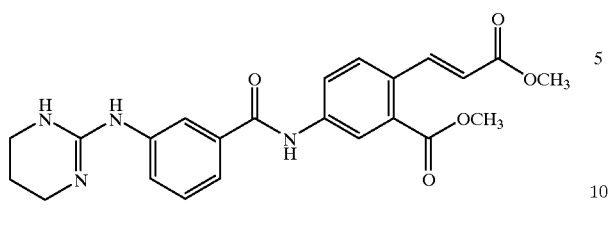

The desired compound was prepared from the compound of Example 101 Step A/B (270 mg, 1.1 mmol) and the compound of Example 130 (280 mg, 1.1 mmol) using the conditions described in Example 100, Step D. Purification by flash chromatography (MeOH/CHCl$_3$) provided the desired (270 mg). $^1$H NMR and MS were consistent with the proposed structure.

Analysis calculated for C$_{23}$H$_{24}$N$_4$O$_5$·1.2 TFA: C, 53.22; H, 4.43; N, 9.77. Found: C, 53.02; H, 4.20; N, 9.69.

Step B

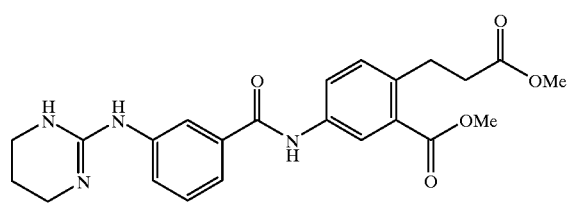

The product of Step A (160 mg) was hydrogenated using the conditions described in Example 100 Step E, using MeOH, THF, TEA and NH$_4$OH to solubilize the starting material. Purification by flash chromatography (CHCl$_3$/MeOH) provided the desired compound. $^1$H NMR was consistent with the proposed structure.

Analysis calculated for C$_{23}$H$_{26}$N$_4$O$_5$·1.0 TFA: C, 54.35; H, 4.93; N, 10.14. Found: C, 54.05; H, 5.21; N, 10.10.

Step C

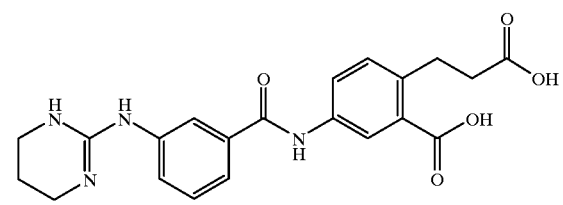

The product of Step B (600 mg) was saponified as described in Example 35. Purification by reverse phase HPLC (CH$_3$CN/H$_2$O/TFA) provided the diacid (50 mg). $^1$H NMR and MS were consistent with the proposed structure.

Analysis calculated for C$_{21}$H$_{22}$N$_4$O$_5$·1.3 TFA: C, 50.74; H, 4.20; N, 10.03. Found: C, 50.72; H, 4.14; N, 9.93.

116

EXAMPLE 103

(±) 4-[[[3-[3-amino-1H-1,2,4-triazol-5-yl)amino)phenyl]carbonyl]amino]-N-[(1-methylethoxy)carbonyl)phenylalanine, trifluoroacetate Salt

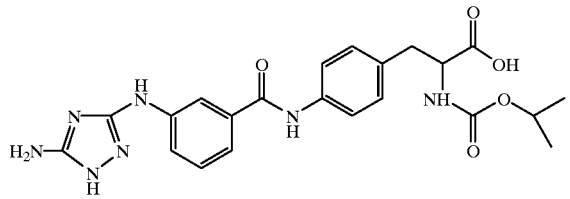

Step A

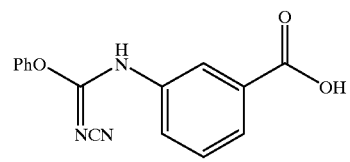

A solution of 3-aminobenzoic acid (2.0 g, 14.6 mmol) and diphenyl cyanocarbonimidate (3.48 g, 14.6 mmol) in isopropanol (25 mL) was stirred at room temperature for 18 hours. The resulting precipitate was filtered and washed with cold isopropanol and recrystallized from acetonitrile to produce 1.7 g (41.4%) of the desired compound. $^1$H NMR was consistent with the proposed structure.

HRMS (M+) for C$_{15}$H$_{11}$N$_3$O$_3$ calculated: 281.0800; found: 281.0815.

Step B

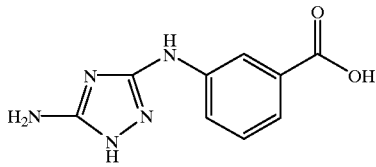

The product from Step A (0.66 g, 2.35 mmol) and hydrazine hydrate (55% hydrazine) (0.15 g, 2.5 mmol) in methanol (20 mL) was stirred at room temperature for 18 hours. The resulting precipitate was filtered and washed with cold isopropanol to produce 0.6 g (77.4%) of the desired compound. $^1$H NMR was consistent with the proposed structure.

HRMS (M+) for C$_9$H$_9$N$_5$O$_2$ calculated: 219.0756; found: 219.0749.

Step C

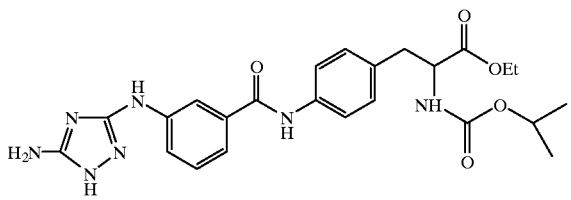

The product from Step B (0.1 g, 0.6 mmol) and the product from Example AE (0.1 g, 0.45 mmol) in DMF (2.55 mL) were cooled to 0° C. and treated with 1-(3-dimethylaminopropyl)-3-ethylcarbodiimide hydrochloride (0.09 g, 0.45 mmol) and N-methylmorpholine (0.05 mL, 0.45 mmol). The solution was warmed to room temperature and stirred 18 hours. The mixture was poured into water and extracted with ethyl acetate (2×25 mL). The combined extracts were washed with water (2×10 mL) and saturated brine (10 mL), and dried over MgSO$_4$. The volatile components were removed at reduced pressure on a rotary evaporator. The residue was purified by reverse phase HPLC (CH$_3$CN/H$_2$O/TFA) affording 70 mg (31.1 %) of the desired compound. $^1$H NMR was consistent with the proposed structure.

HRMS (M+, free base) for C$_{24}$H$_{29}$N$_7$O$_5$; calculated: 495.2230; found: 495.2244.

Step D

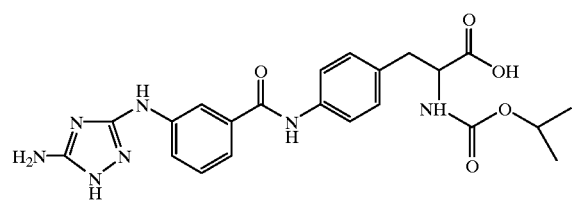

The product of Step C (0.05 g, 0.08 mmol) was saponified as described in Example 35 to provide, after reverse phase HPLC (CH$_3$CN/H$_2$O/TFA), 40 mg (87.5 %) of the title compound. $^1$H NMR was consistent with the proposed structure.

APCI-MS (MH+, free base) for C$_{22}$H$_{26}$N$_7$O$_5$; calculated: 468; found: 468.

EXAMPLE 104

(±) 4-[[[3-[(5-amino-1,2,4-oxadiazol-3-yl)amino]phenyl]carbonyl]amino]-N-[(1-methylethoxy)carbonyl]phenylalanine, trifluoroacetate Salt

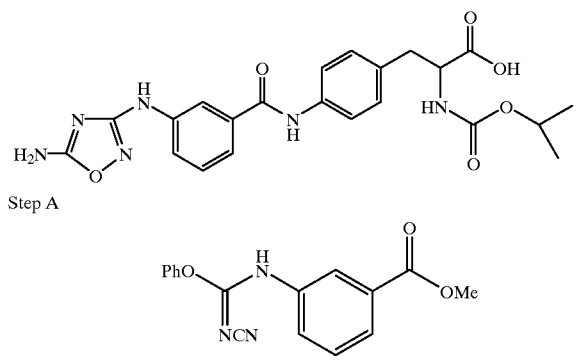

Step A

Methyl 3-aminobenzoate (2.2 g, 14.6 mmol, Lancaster) was subjected to the reaction conditions described in Example 103, Step A to produce 2.2 g (51%) of the desired compound. $^1$H NMR was consistent with the proposed structure.

HRMS (M+) for C$_{15}$H$_{20}$O$_5$ calculated: 295.0957; found: 295.0957.

Step B

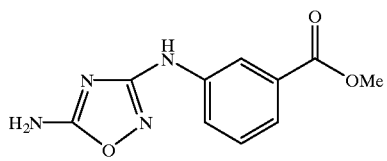

The product from Step A (1.0 g, 3.39 mmol) in methanol (25 mL) was treated with a solution of hydroxylamine hydrochloride (0.24 g, 3.4 mmol), 50% sodium hydroxide (0.28 g, 3.4 mmol) and water (2 mL) and the mixture stirred at room temperature for 18 hours. The mixture was concentrated and the resulting precipitate suspended in water, filtered and washed with cold water and cold isopropanol to produce 0.78 g (98%) of a mixture containing the desired compound along with an isomeric oxadiazole. $^1$H NMR was consistent with the proposed structures.

HRMS (M+) for C$_{10}$H$_{10}$N$_4$O$_3$ calculated: 234.0753; found: 234.0752.

Step C

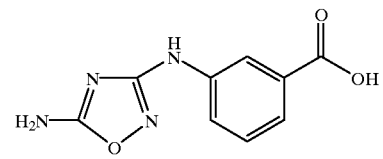

The product from Step B (0.71 g, 3.03 mmol) was saponified as described in Example 35, except that the mixture was heated at reflux for 4 hours, to produce 0.5 g (75%) of a mixture containing the desired compound along with an isomeric oxadiazole. $^1$H NMR was consistent with the proposed structure.

HRMS (M+) for C$_{10}$H$_{10}$N$_4$O$_3$ calculated: 220.0596; found: 220.0605.

Step D

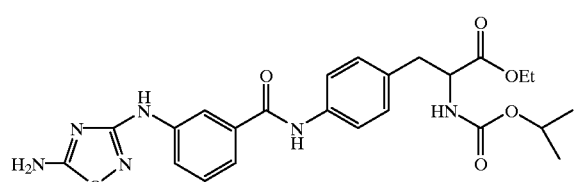

The product from Step C (0.1 g, 0.45 mmol) was coupled with the compound of Example AE as described in Example 103 Step C. The crude product was flash chromatographed (methanol/chloroform/aammonium hydroxide) to produced 0.04 g (17.8%) of the desired compound (slower retention) and 0.02 g (8.9%) of the isomeric oxadiazole (faster retention). $^1$H NMR was consistent with the proposed structures.

HRMS (M+) for C$_{10}$H$_{10}$N$_4$O$_3$ calculated: 496.2070; found: 496.2069.

Step E

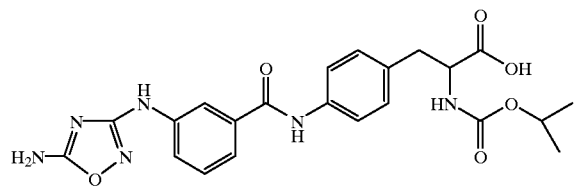

The product from Step D (0.04 g, 0.08 mmol) was saponified as described in Example 35 to provide, after reverse phase HPLC (CH$_3$CN/H$_2$O/TFA), 30 mg (75%) of the title compound. $^1$H NMR was consistent with the proposed structure.

APCI-MS (MH+) for C$_{22}$H$_{25}$N$_6$O$_6$ calculated: 469; found: 469.

EXAMPLE 105

4-[[[3-[[amino[(aminocarbonyl)imino]methyl]amino]phenyl]carbonyl]amino]-N-[(1-methylethoxy)carbonyl]phenylalanine, bis(trifluoroacetate) Salt

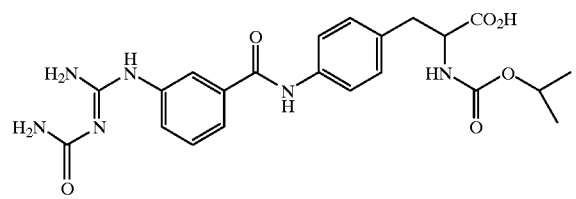

Step A
Preparation of methyl 3-[[(cyanoimino)(methylthio)methyl]amino]benzoate

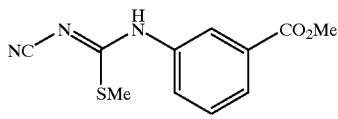

A stirred mixture of methyl 3-aminobenzoate (6.04 g, 40 mmol) and dimethyl N-cyanodithioiminocarbonate (11.96 g, 80 mmol) in pyridine (70 mL) was heated at reflux for 2.5 hours. The reaction mixture was cooled to room temperature and upon standing overnight at room temperature the above compound (6.2 g) crystallized from the reaction mixture. The compound was used without further purification. $^1$H NMR was consistent with the proposed structure.

Step B
Preparation of methyl 3-[[amino(cyanoimino)methyl]amino]benzoate

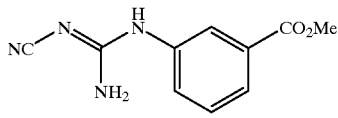

A mixture of the product from Step A (1.0 g) and ammonium hydroxide (2 mL) in ethanol (20 mL) was heated at 70° C. in a sealed tube for 3.5 hours. The reaction mixture was cooled to room temperature and reduced to half its volume. After standing overnight at room temperature a solid was obtained, which was filtered and washed with methanol to afford the above compound (389 mg) as a white solid. $^1$H NMR was consistent with the proposed structure.

Step C

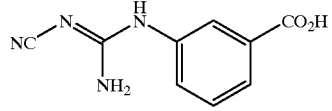

To a stirred solution of the product from Step B (2.9 g, 13.3 mmol) in THF (15 mL) and methanol (15 mL), was added 1N NaOH (14 mL). The reaction mixture was stirred at room temperature for 2 hours and concentrated in vacuo to afford a white solid. The residue was acidified by suspension in water followed by addition of 1N HCl. The resultant solid was filtered, washed with diethyl ether and dried to afford 2.4 g of the desired compound. $^1$H NMR was consistent with the proposed structure.

Step D

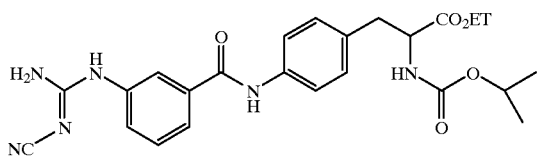

To a solution of the product from Step C (200 mg, 0.83 mmol) in DMF (1 mL) at −15° C. was added N-methylmorpholine (0.10 mL, 0.83 mmol) and i-butylchloroformate (0.11 mL, 0.83 mmol). The product of Example AE (245 mg, 0.83 mmol) in DMF (0.5 mL) was added and the reaction mixture stirred at −15° C. for 30 minutes and at room temperature for 18 hours. The reaction mixture was concentrated in vacuc and the residue purified by flash chromatography (90:9:1 CH$_2$Cl$_2$/MeOH/NH$_4$OH) to give 398 mg of the desired compound. $^1$H NMR was consistent with the proposed structure.

Step E

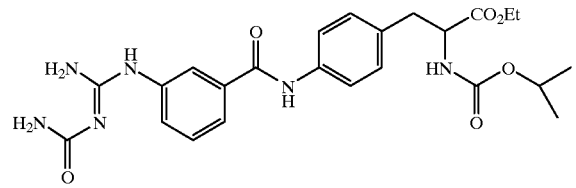

A solution of the product from Step D (95 mg, 0.20 mmol) in 1:1 CH$_2$Cl$_2$/TFA (1 mL) was stirred at room temperature for 2 hours. The solution was concentrated in vacuo and the residue purified by flash chromatography (90:9:1 CH$_2$Cl$_2$/MeOH/NH$_4$OH) to yield 65 mg of the desired compound. $^1$H NMR was consistent with the proposed structure.

Step F

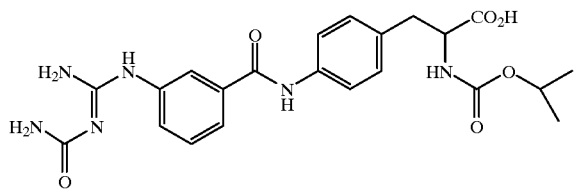

To a solution of the product from Step E (65 mg, 0.13 mmol) in 1:1 MeOH/THF (1 mL) was added 1N NaOH (0.5 mL). The mixture was stirred at room temperature for 2 hours and concentrated in vacuo. The residue was dissolved in water (1 mL) and the solution neutralized with 1N HCl. The white precipitate was collected and purified by reverse phase HPLC (water/acetonitrile) to afford 15 mg of the above compound. $^1$H NMR was consistent with the proposed structure.

EXAMPLE 106

4-[[[3-[(aminoiminomethyl)amino]phenyl]-carbonyl]amino]-N-[(3-methyl-1-oxobutyl)phenylalanine, bis (trifluoroacetate) Salt Step A

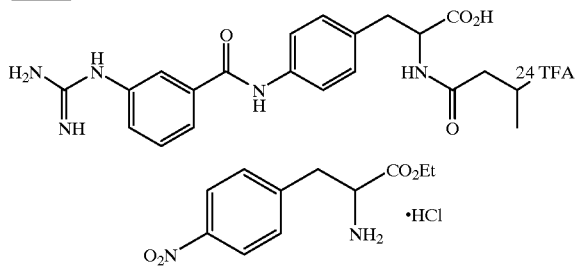

HCl gas was bubbled through a solution of 4-nitro-DL-phenylalanine hydrate (5.00 g, 23.8 mmol) in absolute ethanol (80 ml) at 0° C. for 5 minutes and the mixture refluxed overnight. The mixture was concentrated under reduced pressure and dried in vacuo to give a pale yellow solid (6.48 g, 98%). $^1$H NMR was consistent with the proposed structure.

Step B

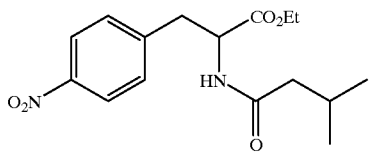

The product from Step A (2.00 g, 7.28 mmol) was dissolved in dichloromethane (50 ml) and cooled to 0° C. Isovaleryl chloride (1.23 g, 10.2 mmol) was added dropwise, followed by triethylamine (2.21 g, 21.8 mmol) and the mixture stirred overnight at room temperature. The mixture was concentrated and the residue dissolved in ethyl acetate, washed with water and brine and dried over MgSO$_4$. The solution was concentrated and dried in vacuo to give a pale yellow solid (2.30 g, 98%). $^1$H NMR was consistent with the proposed structure.

Step C

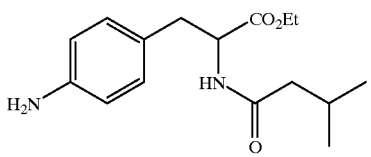

The product from Step B (2.30 g, 7.13 mmol) was dissolved in ethanol (30 mL) in a Parr vessel. 4% Pd/C (500 mg) was added and the mixture was hydrogenated at 5 psi for 4.5 hours. The solution was filtered through a plug of celite and the solution concentrated under reduced pressure. The residue was purified by flash chromatography on silica gel (60/40 ethyl acetate/heptane) to give a yellow solid (1.47 g, 70%). $^1$H NMR was consistent with the proposed structure.

Step D

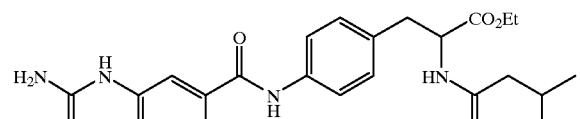

The product from Step C (439 mg, 1.5 mmol) and 3-guanidinobenzoic acid hydrochloride (323 mg, 1.5 mmol) were coupled under the conditions described in Example 76 Step D to provide, after purification by reverse-phase HPLC (water/acetonitrile), a white solid (190 mg, 28%). $^1$H NMR was consistent with the proposed structure.

Step E

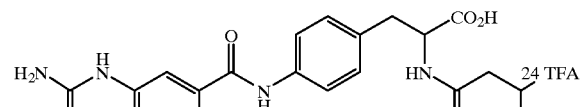

The product from Step D (190 mg, 0.42 mmol) was saponified as described in Example 35 to provide, after purification by reverse-phase HPLC (water/acetonitrile), the above compound as a white solid (140 mg, 79%). $^1$H NMR and MS were consistent with the proposed structure.

Analysis calculated for $C_{22}H_{27}N_5O_4 \cdot 2.4$ TFA: C, 46.04; H, 4.24; N, 10.02. Found: C, 46.03; H, 4.31; N, 9.85.

EXAMPLE 107

N-(3-methyl-1-oxobutyl)-4-[[[3-[(1,4,5,6-tetrahydro-pyrimidin-2-yl)amino]-5-(trifluoromethyl)phenyl]carbonyl]amino]phenylalanine, trifluoroacetate Salt

Step A

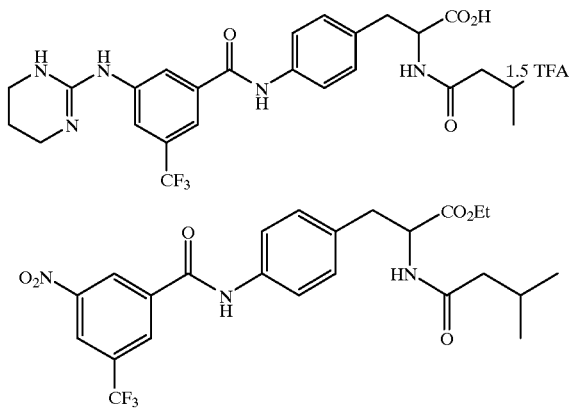

3-Nitro-5-trifluoromethylbenzoic acid (2.00 g, 8.51 mmol) was dissolved in toluene (20 ml) and cooled to 0° C. Oxalyl chloride (1.35 g, 10.63 mmol) was added to the solution, followed by 1 drop of DMF. The mixture was warmed to room temperature and stirred for 2 hours. The mixture was concentrated under reduced pressure to give the crude acid chloride as a clear yellow oil. A solution of the crude acid chloride (2.19 g, 8.64 mmol) in dichloromethane (20 ml) was added to a suspension of the product of Example 106 Step C (2.53 g, 8.64 mmol) in dichloromethane (20 ml). DMF (8 mL) was added to the suspension until homogeneous, followed by triethylamine (2.01 g, 19.9 mmol) and the mixture stirred at room temperature overnight. The mixture was concentrated and purified by flash chromatography on silica gel (70/30 ethyl acetate/hexane) to give a yellow solid (3.79 g, 89%). $^1$H NMR was consistent with the proposed structure.

Step B

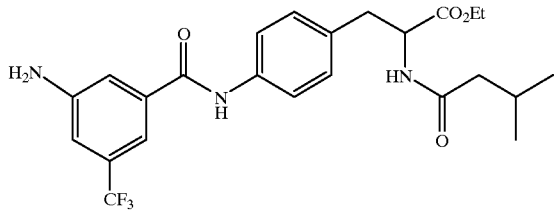

The product of Step A was reduced as described in Example 106 Step C to provide the desired aniline. $^1$H NMR was consistent with the proposed structure.

Step C

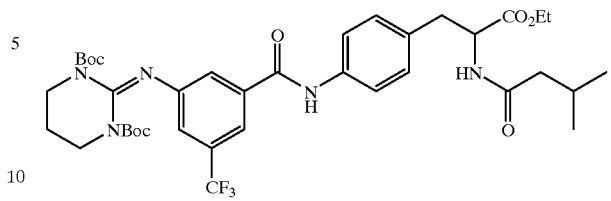

The above compound was synthesized from the product of Step B (1.00 g, 2.09 mmol) and the product of Example 131 (661 mg, 2.09 mmol) using the conditions described in Example AS. Purification by flash chromatography on silica gel (40/60 ethyl acetate/hexane) gave a yellow solid (320 mg, 20%). $^1$H NMR was consistent with the proposed structure.

Step D

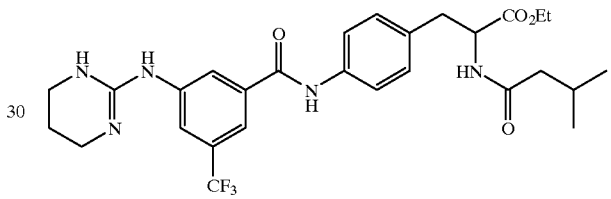

The product of Step C (320 mg, 0.42 mmol) was treated with TFA as described in Example 60 to provide, after purification by reverse-phase HPLC (water/acetonitrile) a white solid (140 mg, 59%). $^1$H NMR was consistent with the proposed structure.

Step E

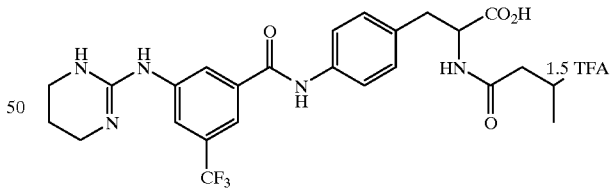

The product of Step D (140 mg, 0.25 mmol) was saponified as described in Example 35 to provide, after purification by reverse-phase HPLC (water/acetonitrile) the above compound as a white solid (128 mg, 96%). $^1$H NMR and MS were consistent with the proposed structure.

Analysis calculated for $C_{26}H_{30}N_5O_4F_3 \cdot 1.5$ TFA: C, 49.44; H, 4.51; N, 9.94. Found: C, 49.64; H, 4.21; N, 9.87.

EXAMPLE 108

4-[[[3-[(aminoiminomethyl)amino]-5-(trifluoromethyl)phenyl]carbonyl]amino]-N-(3-methyl-1-oxobutyl) phenylalanine, trifluoroacetate Salt Step A

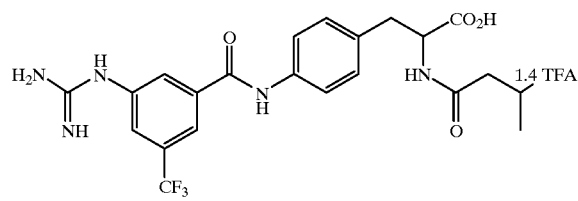

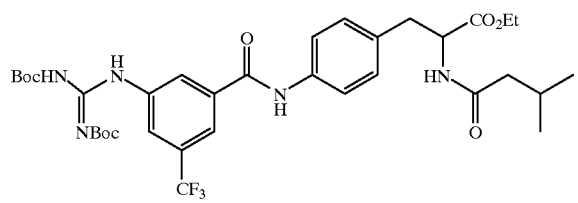

The compound from Example 107 Step B (2.016 g, 4.20 mmol) was treated with the product of Example AZ as described in Example AS to furnish, after purification by flash chromatography (30/70 ethyl acetate/hexane) an off-white solid (960 mg, 32%). $^1$H NMR was consistent with the proposed structure.

Steps B/C

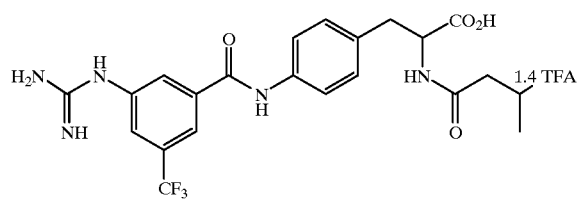

The above compound was prepared from the product of Step A using the conditions described in Example 60 and Example 35. $^1$H NMR and MS were consistent with the proposed structure.

Analysis calculated for $C_{23}H_{26}N_5O_4F_3 \cdot 1.4$ TFA: C, 47.45; H, 4.23; N, 10.72. Found: C, 47.43; H, 3.96; N, 10.76.

EXAMPLE 109

4-[[[3-[(aminoiminomethyl)amino]phenyl]carbonyl]amino]-N-(3,3-dimethyl-1-oxobutyl)phenylalanine, trifluoroacetate Salt

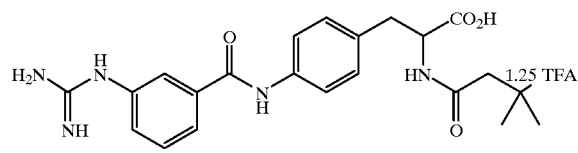

The above compound was prepared in the same manner as described for the preparation of the compound of Example 106, substituting t-butylacetyl chloride for isovaleryl chloride. $^1$H NMR and MS were consistent with the proposed structure.

Analysis calculated for $C_{23}H_{29}N_5O_4 \cdot 1.25$ TFA: C, 52.62; H, 5.24; N, 12.03. Found: C, 52.48, H, 5.49; N, 12.03.

EXAMPLE 110

4-[[[3-[(aminoiminomethyl)amino]-5-(trifluoromethyl)phenyl]carbonyl]amino]-N-(3,3-dimethyl-1-oxobutyl)phenylalanine, trifluoroacetate Salt

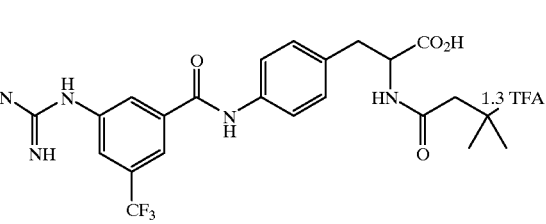

The above compound was prepared in the same manner as described for the preparation of the compound of Example 108, substituting t-butylacetyl chloride for isovaleryl chloride. $^1$H NMR and MS were consistent with the proposed structure.

Analysis calculated for $C_{24}H_{28}N_5O_4F_3 \cdot 1.3$ TFA: C, 48.72; H, 4.50; N, 10.68. Found: C, 48.54; H, 4.35; N, 10.72.

EXAMPLE 111

N-(phenylsulfonyl)-4-[[[3-[(1,4,5,6-tetrahydropyrimidin-2-yl)amino]phenyl]carbonyl]amino] phenylalanine, trifluoroacetate Salt Steps A/B

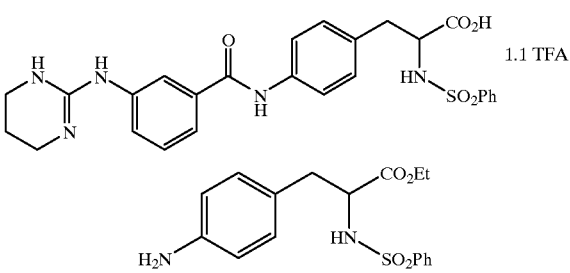

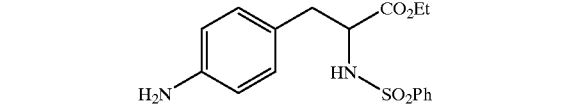

The above compound was prepared from the product of Example 106 Step A using the procedures described in Example 106 Steps B and C, substituting benzenesulfonyl chloride for isovaleryl chloride. $^1$H NMR was consistent with the proposed structure.

Step C

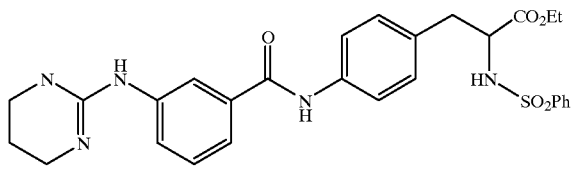

The desired compound was prepared from the product of Step A/B and the product of Example 130, using the procedure described in Example 106 Step D. ¹H NMR was consistent with the proposed structure.

Step D

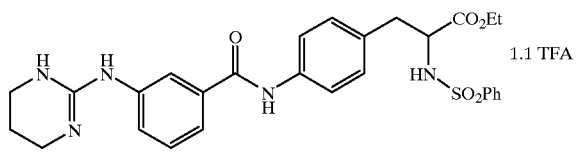

The product of Step C was saponified using the procedure described in Example 35 to provide the above compound. ¹H NMR and MS were consistent with the proposed structure.

Analysis calculated for $C_{26}H_{27}N_5O_5S \cdot 1.1$ TFA: C, 52.35; H, 4.38; N, 10.82. Found: C, 52.42; H, 4.08; N, 10.91.

EXAMPLE 112

4-[[[3-[(4,5-dihydro-1H-imidazol-2-yl)amino]phenyl]carbonyl]amino-N-(phenylsulfonyl)phenylalanine, trifluoroacetate Salt Steps A/B

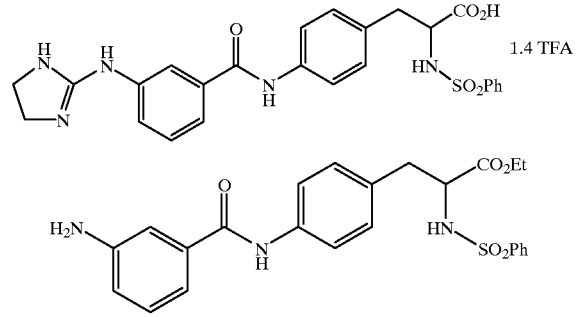

The desired compound was prepared from the product of Example 111 Step A/B and 3-nitrobenzoyl chloride using the procedure described in Example 107 Steps A and B. ¹H NMR was consistent with the proposed structure.

Steps C/D/E

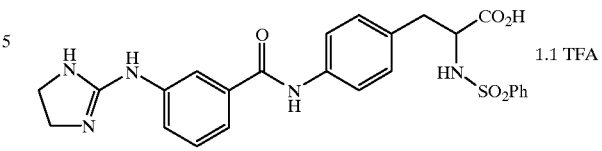

The above compound was prepared from the product of Step A/B and the product of Example 132 using the procedures described in Example 107 Steps C, D and E. ¹H NMR and MS were consistent with the proposed structure.

Analysis calculated for $C_{25}H_{25}N_5O_5S \cdot 1.4$ TFA: C, 50.05; H, 3.99; N, 10.50. Found: C, 49.88; H, 3.89; N, 10.62.

EXAMLE 113

4-[[[3-[(aminoiminomethyl)amino]phenyl]carbonyl]amino]-2-methoxy-N-[(1-methylethoxy)carbonyl]phenylalanine, trifluoroacetate salt, monohydrate Steps A/B/C

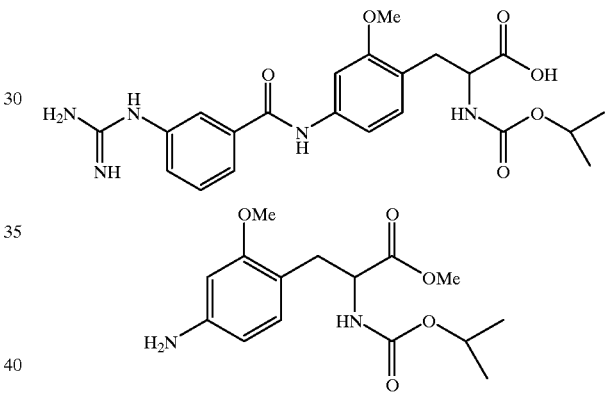

The above compound was prepared from methyl pyruvate, isopropylcarbamate and 2-bromo-5-nitro anisole using the procedures described in Example 76 Steps A, B and C.

Step D

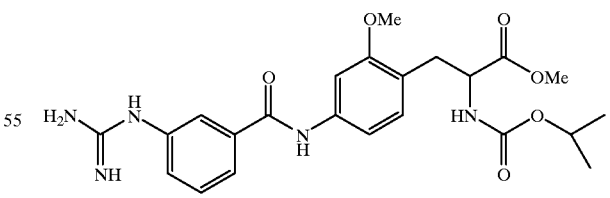

The compound of Step A/B/C (370 mg, 1.19 mmol), was coupled with 3-guanidinobenzoic acid hydrochloride under the conditions described in Example 76 Step D to give 450 mg of desired product. ¹H NMR was consistent with the proposed structure.

Analysis calculated for $C_{23}H_{29}N_5O_6 \cdot 1.0$ TFA $\cdot 0.8$ H$_2$O: C, 50.05; H, 5.31; N, 11.67. Found: C, 50.00; H, 4.91; N, 11.49.

Step E

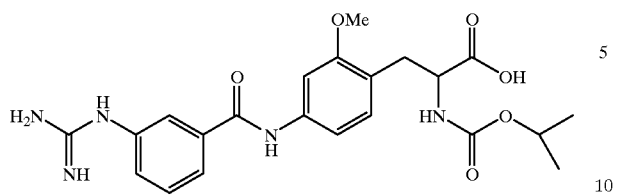

The product of Step D (350 mg, 0.6 mmol) was saponified as described in Example 35 to give 230 mg of the above compound. $^1$H NMR was consistent with the proposed structure.

Analysis calculated for $C_{22}H_{27}N_5O_6 \cdot 1.0$ TFA$\cdot 1.0$ H$_2$O: C, 48.90; H, 5.13; N, 11.88. Found: C, 48.67; H, 4.73; N, 11.76.

EXAMPLE 114

2-methoxy-N-[(1-methylethoxy)carbonyl]-4-[[[3-[(1,4,5,6-tetrahydropyrimidin-2-yl)amino]phenyl]-carbonyl]amino]phenylalanine, trifluoroacetate Salt

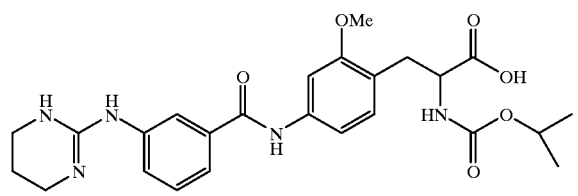

Step A

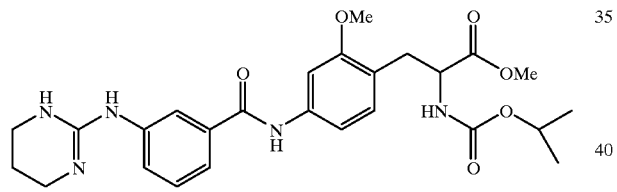

The above compound was prepared from the compound of Example 113 Step A/B/C (485 mg, 1.56 mmol) and the product of Example 130 (400 mg, 1.56 mmol) using the conditions described in Example 76 Step D to give 710 mg of desired product. $^1$H NMR was consistent with the proposed structure.

Analysis calculated for $C_{26}H_{33}N_5O_6 \cdot 1.0$ TFA: C, 53.76; H, 5.48; N, 11.19. Found: C, 53.54; H, 5.65; N, 11.11.

Step B

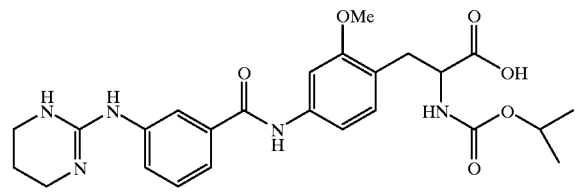

The product of Step A was saponified as described in Example 35 to give the above compound. $^1$H NMR was consistent with the proposed structure.

Analysis calculated for $C_{25}H_{31}N_5O_6 \cdot 1.0$ TFA$\cdot 0.5$ H$_2$O: C, 52.26; H, 5.36; N, 11.29. Found: C, 51.97; H, 5.08; N, 11.16.

EXAMPLE 115

4-[[[3-(aminoiminomethyl)amino]phenyl]carbonyl]amino]-2-methoxybenzenepropanoic Acid, trifluoroacetate Salt

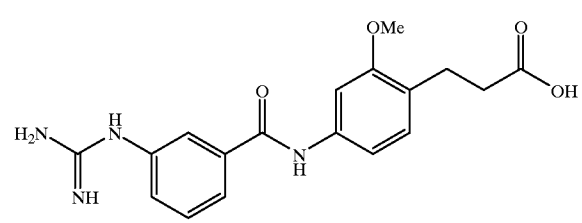

Step A

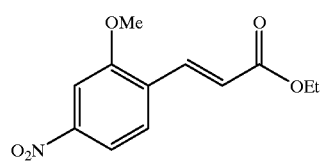

2-bromo-5-nitroanisole (1 g, 4.3 mmol) and ethyl acrylate were coupled using the procedure described in Example 100 Step B to give 1.10 g of the desired compound. $^1$H NMR was consistent with the proposed structure.

Step B

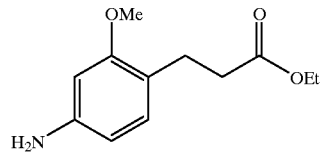

The compound of Step A (2 g, 0.85 mmol) was reduced under the conditions described in Example 106 Step C to give, after flash chromatography (30/70 ethyl acetate/hexane), 1.6 g of desired product. $^1$H NMR was consistent with the proposed structure.

Steps C/D

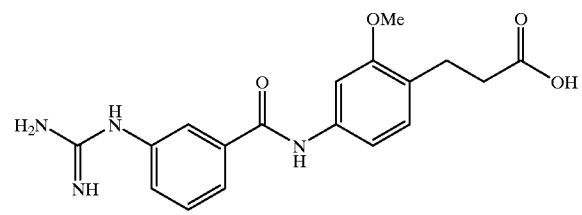

The compound from Step B was coupled with 3-guanidinobenzoic acid hydrochloride under the conditions described in Example 76 Step D and saponified as described in Example 35 to give the above compound. $^1$H NMR was consistent with the proposed structure.

Analysis calculated for $C_{18}H_{20}N_4O_4 \cdot 1.4$ TFA$\cdot 1.4$ H$_2$O: C, 46.16; H, 4.51; N, 10.35. Found: C, 46.38; H, 4.36; N, 10.20.

EXAMPLE 116

2-methoxy-4-[[[3-[(1,4,5,6-tetrahydropyrimidin-2-yl)amino]phenyl]carbonyl]amino]benzenepropanoic Acid, trifluoroacetate Salt Step A

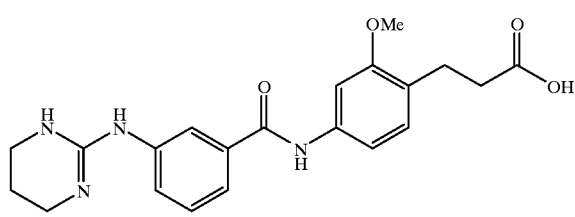

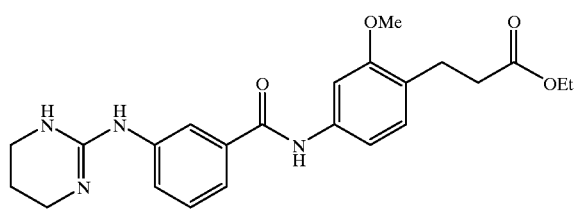

The product from Example 115 Step B (350 mg, 1.56 mmol) and the product of Example 130 (400 mg, 1.56 mmol) were coupled using the procedure of Example 76 Step D to give the desired compound. ¹H NMR was consistent with the proposed structure.

Analysis calculated for $C_{23}H_{28}N_4O_4 \cdot 1.0$ TFA $\cdot 1.5$ $H_2O$: C, 53.09; H, 5.70; N, 9.91. Found: C, 52.94; H, 5.52; N, 9.63.

Step B

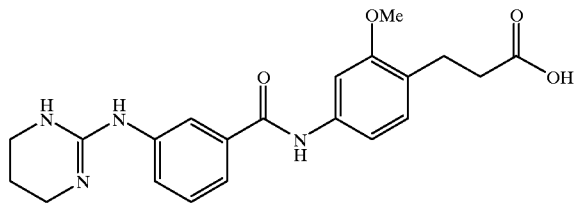

The product of Step A was saponified using the conditions of Example 35 to give the above compound. ¹H NMR was consistent with the proposed structure.

Analysis calculated for $C_{23}H_{28}N_4O_4 \cdot 1.0$ TFA $\cdot 1.5$ $H_2O$: C, 53.18; H, 5.04; N, 10.79. Found: C, 53.46; H, 5.04; N, 10.74.

EXAMPLE 117

4-[[[3-[(aminoiminomethyl)amino]phenyl]carbonyl]amino]-2-(dimethylamino)benzenepropanoic Acid, bis(trifluoroacetate) Salt Step A

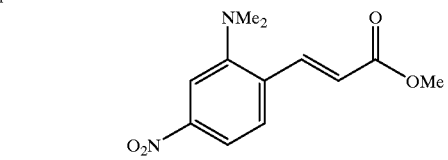

2-bromo-5-nitroaniline (2 g, 9.22 mmol) and methyl acrylate were coupled using the procedure described in Example 100 Step B to give, after purification by flash chromatography (20/80 ethyl acetate/hexane), 1.05 g of product. ¹H NMR was consistent with the proposed structure.

Step B

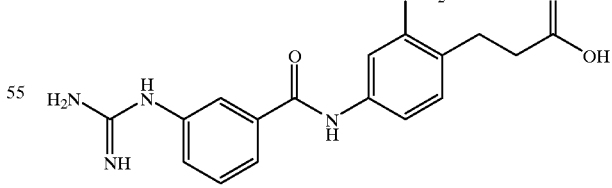

The compound of Step A (500 mg, 2.25 mmol) and potassium carbonate (622 mg, 4.50 mmol) were stirred in of DMF (5 ml) for 1 hour and methyl iodide (5 mL) was added. The mixture was stirred at 50° C. overnight, cooled, diluted with water and extracted with ethyl acetate. The solution was dried over $MgSO_4$ and concentrated to give, after flash chromatography (20/80 ethyl acetate/hexane), 380 mg of product. ¹H NMR was consistent with the proposed structure.

Steps C/D/E

The compound from Step B was reduced, coupled and saponified using the conditions described in Example 115 Steps B and C/D to provide the above compound. ¹H NMR was consistent with the proposed structure.

Analysis calculated for $C_{19}H_{23}N_5O_3 \cdot 2.8$ TFA: C, 42.90; H, 3.78; N, 10.17. Found: C, 42.78; H, 3.65; N, 10.03.

EXAMPLE 118

[4-[[[3-[(aminoiminomethyl)amino]phenyl]carbonyl]amino]-2-methoxyphenoxy]acetic Acid, trifluoroacetate Salt

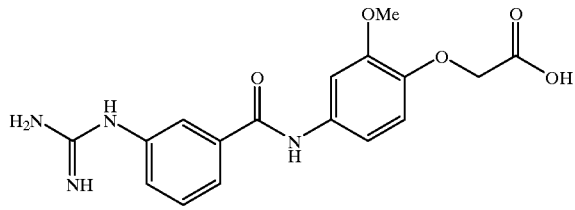

Step A

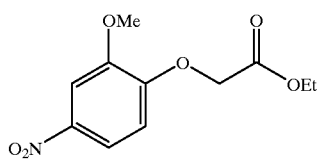

A solution of 4-nitroguaiacol (2 g, 11.83 mmol) and potassium carbonate (1.96 g, 14.19 mmol) in DMF (20 ml) was stirred at room temperature for 1 hour and ethyl bromoacetate (1.98 g, 11.83 mmol) was added. After stirring at room temperature overnight the reaction mixture was diluted with water and the solid filtered, washed with water and dried to give the product. $^1$H NMR was consistent with the proposed structure.

Step B

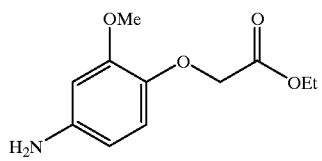

To the compound of Step A (2.9 g, 11.36 mmol) in ethanol (80 ml) was added tin(II) chloride dihydrate (7.69 g, 34.09 mmol) and the reaction mixture stirred at 80° C. for 4 hours. The mixture was cooled, neutralized with 10% NaOH and extracted with ethyl acetate. The extract was dried over MgSO$_4$ and concentrated to give, after flash chromatography (10/90 ethyl acetate/hexane), 660 mg of product. $^1$H NMR was consistent with the proposed structure.

Steps C/D

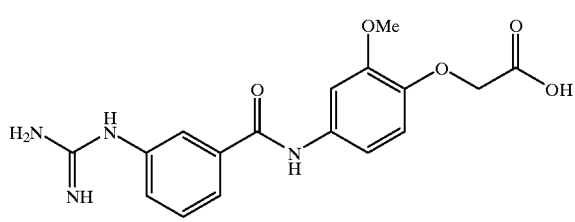

The product of Step B was coupled with 3-guanidinobenzoic acid hydrochloride as described in Example 76 Step D and saponified as described in Example 35 to furnish the above compound. $^1$H NMR was consistent with the proposed structure.

Analysis calculated for $C_{17}H_{18}N_4O_5 \cdot 1.0$ TFA: C, 48.31; H, 4.05; N, 11.86. Found: C, 48.08; H, 3.94; N, 11.69.

EXAMPLE 119

[2-methoxy-4-[[[3-[(1,4,5,6-tetrahydropyrimidin-2-yl]amino]phenyl]carbonyl]amino]phenoxy]acetic Acid, trifluoroacetate Salt

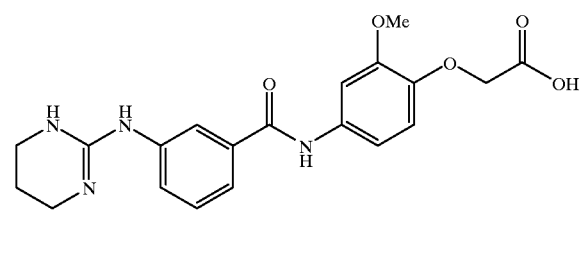

The above compound was prepared as described for Example 118, using the product of Example 130 in place of 3-guanidinobenzoic acid hydrochloride. $^1$H NMR was consistent with the proposed structure.

Analysis calculated for $C_{17}H_{18}N_4O_5 \cdot 1.2$ TFA$\cdot 1.0$ H$_2$O: C, 48.63; H, 4.59; N, 10.13. Found: C, 48.23; H, 4.31; N, 9.89.

EXAMPLE 120

[[4-[[[3-[(aminoiminomethyl)amino]phenyl]carbonyl]amino]phenyl]methyl]-1,3-propanoic Acid, trifluoroacetic Salt

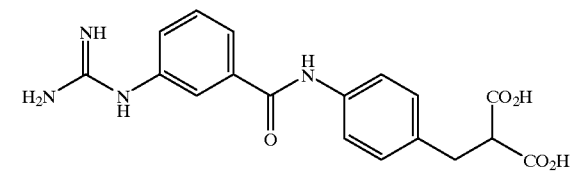

Step A

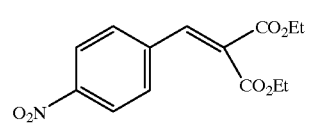

The above compound was prepared using the procedure described in Synthesis-Stuttgart 12, 1026–1027 (1986). $^1$H NMR was consistent with the proposed structure.

Step B

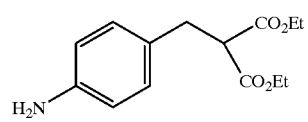

The compound of Step A was reduced using the procedure described in Example 106 Step C to provide the desired aniline. $^1$H NMR was consistent with the proposed structure.

Step C

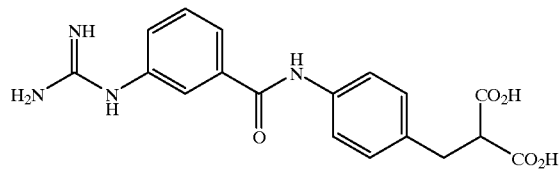

The above compound was prepared using the procedures described in Example 127 Step B to Step D/E/F. 1H NMR was consistent with the proposed structure.

Analysis calculated for $C_{18}H_{16}N_4O_5 \cdot 1.8$ TFA $\cdot 0.7$ H$_2$O: C, 44.26; H, 3.30; N, 9.56. Found: C, 44.17; H, 2.99; N, 9.75.

EXAMPLE 121

4-[[[3-[(aminoiminomethyl)amino]phenyl]carbonyl]amino]-N-[(2,4,6-trimethylphenyl)sulfonyl]phenylalanine, trifluoroacetate Salt

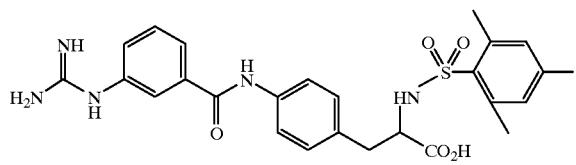

The above compound was prepared in the same manner as described in Example 106, replacing isovaleryl chloride with 2,4,6-trimethylbenzenesulfonyl chloride. $^1$H NMR was consistent with the proposed structure.

Analysis calculated for $C_{26}H_{29}N_5O_5 \cdot 1.5$ TFA $\cdot 0.2$ H$_2$O: C, 49.88; H, 4.46; N, 10.03. Found: C, 49.71; H, 4.51; N, 10.05.

EXAMPLE 122

[4-[[[3-[(aminoiminomethyl)amino]phenyl]carbonyl]amino]-N-[(3,5-dichlorophenyl)sulfonyl]phenylalanine, trifluoroacetate Salt

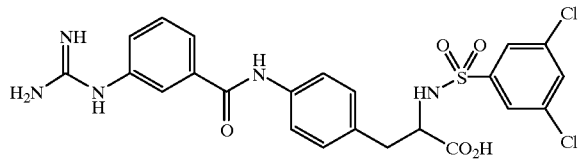

The above compound was prepared in the same manner as described in Example 106, replacing isovaleryl chloride with 3,5-dichlobenzenesulfonyl chloride. $^1$H NMR was consistent with the proposed structure.

Analysis calculated for $C_{23}H_{21}N_5O_5SCl_2 \cdot 1.4$ TFA: C, 51.86; H, 4.85; N, 10.61. Found: C, 51.57; H, 4.99; N, 11.01.

EXAMPLE 123

4-[[[3-[(aminoiminomethyl)amino]phenyl]carbonyl]amino]-N-[(2-phenylethenyl)sulfonyl]phenylalanine, trifluoroacetate Salt

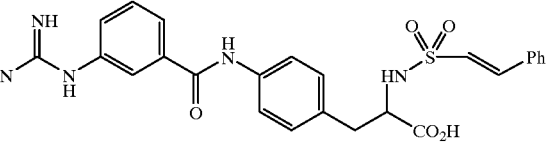

The above compound was prepared in the same manner as described in Example 106, replacing isovaleryl chloride with trans-p-styrenesulfonyl chloride. $^1$H NMR was consistent with the proposed structure.

EXAMPLE 124

4-[[[3-[(aminoiminomethyl)amino]phenyl]carbonyl)amino]-N-[[(1,1-dimethylethyl)amino]carbonyl]phenylalanine, trifluoroacetate Salt

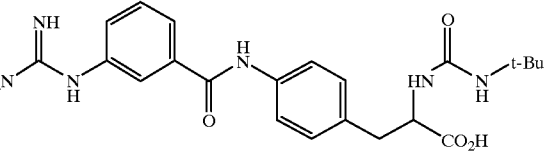

Step A

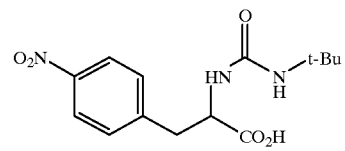

The product of Example 106 Step A was dissolved in CH$_2$Cl$_2$ (8 mL) and cooled to 0° C. t-Butyl isocyanate (139 mg, 1.4 mmol) was added followed by triethylamine (151 mg, 1.5 mmol) and the mixture stirred overnight. The mixture was concentrated in vacuo, the residue dissolved in EtOAc and the solution washed with water and brine, dried over Na$_2$SO$_4$ and concentrated to give 0.5 g of a yellow solid. $^1$H NMR was consistent with the proposed structure.

Steps B/C/D

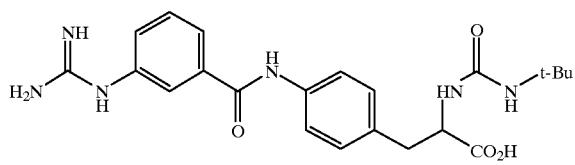

The title compound was prepared from the product of Step A using the procedures described in Example 106 Steps C, D and E. $^1$H NMR was consistent with the proposed structure.

Analysis calculated for $C_{22}H_{28}N_6O_4 \cdot 1.5$ TFA: C, 49.14; H, 4.78; N, 13.75. Found: C, 48.99; H, 4.77; N, 14.11.

EXAMPLE 125

4-[[[3-[(aminoiminomethyl)amino]phenyl]carbonyl]amino]-N-[(4-morpholinyl)carbonyl]phenylalanine, bis(trifluoroacetate) Salt, monohydrate

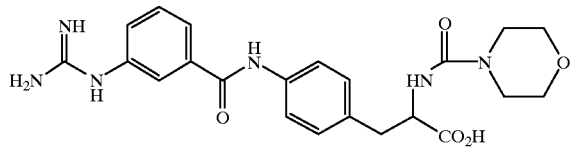

Step A

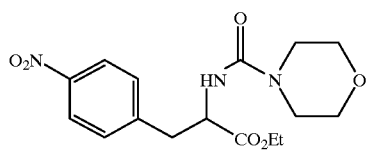

The compound of Example 106 Step A was dissolved in benzene (15 mL) and cooled to 0° C. Triphosgene (216 mg, 0.73 mmol) was added followed by triethylamine (441 mg, 4.36 mmol) and the mixture refluxed for 2 hours. The mixture was cooled and concentrated in vacuo and the residue dissolved in $CH_2Cl_2$. Morpholine (190 mg, 2.18 mmol) was added and the mixture stirred at room temperature overnight. The mixture was concentrated in vacuo and the residue dissolved in EtOAc, washed with water and brine and dried over $Na_2SO_4$. Concentration and purification by flash chromatography (40/60 acetonitrile/toluene) furnished 590 mg of a white solid. $^1$H NMR was consistent with the proposed structure.

Step B/C/D

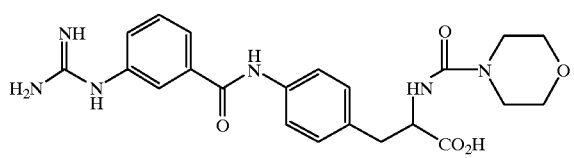

The title compound was prepared from the product of Step A using the procedures described in Example 106 Steps C, D and E. $^1$H NMR was consistent with the proposed structure.

Analysis calculated for $C_{22}H_{26}N_6O_5 \cdot 2.0$ TFA$\cdot 0.1$ $H_2O$: C, 45.63; H, 4.15; N, 12.28. Found: C, 45.79; H, 4.52; N, 12.12.

EXAMPLE 126

4-[[[3-[(aminoiminomethyl)amino]phenyl]carbonyl]amino]-N-[(1-pipridinyl)carbonyl]phenylalanine, trifluoroacetate Salt

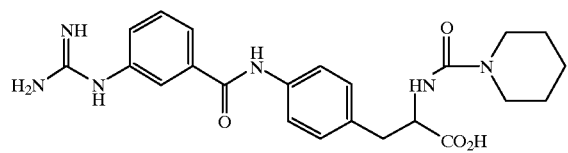

The title compound was prepared in the same manner as described in Example 125, replacing morpholine with piperidine. $^1$H NMR was consistent with the proposed structure.

Analysis calculated for $C_{23}H_{28}N_6O_4 \cdot 1.4$ TFA$\cdot 0.1$ $H_2O$: C, 50.47; H, 4.86; N, 13.69. Found: C, 50.26; H, 4.67; N, 13.85.

EXAMPLE 127

4-[[[3-[(aminoiminomethyl)amino]phenyl]carbonyl]amino]-3-chloro-N-[(1-methylethoxy)carbonyl]phenylalanine, trifluoroacetate Salt

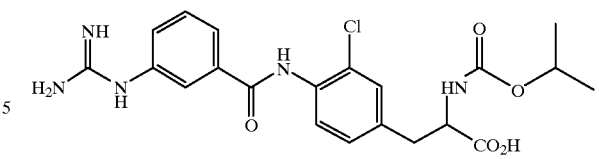

Step A

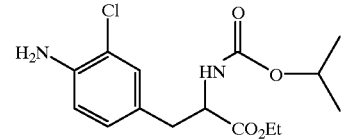

The compound of Example AE (588 mg, 2.0 mmol) and N-chlorosuccinimide (268 mg, 2.0 mmol) were stirred in acetonitrile (8 mL) at room temperature overnight. The mixture was concentrated in vacuo and the residue suspended in 10% $NaHSO_3$ and stirred for 2 hours. The mixture was extracted with ethyl acetate (3×) and the organic layers collected, washed with brine, dried over $Na_2SO_4$ and concentrated. The residue was purified by flash chromatography (99:1 $MeOH/CH_2Cl_2$) to give 360 mg of the desired compound. $^1$H NMR was consistent with the proposed structure.

Step B

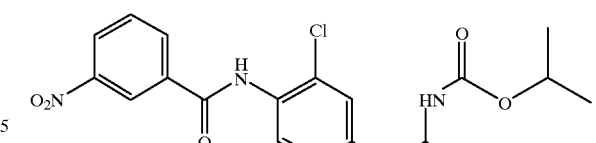

The desired compound was prepared from the product of Step A using the procedure described in Example AQ. $^1$H NMR was consistent with the proposed structure.

Step C

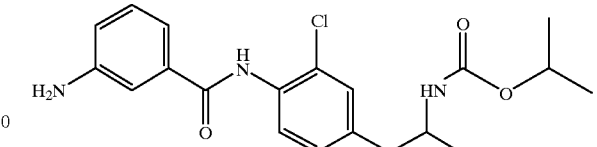

The desired compound was prepared from the product of Step B using the procedure described in Example 106 Step C. $^1$H NMR was consistent with the proposed structure.

Steps D/E/F

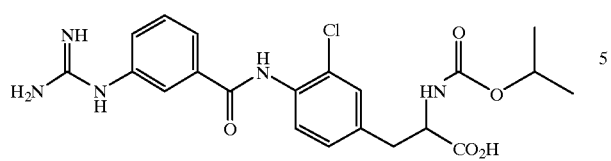

The title compound was prepared from the product of Step C using the procedures described in Example 108 Steps A and B/C. $^1$H NMR was consistent with the proposed structure.

Analysis calculated for $C_{21}H_{24}N_5O_5 \cdot 1.5$ TFA: C, 45.54; H, 4.06; N, 11.06. Found: C, 45.46; H, 4.11; N, 10.79.

EXAMPLE 128

4-[[[3-[[(aminoiminomethyl)amino]carbonyl]phenyl]carbonyl]amino]-N-[(1-methylethoxy)carbonyl]phenylalanine, trifluoroacetate Salt

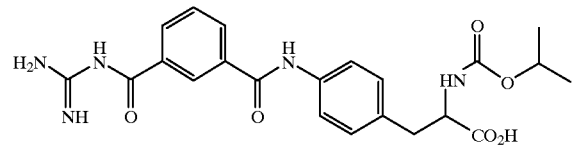

Step A

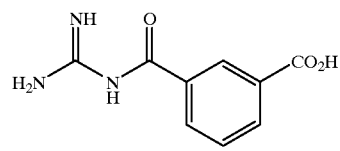

Flask A: A suspension of 60% NaH in mineral oil (1.2 g, 24 mmol washed with hexane before use) in DMF (20 mL) was cooled to 0° C. and guanidine hydrochloride (2.4 g, 25 mmol) was added very slowly. The reaction was allowed to stir at room temperature for 2 hours.

Flask B: To a solution of isophthalic acid (0.83 g, 5 mmol) in DMF (5 mL) at 0° C. was added 1-methylpiperidine (496 mg, 5 mmol), followed by isobutyl chloroformate (205 mg, 1.5 mmol). The mixture was stirred for 5 minutes and the solution of Flask A was added. The mixture was stirred overnight and concentrated. The residue was purified by reverse-phase HPLC (water/acetonitrile) to afford 300 mg of a white solid. $^1$H NMR was consistent with the proposed structure.

Steps B/C

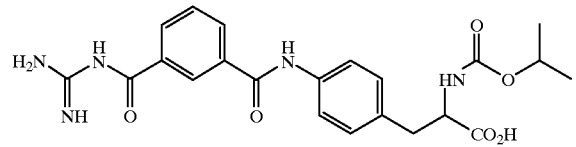

The title compound was prepared from the product of Step A and the compound of Example AE using the procedures described in Example 106 Steps D and E. $^1$H NMR was consistent with the proposed structure.

Analysis calculated for $C_{22}H_{25}N_5O_6 \cdot 1.3$ TFA: C, 48.93; H, 4.39; N, 11.60. Found: C, 48.74; H, 4.63; N, 11.44.

EXAMPLE 129

4-[[[3-[(aminoiminomethyl)amino]phenyl]carbonyl]amino]-α-ethylbenzenepropanoic Acid, trifluoroacetate Salt

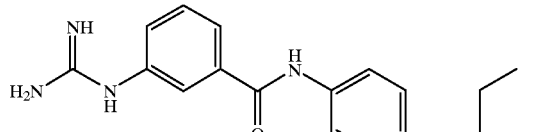

Step A

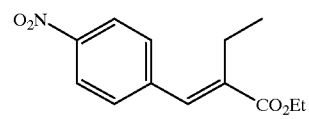

A suspension of 60% NaH in mineral oil (2 g, 51 mmol, washed with hexane before use) in THF (75 mL) was cooled to 0° C. and triethyl 2-phosphonobutyrate (7.75 mL, 33 mmol) was added slowly. The white slurry was stirred at 0° C. for 1.5 hours and a solution of 4-nitrobenzaldehyde (4.5 g, 30 mmol) in THF (10 mL) was added. The mixture was stirred at room temperature for 4 hours and quenched with water and extracted with EtOAc (3×). The organic layers were collected, washed with brine, dried over $Na_2SO_4$ and concentrated. The residue was purified by flash chromatography on (4:1 hexane/ethyl acetate) to give 4 g of a yellow solid. $^1$H NMR was consistent with the proposed structure.

Steps B/C/D

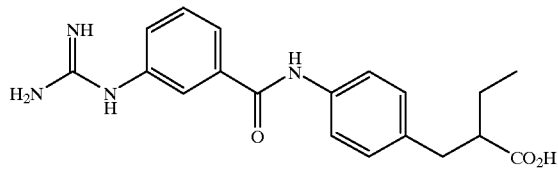

The title compound was prepared from the product of Step A using the procedures described in Example 106 Steps C, D and E. $^1$H NMR was consistent with the proposed structure.

Analysis calculated for $C_{19}H_{22}N_4O_3 \cdot 1.2$ TFA. $0.5$ $H_2O$: C, 51.38; H, 4.88; N, 11.20. Found: C, 51.35; H, 4.72; N, 11.36.

EXAMPLE 130

3-[(1,4,5,6-tetrahydropyrimidin-2-yl)amino]benzoic Acid

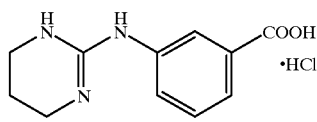

Step A

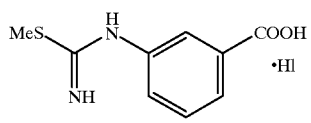

1-(3-Carboxyphenyl)-2-thiourea (5 g, 0.025 mol) ) and iodomethane (3.62 g, 0.025 mole) in THF (75 mL) were stirred at reflux for 2 hours. The solvent was removed and the residue washed with ether (3×) to yield, after drying under vacuum, the desired salt (7.8 g) as a yellow solid.

Step B

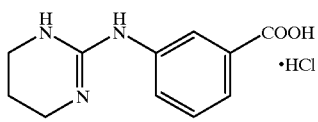

To the product of Step A (10.1 g, 0.03 mol) in DMF (15 mL) was added 1,3-diaminopropane (2.22 g, 0.03 mol), triethylamine (3.9 g, 0.03 mol), and DMAP (420 mg). The reaction mixture was heated at 140–150° C. for 4.5 hours and cooled to room temperature. $H_2O$ (30 mL) was added and, after stirring for 15 minutes, the precipitate filtered and washed with $H_2O$. The precipitate was slurried in $H_2O$ and made acidic with concentrated HCl. The solution was lyophilized and the residue washed 2× with isopropyl ether and dried, furnishing the above compound (4.0 g) as a white solid. $^1$H NMR and MS were consistent with the desired structure.

EXAMPLE 131

N,N'-bis-(Boc)-2-(1H)-tetrahydropyrimidinethione

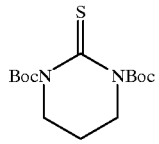

The above compound was prepared from 2-(1H)-tetrahydropyrimidinethione using the procedure described in Example AZ. $^1$H NMR was consistent with the desired structure.

EXAMPLE 132

N,N'-bis-(Boc)-2-imidazolidinethione

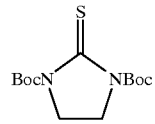

The above compound was prepared from 2-imidazolidinethione using the procedure described in Example AZ. $^1$H NMR was consistent with the desired structure.

The activity of the compounds of the present invention was tested in the following assays. The results of testing in the assays are tabulated in Table 1.

VITRONECTIN ADHESION ASSAY

Materials

Human vitronectin receptor($\alpha_v\beta_3$) was purified from human placenta as previously described [Pytela et al., *Methods in Enzymology*, 144:475–489 (1987)]. Human vitronectin was purified from fresh frozen plasma as previously described [Yatohgo et al., *Cell Structure and Function*, 13:281–292 (1988)]. Biotinylated human vitronectin was prepared by coupling NHS-biotin from Pierce Chemical Company (Rockford, Ill.) to purified vitronectin as previously described [Charo et al., *J. Biol. Chem.*, 266(3):1415–1421 (1991)]. Assay buffer, OPD substrate tablets, and RIA grade BSA were obtained from Sigma (St. Louis, Mo.). Anti-biotin antibody was obtained from Calbiochem (La Jolla, Calif.). Linbro microtiter plates were obtained from Flow Labs (McLean, Va.). ADP reagent was obtained from Sigma (St. Louis, Mo.).

Methods
Solid Phase Receptor Assays

This assay was essentially the same as previously reported [Niiya et al., *Blood*, 70:475–483 (1987)]. The purified human vitronectin receptor ($\alpha_v\beta_3$) was diluted from stock solutions to 1.0 μg/mL in Tris-buffered saline containing 1.0 mM $Ca^{++}$, $Mg^{++}$, and $Mn^{++}$, pH 7.4 ($TBS^{+++}$). The diluted receptor was immediately transferred to Linbro microtiter plates at 100 μL/well (100 ng receptor/well). The plates were sealed and incubated overnight at 4° C. to allow the receptor to bind to the wells. All remaining steps were at room temperature. The assay plates were emptied and 200 μL of 1% RIA grade BSA in $TBS^{+++}$ ($TBS^{+++}$/BSA) were added to block exposed plastic surfaces. Following a 2 hour incubation, the assay plates were washed with $TBS^{+++}$ using a 96 well plate washer. Logarithmic serial dilution of the test compound and controls were made starting at a stock concentration of 2 mM and using 2 nM biotinylated vitronectin in $TBS^{+++}$/BSA as the diluent. This premixing of labeled ligand with test (or control) ligand, and subsequent transfer of 50 μL aliquots to the assay plate was carried out with a CETUS Propette robot; the final concentration of the labeled ligand was 1 nM and the highest concentration of test compound was $1.0\times10^{-4}$ M. The competition occurred for two hours after which all wells were washed with a plate washer as before. Affinity purified horseradish peroxidase labeled goat anti-biotin antibody was diluted 1:3000 in $TBS^{+++}$/BSA and 125 μL were added to each well. After 30 minutes, the plates were washed and incubated with OPD/$H_2O_2$ substrate in 100 mM/L Citrate buffer, pH 5.0. The plate was read with a microtiter plate reader at a wavelength of 450 nm and when the maximum-binding control wells reached an absorbance of about 1.0, the final $A_{450}$ were recorded for analysis. The data were analyzed using a macro written for use with the EXCEL™ spreadsheet program. The mean, standard deviation, and % CV were determined for duplicate concentrations. The mean $A_{450}$ values were normalized to the mean of four maximum-binding controls (no competitor added)(B-MAX). The normalized values were subjected to a four parameter curve fit algorithm [Rodbard et al., *Int. Atomic Energy Agency, Vienna*, pp 469 (1977)], plotted on a semi-log scale, and the computed concentration corresponding to inhibition of 50% of the maximum binding of biotinylated vitronectin ($IC_{50}$) and corresponding $R^2$ was reported for those compounds exhibiting greater than 50% inhibition at the highest concentration tested; otherwise the $IC_{50}$ is reported as being greater than the highest concentration tested. β-[[2-[[5-[(aminoiminomethyl)amino]-1-oxopentyl]amino]-1-oxoethyl]amino]-3-pyridinepropanoic acid [U.S. Ser. No. 08/375,338, Example 1] which is a potent $\alpha_v\beta_3$ antagonist ($IC_{50}$ in the range 3–10 nM) was included on each plate as a positive control.

PURIFIED IIb/IIIa RECEPTOR ASSAY

Materials

Human fibrinogen receptor ($\alpha_{IIb}\beta_3$) was purified from outdated platelets. (Pytela, R., Pierschbacher, M. D., Argraves, S., Suzuki, S., and Rouslahti, E. "Arginine-Glycine-Aspartic acid adhesion receptors", *Methods in Enzymology* 144(1987):475–489.) Human vitronectin was purified from fresh frozen plasma as described in Yatohgo, T., Izumi, M., Kashiwagi, H., and Hayashi, M., "Novel purification of vitronectin from human plasma by heparin affinity chromatography," *Cell Structure and Function* 13(1988):281–292. Biotinylated human vitronectin was prepared by coupling NHS-biotin from Pierce Chemical Company (Rockford, Ill.) to purified vitronectin as previously described. (Charo, I. F., Nannizzi, L., Phillips, D. R., Hsu, M. A., Scarborough, R. M., "Inhibition of fibrinogen binding to GP IIb/IIIa by a GP IIIa peptide", *J. Biol. Chem.* 266(3) (1991): 1415–1421.) Assay buffer, OPD substrate tablets, and RIA grade BSA were obtained from Sigma (St. Louis, Mo.). Anti-biotin antibody was obtained from Calbiochem (La Jolla, Calif.). Linbro microtiter plates were obtained from Flow Labs (McLean, Va.). ADP reagent was obtained from Sigma (St. Louis, Mo.).

Methods
Solid Phase Receptor Assays

This assay is essentially the same reported in Niiya, K., Hodson, E., Bader, R., Byers-Ward, V. Koziol, J. A., Plow, E. F. and Ruggeri, Z. M., "Increased surface expression of the membrane glycoprotein IIb/IIIa complex induced by platelet activation: Relationships to the binding of fibrinogen and platelet aggregation", *Blood* 70(1987):475–483. The purified human fibrinogen receptor ($\alpha_{IIb}\beta_3$) was diluted from stock solutions to 1.0 μg/mL in Tris-buffered saline containing 1.0 mM $Ca^{++}$, $Mg^{++}$, and $Mn^{++}$, pH 7.4 (TBS$^{+++}$). The diluted receptor was immediately transferred to Linbro microtiter plates at 100 μL/well (100 ng receptor/well). The plates were sealed and incubated overnight at 4° C. to allow the receptor to bind to the wells. All remaining steps were at room temperature. The assay plates were emptied and 200 μL of 1% RIA grade BSA in TBS$^{+++}$ (TBS$^{+++}$/BSA) were added to block exposed plastic surfaces. Following a 2 hour incubation, the assay plates were washed with TBS$^{+++}$ using a 96 well plate washer. Logarithmic serial dilution of the test compound and controls were made starting at a stock concentration of 2 mM and using 2 nM biotinylated vitronectin in TBS$^{+++}$/BSA as the diluent. This premixing of labeled ligand with test (or control) ligand, and subsequent transfer of 50 μL aliquots to the assay plate was carried out with a CETUS Propette robot; the final concentration of the labeled ligand was 1 nM and the highest concentration of test compound was 1.0× $10^{-4}$ M. The competition occurred for two hours after which all wells were washed with a plate washer as before. Affinity purified horseradish peroxidase labeled goat anti-biotin antibody was diluted 1:3000 in TBS$^{+++}$/BSA and 125 μL were added to each well. After 30 minutes, the plates were washed and incubated with ODD/$H_2O_2$ substrate in 100 mM/L citrate buffer, pH 5.0. The plate was read with a microtiter plate reader at a wavelength of 450 nm and when the maximum-binding control wells reached an absorbance of about 1.0, the final $A_{450}$ were recorded for analysis. The data were analyzed using a macro written for use with the EXCEL™ spreadsheet program. The mean, standard deviation, and % CV were determined for duplicate concentrations. The mean $A_{450}$ values were normalized to the mean of four maximum-binding controls (no competitor added) (B-MAX). The normalized values were subjected to a four parameter curve fit algorithm, [Robard et al., *Int. Atomic Energy Agency, Vienna*, pp 469 (1977)], plotted on a semi-log scale, and the computed concentration corresponding to inhibition of 50% of the maximum binding of biotinylated vitronectin ($IC_{50}$) and corresponding $R^2$ was reported for those compounds exhibiting greater than 50% inhibition at the highest concentration tested; otherwise the $IC_{50}$ is reported as being greater than the highest concentration tested. β-[[2-[[5-[(aminoiminomethyl)amino]-1-oxopentyl]amino]-1-oxoethyl]amino]-3-pyridinepropanoic acid [U.S. Ser. No. 08/375,338, Example 1] which is a potent $\alpha_v\beta_3$ antagonist ($IC_{50}$ in the range 3–10 nM) was included on each plate as a positive control.

TABLE I

| Example | AvB3 IC50 (nM) | IIb/IIIa IC50 (nM) |
| --- | --- | --- |
| 2 | 0.18 | 8.08 |
| 6 | 0.51 | 49.5 |
| 10 | 1.17 | 26.9 |
| 11 | 2.2 | 4 |
| 12 | >100000 | 69200 |
| 19 | >100000 | 1780 |
| 20 | >100000 | 39900 |
| 24 | 1220 | 4530 |
| 28 | 555 | 10100 |
| 29 | 4000 | 1280 |
| 30 | 6370 | 3260 |
| 31 | 114 | 66.5 |
| 33 | 73.6 | 7.37 |
| 34 | 45.2 | 2200 |
| 35 | 2.69 | 148 |
| 36 | 1010 | 10500 |
| 37 | 97.8 | 2380 |
| 38 | 106 | 3360 |
| 40 | 557 | 748 |
| 41 | 1080 | 5700 |
| 44 | 120 | 4310 |
| 45 | 39.4 | 603 |
| 47 | 5.89 | 51.1 |
| 48 | 0.63 | 15.6 |
| 49 | 1.1 | 31.4 |
| 50 | 0.8 | 21.7 |
| 51 | 0.63 | 0.71 |
| 52 | 0.33 | 1.88 |

TABLE I-continued

| Example | AvB3 IC50 (nM) | IIb/IIIa IC50 (nM) |
|---|---|---|
| 53 | 0.56 | 15.3 |
| 54 | 0.77 | 36.5 |
| 55 | 0.51 | 14.3 |
| 56 | 0.43 | 6.35 |
| 57 | 14.5 | 318 |
| 58 | 48400 | 57200 |
| 59 | 4480 | 478 |
| 60 | 3370 | 3810 |
| 61 | 470 | 666 |
| 62 | 28100 | 14800 |
| 64 | 21.2 | 93.1 |
| 65 | 4760 | 21900 |
| 68 | 782 | 103 |
| 69 | 94 | 37 |
| 71 | 38.7 | 8.3 |
| 73 | 141 | 40 |
| 75 | 14.5 | 330 |
| 77 | 1.6 | 1260 |
| 78 | 5980 | 397 |
| 79 | 2290 | 10200 |
| 80 | 44200 | 19800 |
| 81 | 19.1 | 129 |
| 82 | 264 | 332 |
| 83 | 1900 | 474 |
| 84 | 16300 | 486 |
| 85 | 827 | 12600 |
| 85C | 39600 | 66000 |
| 86 | 307 | 3140 |
| 86C | 56800 | >100000 |
| 87 | 0.44 | 85.3 |
| 89 | 2070 | 16000 |
| 90 | 23700 | 34500 |
| 100 | 6 | 44 |
| 101A | 9 | 57 |
| 101B | 35 | 286 |
| 102 | 6 | 4710 |
| 103 | 269 | 3660 |
| 104 | 506 | 1600 |
| 105 | 2 | 267 |
| 106 | 5 | 77 |
| 107 | 0.5 | 1570 |
| 108 | 4 | 109 |
| 109 | 5 | 111 |
| 110 | 4 | 326 |
| 111 | 0.1 | 6 |
| 112 | 0.3 | 13 |
| 113 | 1 | 253 |
| 114 | 0.2 | 1000 |
| 115 | 24 | 173 |
| 116 | 6 | 3180 |
| 117 | 129 | 452 |
| 118 | 3 | 54 |
| 119 | 0.4 | 772 |
| 120 | 14 | 384 |
| 121 | 1 | 2 |
| 122 | 7 | 50 |
| 123 | 0.5 | 1.5 |
| 124 | 3 | 285 |
| 125 | 7 | 260 |
| 126 | 2 | 36 |
| 127 | 0.6 | 22 |
| 128 | 216 | 20 |
| 129 | 265 | 5260 |

What is claimed is:

1. A compound of the formula

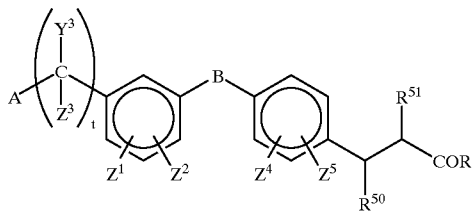

or a phamaceutically acceptable salt thereof, wherein

A is 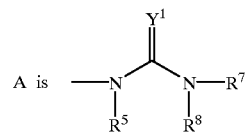

wherein $Y^1$ is selected from the group consisting of $N—R^2$, O, and S;

$R^2$ is selected from the group consisting of alkyl; aryl; alkoxy; cyano; nitro; amino; aminocarbonyl; alkenyl; alkynyl; alkyl optionally substituted with one or more substituent selected from lower alkyl, halogen, hydroxyl, haloalkyl, cyano, nitro, carboxyl, amino, alkoxy, aryl or aryl optionally substituted with one or more halogen, haloalkyl, lower alkyl, alkoxy, cyano, alkylsulfonyl, alkylthio, nitro, carboxyl, amino, hydroxyl, sulfonic acid, sulfonamide, aryl, fused aryl, aryl optionally substituted with one or more substituent selected from halogen, haloalkyl, hydroxy, lower alkyl, alkoxy, cyano, nitro, alkylthio, alkylsulfonyl, sulfonic acid, sulfonamide, carboxyl derivatives, amino, aryl, $R^7$ and $R^8$ are independently selected from the group consisting of H; alkyl; alkenyl; alkynyl; aralkyl; cycloalkyl; bicycloalkyl; aryl; acyl; benzoyl; alkyl optionally substituted with one or more substituent selected from lower alkyl, halogen, hydroxy, haloalkyl, cyano, nitro, carboxyl derivatives, amino, alkoxy, thio, alkylthio, sulfonyl, aryl, aralkyl, aryl optionally substituted with one or more substituent selected from halogen, haloalkyl, lower alkyl, alkoxy, alkylthio, haloalkylthio, thio, hydroxy, cyano, nitro, carboxyl derivatives, aryloxy, amido, acylamino, amino, alkylamino, dialkylamino, trifluoroalkoxy, trifluoromethyl, sulfonyl, alkylsulfonyl, haloalkylsulfonyl, sulfonic acid, sulfonamide, aryl, aryl optionally substituted with one or more substituent selected from halogen, haloalkyl, lower alkyl, alkoxy, alkylthio, haloalkylthio, thio, hydroxy, cyano, nitro, carboxyl derivatives, aryloxy, amido, acylamino, amino, alkylamino, dialkylamino, trifluoroalkoxy, trifluoromethylsulfonyl, alkylsulfonyl, sulfonic acid, sulfonamide, aryl, —$SO_2R^{10}$ wherein $R^{10}$ is selected from the group consisting of alkyl, and aryl and all optionally substituted with one or more substituent selected from the group consisting of halogen, haloalkyl, alkyl, alkoxy, cyano, nitro, amino, acylamino, trifluoroalkyl, amido, alkylaminosulfonyl, alkylsulfonyl, alkylsulfonylamino, alkylamino, dialkylamino, trifluoromethylthio, trifluoroalkoxy, trifluoromethylsulfonyl, aryl, aryloxy, thio, and alkylthio, and

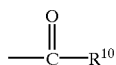

wherein $R^{10}$ is defined above; $R^5$ is selected from the group consisting of H, alkyl, alkenyl, alkynyl, benzyl, and phenethyl;

$Z^1$, $Z^2$, $Z^4$ and $Z^5$ are independently selected from the group consisting of H; alkyl; hydroxy; alkoxy; aryloxy; aralkoxy; halogen; haloalkyl; haloalkoxy; nitro; amino; aminoalkyl; alkylamino; dialkylamino; cyano; alkylthio; alkylsulfonyl; carboxyl derivatives; carboxyalkyl; alkoxycarbonylalkyl; acetamide; aryl; cycloalkyl; thio; and A, wherein A is defined above;

B is selected from the group consisting of

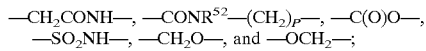

wherein p is an integer selected from the group consisting of 0, 1 and 2;

wherein $R^{50}$ is selected from the group consisting of H, alkyl, aryl, carboxyl derivative and —$CONHCH_2CO_2R^{53}$ wherein $R^{53}$ is H or lower alkyl;

$R^{52}$ is selected from the group consisting of H or alkyl;

$R^{51}$ is selected from the group consisting of H, alkyl, carboxyl derivatives, —$NHSO_2R^{54}$, and $NHCONHR^{54}$;

wherein $R^{54}$ is selected from the group consisting of H, alkyl, cycloalkyl, aryl, aralkyl, aralkenyl and aryl substituted by one or more alkyl or halo;

t is 0;

R is X—$R^3$ wherein X is selected from the group consisting of O, S and $NR^4$, wherein $R^3$ and $R^4$ are independently selected from the group consisting of hydrogen; alkyl; alkenyl; alkynyl; haloalkyl; aryl; arylalkyl; and in the case of the free acid, all pharmaceutically acceptable salts thereof.

2. A compound according to claim 1 wherein B is $CONR^{52}$—$(CH_2)_p$—.

3. A compound according to claim 1 wherein B is selected from the group consisting of —$CH_2O$—,

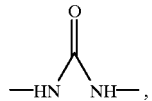

and —$SO_2NH$—.

4. A compound according to claim 1 wherein B is selected from the group consisting of —$CONR^{52}(CH_2)_p$— wherein p is 1 or 2 and $CH_2CONH$.

5. A compound according to claim 4 wherein the compound is selected from the group consisting of ethyl 4-[[[[3-(aminoiminomethyl)phenyl]-carbonyl]amino]methyl]benzenepropanoate;

ethyl 4-[[[[3-[amino(hydroxyimino)methyl]-phenyl]carbonyl)amino]methyl]benzenepropanoate;

4-[[[[3-(aminoiminomethyl)phenyl]carbonyl]-amino]methyl]benzenepropanoic acid;

3-[[[[3-[(aminocarbonyl)amino]phenyl]-carbonyl]amino]methyl]benzenepropanoic acid;

4-[[[[3-[(aminoiminomethyl)amino]phenyl]carbonyl]-amino]methyl]benzenepropanoic acid;

1,1-dimethylethyl-4-[2-[[[3-[(aminoiminomethyl)-amino]phenyl]carbonyl]amino]ethyl]benzenepropanoate;

4-[2-[[[3-[(aminoiminomethyl)amino]phenyl]-carbonyl]amino]ethyl]benzenepropanoic acid; and 4-[[2-[4-[(aminoiminomethyl)amino]phenyl]-acetyl]amino]benzenepropanoic acid.

6. A pharmaceutical composition comprising a therapeutically effective amount of a compound of the formula

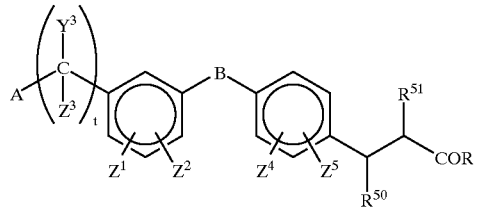

or a pharmaceutically acceptable salt thereof, wherein

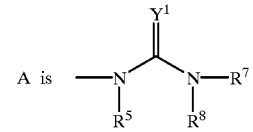

wherein $Y^1$ is selected from the group consisting of N—$R^2$, O, and S;

$R^2$ is selected from the group consisting of alkyl; aryl; alkoxy; cyano; nitro; amino; aminocarbonyl; alkenyl; alkynyl; alkyl optionally substituted with one or more substituent selected from lower alkyl, halogen, hydroxyl, haloalkyl, cyano, nitro, carboxyl, amino, alkoxy, aryl or aryl optionally substituted with one or more halogen, haloalkyl, lower alkyl, alkoxy, cyano, alkylsulfonyl, alkylthio, nitro, carboxyl, amino, hydroxyl, sulfonic acid, sulfonamide, aryl, fused aryl, aryl optionally substituted with one or more substituent selected from halogen, haloalkyl, hydroxy, lower alkyl, alkoxy, cyano, nitro, alkylthio, alkylsulfonyl, sulfonic acid, sulfonamide, carboxyl derivatives, amino, aryl;

$R^7$ and $R^8$ are independently selected from the group consisting of H; alkyl; alkenyl; alkynyl; aralkyl; cycloalkyl; bicycloalkyl; aryl; acyl; benzoyl; alkyl optionally substituted with one or more substituent selected from lower alkyl, halogen, hydroxy, haloalkyl, cyano, nitro, carboxyl derivatives, amino, alkoxy, thio, alkylthio, sulfonyl, aryl, aralkyl, aryl optionally substituted with one or more substituent selected from halogen, haloalkyl, lower alkyl, alkoxy, alkylthio, haloalkylthio, thio, hydroxy, cyano, nitro, carboxyl derivatives, aryloxy, amido, acylamino, amino, alkylamino, dialkylamino, trifluoroalkoxy, trifluoromethyl, sulfonyl, alkylsulfonyl, haloalkylsulfonyl, sulfonic acid, sulfonamide, aryl, aryl optionally substituted with one or more substituent selected from halogen, haloalkyl, lower alkyl, alkoxy, alkylthio, haloalkylthio, thio, hydroxy, cyano, nitro, carboxyl derivatives, aryloxy, amido, acylamino, amino, alkylamino, dialkylamino, trifluoroalkoxy, trifluoromethylsulfonyl, alkylsulfonyl, sulfonic acid, sulfonamide, aryl, —$SO_2R^{10}$ wherein $R^{10}$ is selected from the group consisting of alkyl, and aryl all optionally substituted with one or more substituent selected from the group consisting of halogen, haloalkyl, alkyl, alkoxy, cyano, nitro, amino, acylamino, trifluoroalkyl, amido, alkylaminosulfonyl, alkylsulfonyl, alkylsulfonylamino, alkylamino, dialkylamino, trifluoromethylthio, trifluoroalkoxy, trifluoromethylsulfonyl, aryl, aryloxy, thio, and alkylthio; and

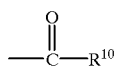

wherein $R^{10}$ is defined above; $R^5$ is selected from the group consisting of H, alkyl, alkenyl, alkynyl, benzyl, and phenethyl;

$Z^1$, $Z^2$, $Z^4$ and $Z^5$ are independently selected from the group consisting of H; alkyl; hydroxy; alkoxy; aryloxy; aralkoxy; halogen; haloalkyl; haloalkoxy; nitro; amino; aminoalkyl; alkylamino; dialkylamino; cyano; alkylthio; alkylsulfonyl; carboxyl derivatives; carboxyalkyl; alkoxycarbonylalkyl; acetamide; aryl; cycloalkyl; thio; and A, wherein A is defined above;

B is selected from the group consisting of

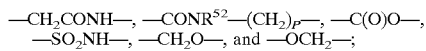

wherein p is an integer selected from the group consisting of 0, 1 and 2;

wherein $R^{50}$ is selected from the group consisting of H, alkyl, aryl, carboxyl derivative and —CONHCH$_2$CO$_2$R$^{53}$ wherein $R^{53}$ is H or lower alkyl;

$R^{52}$ is selected from the group consisting of H or alkyl;

$R^{51}$ is selected from the group consisting of H, alkyl, carboxyl derivatives, NHSO$_2$R$^{54}$, and —NHCONHR$^{54}$;

wherein $R^{54}$ is selected from the group consisting of H, alkyl, cycloalkyl, aryl, aralkyl aralkenyl and aryl substituted by one or more alkyl or halo;

t is 0;

R is X—R$^3$ wherein X is selected from the group consisting of O, S and NR$^4$, wherein R$^3$ and R$^4$ are independently selected from the group consisting of hydrogen; alkyl; alkenyl; alkynyl; haloalkyl; aryl; arylalkyl; and in the case of the free acid, all pharmaceutically acceptable salts thereof;

and a pharmaceutically acceptable carrier.

7. A pharmaceutical composition according to claim 6 wherein B is CONR$^{52}$—(CH$_2$)$_p$—.

8. A pharmaceutical composition according to claim 6 wherein B is selected from the group consisting of —CH$_2$O—,

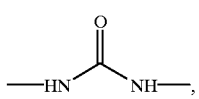

and —SO$_2$NH—.

9. A pharmaceutical composition according to claim 6 wherein B is selected from the group consisting of —CONR$^{52}$(CH$_2$)$_p$— wherein p is 1 or 2 and CH$_2$CONH.

10. A pharmaceutical composition according to claim 9 wherein the compound is selected from the group consisting of ethyl 4-[[[[3-(aminoiminomethyl)phenyl]-carbonyl]amino]methyl]benzenepropanoate;

ethyl 4-[[[[3-[amino(hydroxyimino)methyl]-phenyl]carbonyl)amino]methyl]benzenepropanoate;

4-[[[3-(aminoiminomethyl)phenyl]carbonyl]-amino]methyl]benzenepropanoic acid;

3-[[[[3-[(aminocarbonyl)amino]phenyl]carbonyl]amino]methyl]benzenepropanoic acid;

4-[[[[3-[(aminoimiimethyl)amino]phenyl]carbonyl]-amino]methyl]benzenepropanoic acid;

1,1-dimethylethyl-4-[2-[[[3-[(aminoiminomethyl)-amino]phenyl]carbonyl]amino]ethyl] benzenepropanoate;

4-[2-[[[3-[(aminoiminomethyl)amino]phenyl]-carbonyl]amino]ethyl]benzenepropanoic acid; and 4-[[2-[4-[(aminoiminomethyl)amino]phenyl]-acetyl]amino]benzenepropanoic acid.

11. A method for treating conditions mediated by the $\alpha_v\beta_3$ integrin in a mammal in need of such treatment comprising administering a therapeutically effective $\alpha_v\beta_3$ inhibiting amount of a compound of the formula

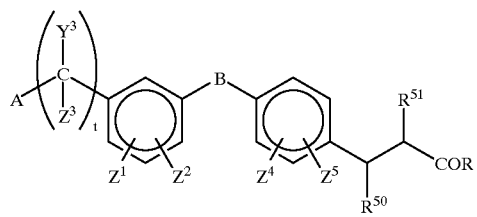

or a pharmaceutically acceptable salt thereof, wherein

A is 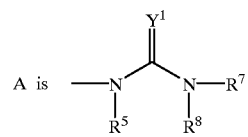

wherein $Y^1$ is selected from the group consisting of N—R$^2$, O, and S;

$R^2$ is selected from the group consisting of alkyl; aryl; alkoxy; cyano; nitro; amino; aminocarbonyl; alkenyl; alkynyl; alkyl optionally substituted with one or more substituent selected from lower alkyl, halogen, hydroxyl, haloalkyl, cyano, nitro, carboxyl, amino, alkoxy, aryl or aryl optionally substituted with one or more halogen, haloalkyl, lower alkyl, alkoxy, cyano, alkylsulfonyl, alkylthio, nitro, carboxyl, amino, hydroxyl, sulfonic acid, sulfonamide, aryl, fused aryl, aryl optionally substituted with one or more substituent selected from halogen, haloalkyl, hydroxy, lower alkyl, alkoxy, cyano, nitro, alkylthio, alkylsulfonyl, sulfonic acid, sulfonamide, carboxyl derivatives, amino, and aryl $R^7$ and $R^8$ are independently selected from the group consisting of H; alkyl; alkenyl; alkynyl; aralkyl; cycloalkyl; bicycloalkyl; aryl; acyl; benzoyl; alkyl optionally substituted with one or more substituent selected from lower alkyl, halogen, hydroxy, haloalkyl, cyano, nitro, carboxyl derivatives, amino, alkoxy, thio, alkylthio, sulfonyl, aryl, aralkyl, aryl optionally substituted with one or more substituent selected from halogen, haloalkyl, lower alkyl, alkoxy, alkylthio, haloalkylthio, thio, hydroxy, cyano, nitro, carboxyl derivatives, aryloxy, amido, acylamino, amino, alkylamino, dialkylamino, trifluoroalkoxy, trifluoromethyl, sulfonyl, alkylsulfonyl, haloalkylsulfonyl, sulfonic acid, sulfonamide, aryl, aryl optionally substituted with one or more substituent selected from halogen, haloalkyl, lower alkyl, alkoxy, alkylthio, haloalkylthio, thio, hydroxy, cyano, nitro, carboxyl derivatives, aryloxy, amido, acylamino, amino, alkylamino, dialkylamino, trifluoroalkoxy, trifluoromethylsulfonyl, alkylsulfonyl, sulfonic acid, sulfonamide, aryl, —SO$_2$R$^{10}$ wherein R$^{10}$ is selected from the group consisting of alkyl, and aryl all optionally substituted with one or more substituent selected from the group consisting of halogen, haloalkyl, alkyl, alkoxy, cyano, nitro, amino, acylamino, trifluoroalkyl, amido, alkylaminosulfonyl, alkylsulfonyl, alkylsulfonylamino, alkylamino, dialkylamino, tnrfluoromethylthio, trifluoroalkoxy, trifluoromethylsulfonyl, aryl, aryloxy, thio, and alkylthio, and

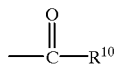

wherein R$^{10}$ is defined above; R$^5$ is selected from the group consisting of H, alkyl, alkenyl, alkynyl, benzyl, and phenethyl;

or

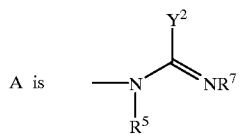

wherein Y$^2$ is selected from the group consisting of H, alkyl; cycloalkyl; bicycloalkyl; aryl; alkyl optionally substituted with aryl which can also be optionally substituted with one or more substituent selected from halo, haloalkyl, alkyl, nitro, hydroxy, alkoxy, aryloxy, aryl, aryl optionally substituted with one or more substituent selected from halo, haloalkyl, hydroxy, alkoxy, aryloxy, aryl, fused aryl, nitro, or alkyl; alkynyl; alkenyl; —S—R$^9$ and —O—R$^9$ wherein R$^9$ is selected from the group consisting of H; alkyl; aralkyl; aryl; alkenyl; and alkynyl; and
R$^5$ and R$^7$ are as defined above;

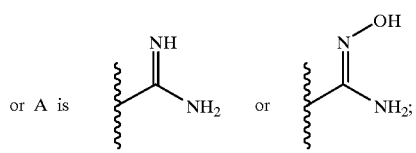

Z$^1$, Z$^2$, Z$^4$ and Z$^5$ are independently selected from the group consisting of H; alkyl; hydroxy; alkoxy; aryloxy; aralkoxy; halogen; haloalkyl; haloalkoxy; nitro; amino; aminoalkyl; alkylamino; dialkylamino; cyano; alkylthio; alkylsulfonyl; carboxyl derivatives; carboxyalkyl; alkoxycarbonylalkyl; acetamide; aryl; cycloalkyl; thio; and A, wherein A is defined above;

B is selected from the group consisting of

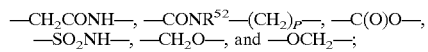

wherein p is an integer selected from the group consisting of 0, 1 and 2;
wherein R$^{50}$ is selected from the group consisting of H, alkyl, aryl, carboxyl derivative and —CONHCH$_2$CO$_2$R$^{53}$ wherein R$^{53}$ is H or lower alkyl;
R$^{52}$ is selected from the group consisting of H or alkyl;
R$^{51}$ is selected from the group consisting of H, alkyl, carboxyl derivatives, —NHSO$_2$R$^{54}$, and —NHCONHR$^{54}$;
wherein R$^{54}$ is selected from the group consisting of H, alkyl, cycloalkyl, aryl, aralkyl, aralkenyl and aryl substituted by one or more alkyl or halo;
t is 0;
R is X—R$^3$ wherein X is selected from the group consisting of O, S and NR$^4$, wherein R$^3$ and R$^4$ are independently selected from the group consisting of hydrogen; alkyl; alkenyl; alkynyl; haloalkyl; aryl; aralalkyl; and in the case of the free acid, all pharmaceutically acceptable salts thereof.

12. A method according to claim 11 wherein the condition treated is tumor metastasis.
13. A method according to claim 11 wherein the condition treated is tumor metastasis.
14. A method according to claim 11 wherein the condition treated is solid tumor growth.
15. A method according to claim 11 wherein the condition treated is solid tumor growth.
16. A method according to claim 11 wherein the condition treated is angiogenesis.
17. A method according to claim 11 wherein the condition treated is angiogenesis.
18. A method according to claim 11 wherein the condition treated is osteoporosis.
19. A method according to claim 11 wherein the condition treated is osteoporosis.
20. A method according to claim 11 wherein the condition treated is humoral hypercalcemia of malignancy.
21. A method according to claim 11 wherein the condition treated is humoral hypercalcemia of malignancy.
22. A method according to claim 11 wherein the condition treated is smooth muscle cell migration.
23. A method according to claim 11 wherein the condition treated is smooth muscle cell migration.
24. A method according to claim 11 wherein restenosis is inhibited.
25. A method according to claim 11 wherein restenosis is inhibited.
26. A compound according to claim 3 wherein the compound is 4-[[3-[(aminoiminomethyl)amino]phenyl]-sulfonyl]amino]benzenepropanoic acid.
27. A pharmaceutical composition according to claim 8 wherein the compound is
   4-[[3-[(aminoiminomethyl)amino]phenyl]-sulfonyl]amino]benzenepropanoic acid.
28. A compound according to claim 2 selected from the group consisting of
   ethyl 4-[[[3-[amino(hydroxyimino)methyl]-phenyl]carbonyl]amino]benzenepropanoate;
   ethyl 3-[[[3-(aminoiminomethyl)phenyl]-carbonyl]amino]methyl]benzenepropanoate;

ethyl 3-[[[3-(aminoiminomethyl)phenyl]-carbonyl] amino]benzenepropanoate;
4-[[[3-(aminoiminomethyl)phenyl]carbonyl]-amino] benzenepropanoic acid;
ethyl 4-[[[3-[(aminocarbonyl)amino]phenyl]-carbonyl] amino]benzenepropanoate;
4-[[[3-[(aminocarbonyl)amino]phenyl]-carbonyl]amino] benzenepropanoic acid;
ethyl 4-[[[3-[[[(phenylmethyl)amino]carbonyl]-amino] phenyl]carbonyl]amino]benzenepropanoate;
4-[[[3-[[[(phenylmethyl)amino]carbonyl]amino]-phenyl] carbonyl]amino]benzenepropanoic acid;
1,1-dimethylethyl 4-[[[3-[(aminoiminomethyl)-amino] phenyl]carbonyl]amino-β-methylbenzenepropanoate;
4-[[[3-[(aminoiminomethyl)amino]phenyl]carbonyl]-amino]-β-methylbenzenepropanoic acid;
1,1-dimethylethyl 4-[[[3-[(aminoiminomethyl)-amino] phenyl]carbonyl]amino-β-phenyl benzenepropanoate;
4-[[[3-[(aminoiminomethyl)amino]phenyl]carbonyl]-amino]-β-phenylbenzenepropanoic acid;
ethyl 4-[[[3-[(aminoiminomethyl)amino]phenyl]-carbonyl]methylamino]benzenepropanoate;
4-[[[3-[(aminoiminomethyl)amino]phenyl]-carbonyl] methylamino]benzenepropanoic acid;
ethyl 4-[[[3-[(aminoiminomethyl)amino]-phenyl] carbonyl]amino]benzenepropanoate;
4-[[[3-[(aminoiminomethyl)amino]phenyl]carbonyl] amino]benzenepropanoic acid;
[4-[[[3-[(aminoiminomethyl)amino]phenyl]-carbonyl] amino]phenyl]butanedioic acid;
4-(1,1-dimethylethyl) 1-ethyl[4-[[[3-[(aminoiminomethyl)amino]phenyl]carbonyl]-amino] phenyl]butanedioate;
1-ethyl hydrogen [4-[[[3-[(aminoiminomethyl)amino]-phenyl]carbonyl]amino]-phenyl]butanedioate;
1,1-dimethylethyl 4-[[[3-[(aminoiminomethyl)amino]-phenyl]carbonyl]-amino]-β-[[[(ethoxycarbonyl)-methyl]amino]-carbonyl]benzenepropanoate;
4-[[[3-[(aminoiminomethyl)amino]phenyl]carbonyl-amino]-beta-[[(carboxymethyl)amino]-carbonyl]-benzenepropanoic acid;
1,1-dimethylethyl 4-[[[3-[(aminoiminomethyl)amino]-phenyl]carbonyl]amino]-3-hydroxybenzenepropanoate;
4-[[[3-[(aminoiminomethyl)amino]phenyl]carbonyl]-amino]3-hydroxybenzenepropanoic acid;
4-[[[3-[[(cyanoimino)[phenylmethyl)-amino]methyl] amino]phenyl]carbonyl]amino]-benzenepropanoic acid;
[4-[2-[[3-[(aminoiminomethyl)amino]phenyl]-amino]-2-oxoethyl]phenoxy]acetic acid;
4-[[[3-[(aminoiminomethyl)amino]phenyl]carbonyl] amino]benzene-1,2-dipropanoic acid;
4-[[[3-[(aminoiminomethyl)amino]phenyl]carbonyl]-amino]-2-carboxybenzenepropanoic acid;
4-[[[3-[(aminoiminomethyl)amino]phenyl]carbonyl]-amino]-2-methoxycarbonyl)benzenepropanoic acid;
4-[[[3-(aminoiminomethyl)amino]phenyl]carbonyl]-amino]-2-methoxybenzenepropanoic acid;
4-[[[3-[(aminoiminomethyl)amino]phenyl]carbonyl]-amino]-2-(dimethylamino)benzenepropanoic acid;
[4-[[[3-[(aminoiminomethyl)amino]phenyl]carbonyl]-amino]-2-methoxyphenoxy]acetic acid;
[[4-[[[3-[(aminoiminomethyl)amino]phenyl]carbonyl]-amino]phenyl]methyl]-1,3-propanoic acid.

29. A pharmaceutical composition according to claim 7 selected from the group consisting of
ethyl 4-[[[3-[amino(hydroxyimino)methyl]-phenyl] carbonyl]amino]benzenepropanoate;
ethyl 3-[[[3-(aminoiminomethyl)phenyl]-carbonyl] amino]methyl]benzenepropanoate;
ethyl 3-[[[3-(aminoiminomethyl)phenyl]-carbonyl] amino]benzenepropanoate;
4-[[[3-(aminoiminomethyl)phenyl]carbonyl]-amino] benzenepropanoic acid;
ethyl 4-[[[3-[(aminocarbonyl)amino]phenyl]-carbonyl] amino]benzenepropanoate;
4-[[[3-[(aminocarbonyl)amino]phenyl]-carbonyl]amino] benzenepropanoic acid;
ethyl 4-[[[3-[[[(phenylmethyl)amino]carbonyl]-amino] phenyl]carbonyl]amino]benzenepropanoate;
4-[[[3-[[[(phenylmethyl)amino]carbonyl]amino]phenyl] carbonyl]amino]benzenepropanoic acid;
1,1-dimethylethyl 4-[[[3-[(aminoiminomethyl)-amino] phenyl]carbonyl]amino-β-methylbenzenepropanoate;
4-[[[3-[(aminoiminomethyl)amino]phenyl]carbonyl]-amino]-β-methylbenzenepropanoic acid;
1,1-dimethylethyl 4-[[[3-[(aminoiminomethyl)-amino] phenyl]carbonyl]amino]-β-phenyl benzenepropanoate;
4-[[[3-[(aminoiminomethyl)amino]phenyl]carbonyl]-amino]-β-phenylbenzenepropanoic acid;
ethyl 4-[[[3-[(aminoiminomethyl)amino]phenyl]-carbonyl]methylamino]benzenepropanoate;
4-[[[3-[(aminoiminomethyl)amino]phenyl]-carbonyl] methylamino]benzenepropanoic acid;
ethyl 4-[[[3-[(aminoiminomethyl)amino]-phenyl] carbonyl]amino]benzenepropanoate;
4-[[[3-[(aminoiminomethyl)amino]phenyl]carbonyl] amino]benzenepropanoic acid;
[4-[[[3-[(aminoiminomethyl)amino]phenyl]-carbonyl] amino]phenyl]-butanedioic acid;
4-(1,1-dimethylethyl) 1-ethyl[4-[[[3-[(aminoiminomethyl)amino]phenyl]carbonyl]-amino] phenyl]butanedioate;
1-ethyl hydrogen[4-[[[3-[(aminoiminomethyl)amino]-phenyl]carbonyl]amino]-phenyl]butanedioate;
1,1-dimethylethyl 4-[[[3-[(aminoiminomethyl)amino]-phenyl]carbonyl]-amino]-β-[[[ethoxycarbonyl)-methyl]amino-carbonyl]benzenepropanoate;
4-[[[3-[(aminoiminomethyl)amino]phenyl]carbonyl]-amino]-beta-[[(carboxymethyl)amino]-carbonyl]-benzenepropanoic acid;
1,1-dimethylethyl 4-[[[3-[(aminoiminomethyl)amino]-phenyl]carbonyl]amino]-3-hydroxybenzenepropanoate;
4-[[[3-[(aminoiminomethyl)amino]-3-hydroxybenzenepropanoic acid;
4-[[[3-[[(cyanoimino)[(phenylmethyl)-amino]methyl] amino]phenyl]carbonyl]amino]-benzenepropanoic acid;
[4-[2-[[3-[(aminoiminomethyl)amino]phenyl]-amino]-2-oxoethyl]phenoxy]acetic acid;
4-[[[3-[(aminoiminomethyl)amino]phenyl]carbonyl] aminobenzene-1,2-dipropanoic acid;
4-[[[3-[(aminoiminomethyl)amino]phenyl]carbonyl]-amino]-2-carboxybenzenepropanoic acid;

4-[[[3-[(aminoiminomethyl)amino]phenyl]carbonyl]-amino]-2-methoxycarbonyl)benzenepropanoic acid;

4-[[[3-(aminoiminomethyl)amino]phenyl]carbonyl]-amino]-2-methoxybenzenepropanoic acid;

4-[[[3-[(aminoiminomethyl)amino]phenyl]carbonyl]-amino]-2-methoxyphenoxy]acetic acid; and

[[4-[[[3-[(aminoiminomethyl)amino]phenyl]carbonyl]-amino]phenyl]methyl]-1,3-propanoic acid.

30. The method according to claim 11 wherein the compound is selected from the group consisting of ethyl 4-[[[[3-(aminoiminomethyl)phenyl]-carbonyl]amino]methyl]benzenepropanoate;

ethyl 4-[[[3-[amino(hydroxyimino)methyl]-phenyl]carbonyl]amino]benzenepropanoate;

ethyl 3-[[[[3-(aminoiminomethyl)phenyl]-carbonyl]amino]methyl]benzenepropanoate;

ethyl 3-[[[3-(aminoiminomethyl)phenyl]-carbonyl]amino]benzenepropanoate;

4-[[[[3-(aminoiminomethyl)phenyl]carbonyl]-amino]methyl]benzenepropanoic acid;

4-[[[3-(aminoiminomethyl)phenyl]carbonyl]-amino]benzenepropanoic acid;

ethyl 4-[[[3-[(aminocarbonyl)amino]phenyl]-carbonyl]amino]benzenepropanoate;

3-[[[[3-[(aminocarbonyl)amino]phenyl]-carbonyl]amino]methyl]benzenepropanoic acid;

4-[[[3-[(aminocarbonyl)amino]phenyl]-carbonyl]amino]benzenepropanoic acid;

ethyl 4-[[[3-[[[(phenylmethyl)amino]carbonyl]-amino]phenyl]carbonyl]amino]benzenepropanoate;

4-[[[3-[[[(phenylmethyl)amino]carbonyl]amino]-phenyl]carbonyl]amino]benzenepropanoic acid;

4-[[[[3-[(aminoiminomethyl)amino]phenyl]carbonyl]-amino]methyl]benzenepropanoic acid;

1,1-dimethylethyl 4-[[[3-[(aminoiminomethyl)-amino]phenyl]carbonyl]amino]-β-methylbenzenepropanoate;

4-[[[3-[(aminoiminomethyl)amino]phenyl]carbonyl]-amino]-β-methylbenzenepropanoic acid;

1,1-dimethylethyl 4-[[[3-[(aminoiminomethyl)-amino]phenyl]carbonyl]amino]β-phenyl benzenepropanoate;

4-[[[3-[(aminoiminomethyl)amino]phenyl]carbonyl]-amino]-β-phenylbenzenepropanoic acid;

1,1-dimethylethyl-4-[2-[[[3-[(aminoiminomethyl)-amino]phenyl]carbonyl]amino]ethyl]benzenepropanoate;

4-[2-[[[3-[(aminoiminomethyl)amino]phenyl]-carbonyl]amino]ethyl]benzenepropanoic acid;

ethyl 4-[[[3-[(aminoiminomethyl)amino]phenyl]-carbonyl]methylamino]benzenepropanoate;

4-[[[3-[(aminoiminomethyl)amino]phenyl]-carbonyl]methylamino]benzenepropanoic acid;

4-[[[3-[(aminoiminomethyl)amino]phenyl]-sulfonyl]amino]benzenepropanoic acid;

ethyl 4-[[[3-[(aminoiminomethyl)amino]-phenyl]carbonyl]amino]benzenepropanoate;

4-[[[3-[(aminoiminomethyl)amino]phenyl]carbonyl]amino]benzenepropanoic acid;

[4-[[[3-[(aminoiminomethyl)amino]phenyl]-carbonyl]amino]phenyl]butanedioic acid;

4-(1,1-dimethylethyl) 1-ethyl [4-[[[3-[(aminoiminomethyl)amino]phenyl]carbonyl]-amino]phenyl]butanedioate;

1-ethyl hydrogen[4-[[[3-[(aminoiminomethyl)amino]-phenyl]carbonyl]amino]-phenyl]butanedioate;

1,1-dimethylethyl 4-[[[3-[(aminoiminomethyl)amino]-phenyl]carbonyl]-amino]-β-[[[(ethoxycarbonyl)-methyl]amino]-carbonyl]benzenepropanoate;

4-[[[3-[(aminoiminomethyl)amino]phenyl]carbonyl]-amino]-beta-[[(carboxymethyl)amino]-carbonyl]-benzenepropanoic acid;

1,1-dimethylethyl 4-[[[3-[(aminoiminomethyl)amino]-phenyl]carbonyl]amino]-3-hydroxybenzenepropanoate;

4-[[[3-[(aminoiminomethyl)amino]phenyl]carbonyl]-amino]-3-hydroxybenzenepropanoic acid;

4-[[2-[4-[(aminoiminomethyl)amino]phenyl]-acetyl]amino]benzenepropanoic acid;

4-[[[3-[[(cyanoimino)[phenylmethyl)-amino]methyl]amino]phenyl]carbonyl]amino]-benzenepropanoic acid;

[4-[2-[[3-[(aminoiminomethyl)amino]phenyl]-amino]-2-oxoethyl]phenoxy]acetic acid;

4-[[[3-[(aminoiminomethyl)amino]phenyl]carbonyl]amino]benzene-1,2-dipropanoic acid;

4-[[[3-[(aminoiminomethyl)amino]phenyl]carbonyl]-amino]-2-carboxybenzenepropanoic acid;

4-[[[3-[(aminoiminomethyl)amino]phenyl]carbonyl]-amino]-2-methoxycarbonyl)benzenepropanoic acid;

4-[[[3-(aminoiminomethyl)amino]phenyl]carbonyl]-amino]-2-methoxybenzenepropanoic acid;

4-[[[3-[(aminoiminomethyl)amino]phenyl]carbonyl]-amino]-2-(dimethylamino)benzenepropanoic acid;

[4-[[[3-[(aminoiminomethyl)amino]phenyl]carbonyl]-amino]-2-methoxyphenoxy]acetic acid; and

[[4-[[[3-[(aminoiminomethyl)amino]phenyl]carbonyl]-amino]phenyl]methyl]-1,3-propanoic acid.

\* \* \* \* \*